US007737262B2

(12) United States Patent
Chang et al.

(10) Patent No.: US 7,737,262 B2
(45) Date of Patent: *Jun. 15, 2010

(54) PLASMODIUM FALCIPARUM POLYPEPTIDES AND METHODS OF USING SAME

(75) Inventors: Sandra Chang, Honolulu, HI (US); Ann Hashimoto, Kaneohe, HI (US); Tani Nishimura, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 717 days.

This patent is subject to a terminal disclaimer.

(21) Appl. No.: 10/935,793

(22) Filed: Sep. 7, 2004

(65) Prior Publication Data

US 2005/0037021 A1 Feb. 17, 2005

Related U.S. Application Data

(60) Division of application No. 10/062,809, filed on Feb. 1, 2002, now abandoned, and a continuation-in-part of application No. 09/500,376, filed on Feb. 8, 2000, now Pat. No. 6,855,316.

(60) Provisional application No. 60/266,281, filed on Feb. 1, 2001.

(51) Int. Cl.
| A01H 1/00 | (2006.01) |
| C07H 21/04 | (2006.01) |
| C07H 21/02 | (2006.01) |
| C12P 21/06 | (2006.01) |
| C12N 15/00 | (2006.01) |

(52) U.S. Cl. ............... 536/23.1; 536/23.7; 536/23.5; 435/69.3; 435/320.1; 435/69.7; 800/278

(58) Field of Classification Search .......... None
See application file for complete search history.

(56) References Cited

U.S. PATENT DOCUMENTS

| 4,745,051 | A | 5/1988 | Smith et al. | |
| 5,474,914 | A | 12/1995 | Spaete | |
| 6,270,800 | B1 | 8/2001 | Speaker et al. | |
| 6,420,523 | B1 * | 7/2002 | Chang et al. | 530/350 |
| 6,855,316 | B1 * | 2/2005 | Chang et al. | 424/185.1 |
| 7,037,681 | B2 * | 5/2006 | Chang et al. | 435/69.1 |
| 7,256,281 | B2 * | 8/2007 | Angov et al. | 536/23.7 |
| 7,285,274 | B2 * | 10/2007 | Chang et al. | 424/185.1 |
| 2002/0058787 | A1 | 5/2002 | Strominger et al. | |
| 2002/0076403 | A1 * | 6/2002 | Longacre-Andre et al. | 424/130.1 |
| 2002/0194648 | A1 * | 12/2002 | Chang et al. | 800/294 |
| 2003/0100106 | A1 * | 5/2003 | Chang et al. | 435/350 |
| 2005/0037021 | A1 * | 2/2005 | Chang et al. | 424/191.1 |
| 2005/0095255 | A1 * | 5/2005 | Chang et al. | 424/191.1 |
| 2008/0075741 | A1 * | 3/2008 | Angov et al. | 424/234.1 |

FOREIGN PATENT DOCUMENTS

| EP | 0 329 257 | 8/1989 |
| WO | WO 97/30159 * | 8/1997 |

OTHER PUBLICATIONS

Bowie, et al., "Deciphering the message in protein sequences: tolerance to amino acid substitutions," Science, 247, pp. 1306-1031 (1990).
Burghaus, et al., "Immunization of *Aotus nancymai* with Recombinant C Terminus of *Plasmodium falciparum* Merozoite Surface Protein 1 in Liposomes and Alum Adjuvant Does Not Induce Protection against a Challenge Infection," Infect. & Immun. 64(9):3614-9 (1996).
Chang, et al., "*Plasmodium falciparum*: Gene Structure and Hydropathy Profile of the Major Merozoite Surface Antigen (gp195) of the Uganda-Palo Alto Isolate" Experimental Parasitology, 67: 1-11 (1988).
Chang, SP et al., "Generalized immunological recognition of the major merozoite surface antigen (gp195) of *Plasmodium falciparum*," Proc. Natl. Acad. Sci. USA 86:6343-7 (1989).
Change, SP et al., "A Carboxyl-Terminal Fragment of *Plasmodium falciparum* gp195 Expressed by the Recombinant Baculovirus Induces Antibodies that Completely Inhibit Parasite Growth," J. Immunol. 149(2):548-555 (1992).
Cheung et al. "Immunization with synthetic peptides of a *Plasmodium falciparum* surface antigen induces antimerozoite antibodies," Proc. Natl. Acad. Sci. USA 83:8328 (1986).
Ellis, R.W., "New Technologies for Making Vaccines," in Vaccines, Plotkin, S.A. and Mortimer, Jr. E.A., eds., W.B. Saunders Co., Philadelphia (1988), Ch. 29, pp. 568-575.
Hall et al. "Major surface antigen gene of a human malaria parasite cloned and expressed in bacteria," Nature, 311:379 (1984).
Herrera et al. "Conserved Polypeptides of *Plasmodium falciparum* as Malaria Vaccine Candidates?", Acta Leidensia, 60(1):107-110 (1991).
Herrera et al. "Immunization of Aotus monkeys with *Plasmodium falciparum* blood-stage recombinant proteins," Proc. Natl. Acad. Sci. USA 87:4017 (1990).
Holder et al., "A hybrid gene to express protein epitopes from both sporozoite and merozoite surface antigens of *Plasmodium falciparum*," Parasitology, 97:373-382 (1988).
Holder et al., "Immunization against *Plasmodium falciparum* with recombinant polypeptides produced in *Escherichia coli*," Parastic Immunology, 10:607-617 (1988).
Holder et al., "Primary Structure of the Precursor to the three major surface antigens of *Plasmodium falciparum* merozoite," Nature, 317:270-273 (1985).
Holder et al., "Processing of the precursor to the major merozoite surface antigens of *Plasmodium falciparum*." Parasitology, 94:199-208 (1987).

(Continued)

Primary Examiner—N. M Minnifield
(74) Attorney, Agent, or Firm—K&L Gates LLP

(57) ABSTRACT

Compositions and methods are provided for the induction of a protective immunize response in primates against a lethal challenge of *Plasmodium*.

10 Claims, 31 Drawing Sheets

OTHER PUBLICATIONS

Holder et at. "Immunization against blood-stage rodent malaria using purified parasite antigens," *Nature*, 294:361 (1981).

Holder, A.A. et al., "Immunization against *Plasmodium falciparum* with recombinant polypeptides produced in *Escherichia coli*," *Parasite Immunology*, 10(6):607-617 (1988).

Hui et al. "Serum from Pf195 protected Aotus Monkeys Inhibit *Plasmodium falciparum* growth in Vitro," *Exp. Parasitol.* 64:519 (1987).

Hui, et al. "Induction of Antibodies to the *Plasmodium falciparum* Merozoite Surface Protein-1 (MSP1) by Cross-Priming with Heterologous MSPs" *J. of Immunology*, 153: 1195-1201 (1994).

Hui, et al., "Roles of Conserved and Allelic Regions of the Major Merozoite Surface Protein (gp195) in Immunity against *Plasmodium falciparum*" *Infection and Immunity*, 60:1422-1433 (1992).

Knapp, 6. et al. "A histidin alanine rich recombinant antigen protects aotus monkeys from *P. falciparium* infection," *Behrina Inst. Mitt.* 82:349-59 (1988).

Kumar. S et al.. "Immunogenicity and Efficacy in *Aotus* Monkeys of Four Recombinant *Plasmodium falciparum* Vaccines in Multiple Adjuvant Formulations Based on the 19-Kilodalton C Terminus of Merozoite Surface Protein 1 ," *Infect. & Immun.* 68(4):2215-2223 (2000).

Lew et al. "A protective monoclonal antibody recognizes a linear epitope in the precursor to the major merozoite antigens of *Plasmodium chabaudi adami*," *Proc. Natl. Acad. Sci. USA* 86:3768 (1989).

Locher, CP et at., "*Plasmodium falciparum*: gp195 Tripeptide Repeat-Specific Monoclonal Antibody Inhibits Parasite Growth in Vitro" *Exp. Parisitol.*, 84:74-83 (1996).

Majarian et al. "Passive Immunization against Murine Malaria with an IgG3 Monoclonal Antibody," *J. Immunol.* 132:3131 (1984).

Murphy, V.F. et al., "Expression of hybrid malaria anitgens in insect cells and their engineering for correct folding and secretion." *Parasitology*, 100 pt. 2:177-183 (1990).

Nishimura, T.A.T., "Distribution of MSP-1 Dimorphism in Papua New Guinea and the Importance of BVp42 Dimorphism in Antibody Recognition", Master of Science in MicrobiologyThesis, University of Hawaii (Dec. 1999).

Odink K.G. et al., "Expression of cloned cDNA for a major surface antigen of *Plasmodium falciparum* merozoite," *FEBS Lett.*, (1984) 108-12.

Patarroyo et al. "A synthetic vaccine protects humans against challenge with asexual blood stages of *Plasmodium falciparum* malaria." *Nature*, 332:158 (1988).

Patarroyo et al. "Induction of protective immunity against experimental infection with malaria using synthetic peptides," *Nature*, 328:629 (1987).

Patarroyo et al. "Protective Synthetic Peptides against Experimental *Plasmodium falciparum*-induced Malaria," Vaccines 87 (Brown, Chanock, Lerner. ed.) Cold Spring Harbor Laboratory Press, Cold Spring Harbor, NY. 117-124 (1987).

Perlaza et al., "Immunogenicity of four *Plasmodium falciparum* preerythrocytic antigens in *Aotus lemurinus* monkeys," *Infection and Immunity*, 66(7):3423-3438 (1998).

Perrin et al. "Antimalarial immunity in Saimiri monkeys. Immunization with surface components of asexual blood stages.," *J. Exp. Med.* 160:441-451 (1984).

Rodriguez et al. "Studies in Owl Monkeys Leading to the Development of a Synthetic Vaccine Against the Asexual Blood Stages of *Plasmodium falciparum*," *Am. J. Trop. Med. Hyg.* 43:339 (1990).

Ruebush et al.. "Immunization of Owl Monkeys with a Combination of *Plasmodium falciparum* Asexual Blood-Stage Synthetic Peptide Antigens," *Am. J. Trop. Med. Hyg.* 43:355-366 (1990).

Saul et al., Second African Malaria Vaccine Testing Network Meeting, Accra, Ghana, Nov. 24-26, 1997.

Schreiber, et al., "A eukaryotic expression vector for the study of nuclear localization signals," *Gene*, 150(2):411-412 (Dec. 1994).

Schwarz et al, "Structural Diversity of the Major Surface Antigen of *Plasmodium falciparum* Merozoites," *Mol. Cell. Biol.*, 6(3):964-968 (1986).

Siddiqui et al. "Merozoite surface coat precursor protein completely protects Aotus monkeys against *Plasmodium falciparum* malaria," 1987. *Proc. Natl. Acad. Sci. USA* 84:3014.

Smilek, D. et al., "A single amino acid change in myelin basic protein peptide confers the capacity to prevent rather than induce EAE", *Proc. Natl. Acad. Sci. USA* 88:9633-37 (1991).

Soltysik, "Structure/function studies of QS-21 adjuvant: assessment of triterpene aldehyde and glucuronic acid rules in adjuvant function," *Vaccine* 1995, 13(15):1403-1410.

Stowers, AW et al., "A recombinant vaccine expressed in the milk of transgenic mice protects Aotus monkeys from a lethal challenge with *Plasmodium falciparum*," 99(1):339-344 (2002).

Stowers, AW et al., "Efficacy of Two Alternate Vaccines Based on *Plasmodium falciparum* Merozoite Surface Protein 1 in an *Aotus* Challenge Trial," Infect. & Immun. 69(3):1536-46 (2001).

Swiss=Prot: P50495, Merozite protein surface protein1[Precursor], Sequence last modified Oct. 1996.

Tanabe, K. et al., "Allelic Dimorphism in a Surface Antigen Gene of the Malaria Parasite *Plasmodium falciparum*," *J. Mol. Biol.*, 195:273-287 (1987).

Wu, et al., "Saponin adjuvant enhancement of antigen-specific immune responses to an experimental HIV-1 vaccine," *Journal of Immunology*, 148(5):1519-1525 (1992).

* cited by examiner

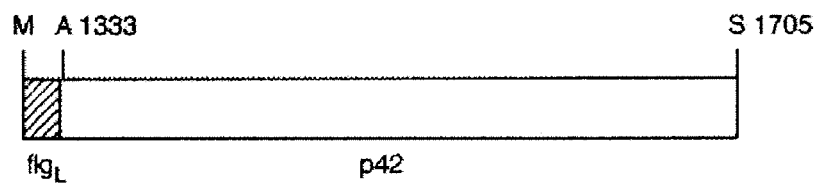
FIG._1A
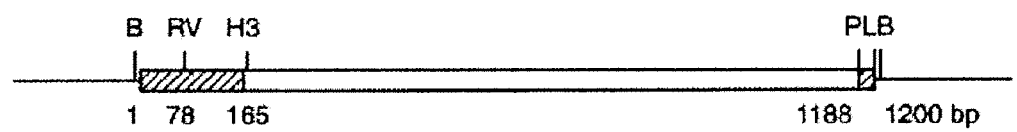
FIG._1B
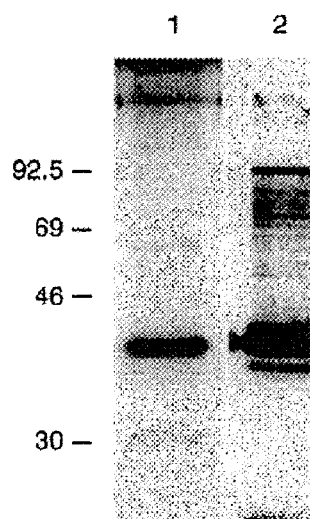
FIG._2A
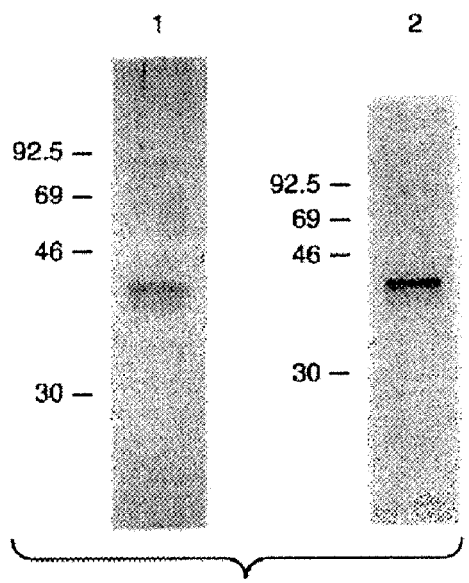
FIG._2B

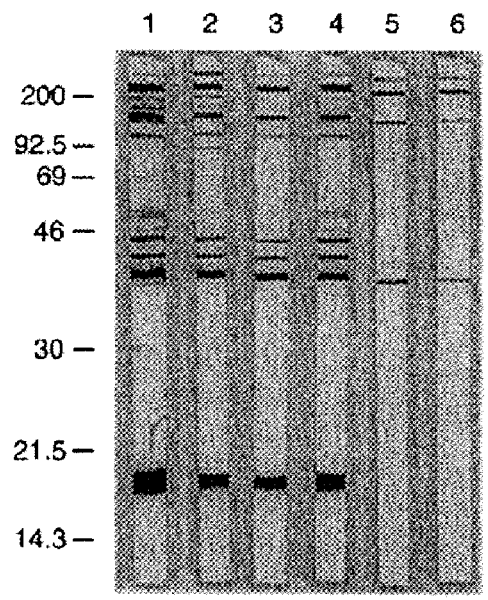
FIG._3A
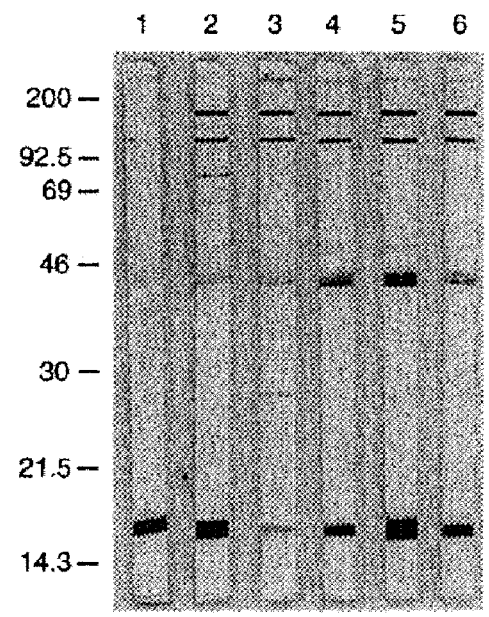
FIG._3B
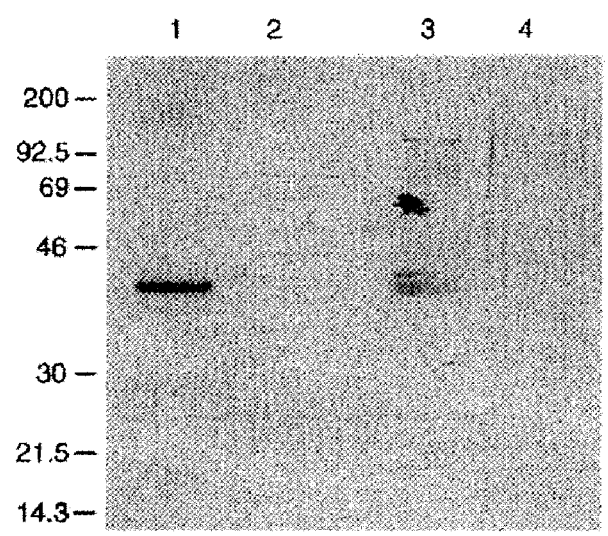
FIG._3C

Fig. 4
Fig. 4A
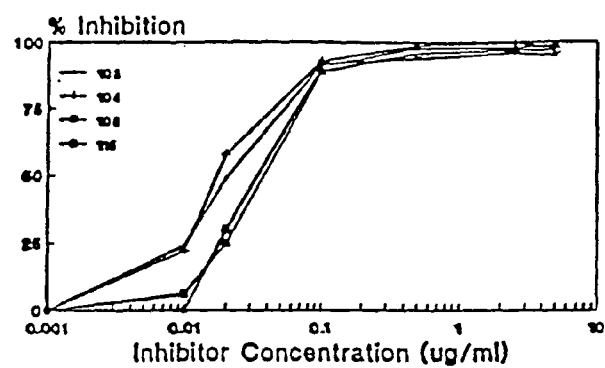
Fig. 4B
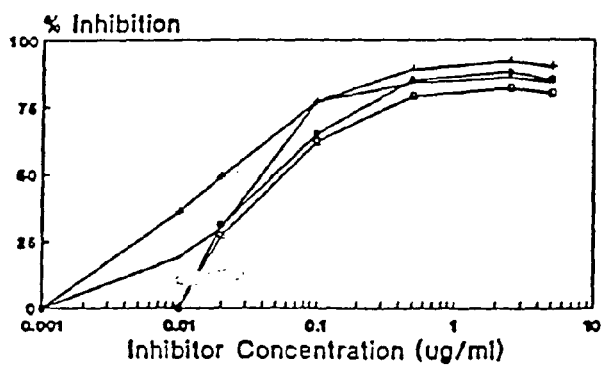
Fig. 4C
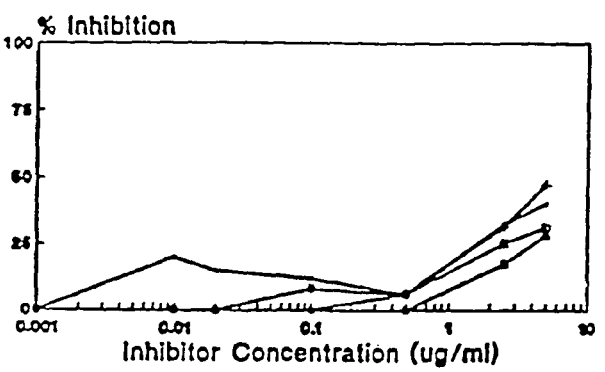

Fig. 6

```
FUP  AISVT.MDNILSGFENEYDVIYLKPLAGVYRSLKKQIEKNIFTFNLNLNDILNSRLKKRKYFLDVLESDLM    1402
MAD                                         I                                 1377
WEL  VTTSVI              KI        E L                       L N VM   V VK   FN  EN KN   I    1384
K1   VTPSVIH             KI        E L                       L N VM   V VK   PFN EN KN   I    1325

FUP  QFKHISSNEYIIEDSFKLLNSEQKNTLLKSYKYIKESVENDIKFAQEGISYYEKVLAKYKDDLESIKKVIK    1473
MAD                      I                                                     1448
WEL  PY DLT SN VVK PY F   K KRDKF S  N        D IDT N NDVLG KILSE    S D       Y N    1405
K1   PY DLT SN VVK PY F   K KRDKF S           D IDT N NDVLG KILSE    S D       Y N    1396

FUP  EEKEKFPSSPPTTPPSPAKTDEQKKESKFLPFLTNIETLYNNLVNKIDDYLINLKAKINDCNVEKDEAHVK    1544
MAD                                                                            1519
WEL  .............   K GENE Y   N            KTVND        LFV H E   VLNYTY  SNVE       1456
K1   .............   K GENE Y   N            KTVND        LFV H E   VLNYTY  SNVE       1447

FUP  ITKLSDLKAIDDKIDLFKNHHNDFEAIKKLINDDTKKDMLGKLLSTGLV.QNFPNTIISKLLEGKFQDML.N    1613
MAD                      T                              I                      1588
WEL  KE NY  T Q  LAD  KN N VG AD ST YNHNNL T F    M FE LLKSVL N LDW LARYVKH    1527
K1   KE IY  T Q  LAD  KN N VG AD ST YNHNNL T F    M FE LLKS  L N LDW LARYVKH    1518

FUP  ISQHQCVKKQCPENSGCFRHLDEREECKCLLNYKQEGDKCVENPNPTCNENNGGCDADAKCTEEDSGSNGK    1684
MAD                                              E                   T     SR  1659
WEL                                                                             1598
K1                                                                              1589

FUP  FTTPMRK TMIQQS                                                             1726
MAD  FTTPMRK TMIQQ                         S                                    1701
WEL                                                                             1640
K1                                                                              1631

FUP  KITCECTKPDSYPLFDGIFCSSSNFLGISFLLIMLILYSFI
MAD        C                  Q
WEL
K1                            SMV
```

Fig. 7A

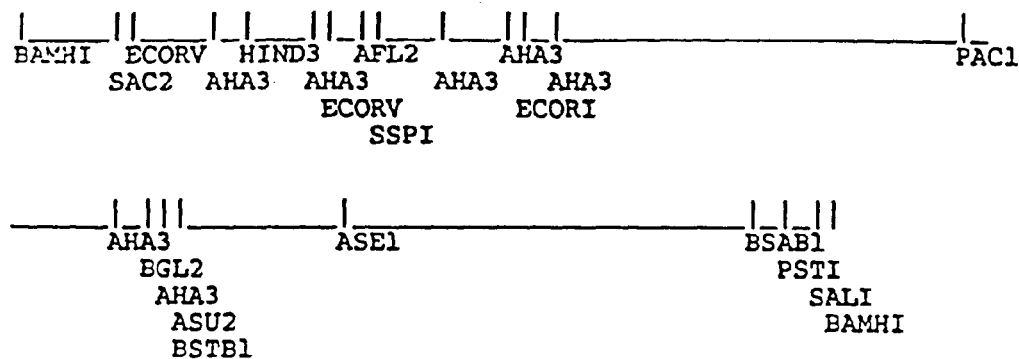

```
                    MetTrpSerTrpLysCysLeuLeuPheTrpAlaValLeuValThrAla
  1  GGATCCACTGGGATGTGGAGCTGGAAGTGCCTCCTCTTCTGGGCTGTCCTGGTCACAGCC
     CCTAGGTGACCCTACACCTCGACCTTCACGGAGGAGAAGACCCGACAGGACCAGTGTCGG
```

1 BAMHI,

```
                    ThrLeuCysThrAlaAlaIleSerValThrMetAspAsnIleLeuSerGlyPheGluAsn
 61  ACACTCTGCACCGCGGCGATATCTGTCACAATGGATAATATCCTCTCAGGATTTGAAAAT
     TGTGAGACGTGGCGCCGCTATAGACAGTGTTACCTATTATAGGAGAGTCCTAAACTTTTA
```

71 SAC2, 78 ECORV,

```
                    GluTyrAspValIleTyrLeuLysProLeuAlaGlyValTyrArgSerLeuLysLysGln
121  GAATATGATGTTATATATTTAAAACCTTTAGCTGGAGTATATAGAAGCTTAAAAAAACAA
     CTTATACTACAATATATAAATTTTGGAAATCGACCTCATATATCTTCGAATTTTTTTGTT
```

138 AHA3, 165 HIND3,

```
                    IleGluLysAsnIlePheThrPheAsnLeuAsnLeuAsnAspIleLeuAsnSerArgLeu
181  ATTGAAAAAAACATTTTTACATTTAATTTAAATTTGAACGATATCTTAAATTCACGTCTT
     TAACTTTTTTTGTAAAAATGTAAATTAAATTTAAACTTGCTATAGAATTTAAGTGCAGAA
```

207 AHA3, 220 ECORV, 238 AFL2,

```
                    LysLysArgLysTyrPheLeuAspValLeuGluSerAspLeuMetGlnPheLysHisIle
241  AAGAAACGAAAATATTTCTTAGATGTATTAGAATCTGATTTAATGCAATTTAAACATATA
     TTCTTTGCTTTTATAAAGAATCTACATAATCTTAGACTAAATTACGTTAAATTTGTATAT
```

251 SSPI, 289 AHA3,

SerSerAsnGluTyrIleIleGluAspSerPheLysLeuLeuAsnSerGluGlnLysAsn

Fig. 7B

```
301 TCCTCAAATGAATACATTATTGAAGATTCATTTAAATTATTGAATTCAGAACAAAAAAAC
    AGGAGTTTACTTATGTAATAACTTCTAAGTAAATTTAATAACTTAAGTCTTGTTTTTTG
```

331 AHA3, 342 ECORI,

```
         ThrLeuLeuLysSerTyrLysTyrIleLysGluSerValGluAsnAspIleLysPheAla
361 ACACTTTTAAAAAGTTACAAATATATAAAAGAATCAGTAGAAAATGATATTAAATTTGCA
    TGTGAAAATTTTTCAATGTTTATATATTTTCTTAGTCATCTTTTACTATAATTTAAACGT
```

366 AHA3,

```
         GlnGluGlyIleSerTyrTyrGluLysValLeuAlaLysTyrLysAspAspLeuGluSer
421 CAGGAAGGTATAAGTTATTATGAAAAGGTTTTAGCGAAATATAAGGATGATTTAGAATCA
    GTCCTTCCATATTCAATAATACTTTTCCAAAATCGCTTTATATTCCTACTAAATCTTAGT
```

```
         IleLysLysValIleLysGluGluLysGluLysPheProSerSerProProThrThrPro
481 ATTAAAAAAGTTATCAAAGAAGAAAAGGAGAAGTTCCCATCATCACCACCAACAACACCT
    TAATTTTTTCAATAGTTTCTTCTTTTCCTCTTCAAGGGTAGTAGTGGTGGTTGTTGTGGA
```

```
         ProSerProAlaLysThrAspGluGlnLysLysGluSerLysPheLeuProPheLeuThr
541 CCGTCACCAGCAAAAACAGACGAACAAAAGAAGGAAAGTAAGTTCCTTCCATTTTTAACA
    GGCAGTGGTCGTTTTTGTCTGCTTGTTTTCTTCCTTTCATTCAAGGAAGGTAAAAATTGT
```

```
         AsnIleGluThrLeuTyrAsnAsnLeuValAsnLysIleAspAspTyrLeuIleAsnLeu
601 AACATTGAGACCTTATACAATAACTTAGTTAATAAAATTGACGATTACTTAATTAACTTA
    TTGTAACTCTGGAATATGTTATTGAATCAATTATTTTAACTGCTAATGAATTAATTGAAT
```

649 PAC1,

```
         LysAlaLysIleAsnAspCysAsnValGluLysAspGluAlaHisValLysIleThrLys
661 AAGGCAAAGATTAACGATTGTAATGTTGAAAAGATGAAGCACATGTTAAAATAACTAAA
    TTCCGTTTCTAATTGCTAACATTACAACTT...CTACTTCGTGTACAATTTTATTGATTT
```

```
         LeuSerAspLeuLysAlaIleAspAspLysIleAspLeuPheLysAsnHisAsnAspPhe
721 CTTAGTGATTTAAAAGCAATTGATGACAAAATAGATCTTTTTAAAAACCATAACGACTTC
    GAATCACTAAATTTTCGTTAACTACTGTTTTATCTAGAAAAATTTTGGTATTGCTGAAG
```

729 AHA3, 753 BGL2, 760 AHA3, 778 ASU2 BSTB1,

```
         GluAlaIleLysLysLeuIleAsnAspAspThrLysLysAspMetLeuGlyLysLeuLeu
781 GAAGCAATTAAAAAATTGATAAATGATGATACGAAAAAAGATATGCTTGGCAAATTACTT
    CTTCGTTAATTTTTTAACTATTTACTACTATGCTTTTTTCTATACGAACCGTTTAATGAA
```

```
         SerThrGlyLeuValGlnAsnPheProAsnThrIleIleSerLysLeuIleGluGlyLys
841 AGTACAGGATTAGTTCAAAATTTTCCTAATACAATAATATCAAAATTAATTGAAGGAAAA
    TCATGTCCTAATCAAGTTTTAAAAGGATTATGTTATTATAGTTTTAATTAACTTCCTTTT
```

885 ASE1,

```
         PheGlnAspMetLeuAsnIleSerGlnHisGlnCysValLysLysGlnCysProGluAsn
901 TTCCAAGATATGTTAAACATTTCACAACACCAATGCGTAAAAAAACAATGTCCAGAAAAT
    AAGGTTCTATACAATTTGTAAAGTGTTGTGGTTACGCATTTTTTTGTTACAGGTCTTTTA
```

```
         SerGlyCysPheArgHisLeuAspGluArgGluGluCysLysCysLeuLeuAsnTyrLys
961 TCTGGATGTTTCAGACATTTAGATGAAAGAGAAGAATGTAAATGTTTATTAAATTACAAA
    AGACCTACAAAGTCTGTAAATCTACTTTCTCTTCTTACATTTACAAATAATTTAATGTTT
```

Fig. 7C

```
       GlnGluGlyAspLysCysValGluAsnProAsnProThrCysAsnGluAsnAsnGlyGly
1021   CAAGAAGGTGATAAATGTGTTGAAAATCCAAATCCTACTTGTAACGAAAATAATGGTGGA
       GTTCTTCCACTATTTACACAACTTTTAGGTTTAGGATGAACATTGCTTTTATTACCACCT

CysAspAlaAspAlaLysCysThrGluGluAspSerGlySerAsnGlyLysLysIleThr
1081   TGTGATGCAGATGCCAAATGTACCGAAGAAGATTCAGGTAGCAACGGAAAGAAAATCACA
       ACACTACGTCTACGGTTTACATGGCTTCTTCTAAGTCCATCGTTGCCTTTCTTTTAGTGT

CysGluCysThrLysProAspSerTyrProLeuPheAspGlyIlePheCysSerAM AM
1141   TGTGAATGTACTAAACCTGATTCTTATCCACTTTTCGATGGTATTTTCTGCAGTTAGTAG
       ACACTTACATGATTTGGACTAAGAATAGGTGAAAAGCTACCATAAAAGACGTCAATCATC

1159 BSAB1, 1188 PSTI, 1200 SALI,

1201   TCGACCCTTGGAAGGATCC
       AGCTGGGAACCTTCCTAGG

1214 BAMHI,

DNA AND AMINO ACID SEQUENCE OF BVp42-M attggatccactaaa

```
 13 atgtggtcttggaagtgtcttttattctgggctgtcttggtgacc
     M  W  S  W  K  C  L  L  F  W  A  V  L  V  T
 58 gccactctttgcacagcagcgatctctgttactatggacaacatc
     A  T  L  C  T  A  A  I  S  V  T  M  D  N  I
103 ctcagtggcttcgagaacgagtacgacgtaatctacctaaagccc
     L  S  G  F  E  N  E  Y  D  V  I  Y  L  K  P
148 cttgccggtgtctaccgttcattgaagaaacagatagaaaagaat
     L  A  G  V  Y  R  S  L  K  K  Q  I  E  K  N
193 attttcacgttcaacctcaacctaaatgacatcctcaactcgcgc
     I  F  T  F  N  L  N  L  N  D  I  L  N  S  R
238 ctcaagaagcgaaaatacttcctcgacgtgttggaatccgacctt
     L  K  K  R  K  Y  F  L  D  V  L  E  S  D  L
283 atgcaatttaagcacattagctctaacgagtacatcatagaggac
     M  Q  F  K  H  I  S  S  N  E  Y  I  I  E  D
328 agcttcaagctcttgaattcagaacagaagaacaccctcctaaag
     S  F  K  L  L  N  S  E  Q  K  N  T  L  L  K
373 tcctacaaatacattaaggagtctgttgagaacgacatcaagttc
     S  Y  K  Y  I  K  E  S  V  E  N  D  I  K  F
418 gcccaggaaggaattagctactatgagaaagtcctggctaaatac
     A  Q  E  G  I  S  Y  Y  E  K  V  L  A  K  Y
463 aaggacgacttggaaagcattaagaaggtaatcaaagaagagaag
     K  D  D  L  E  S  I  K  K  V  I  K  E  E  K
508 gaaaagtttccgagctctccacccacaactcccccatcgcctgca
     E  K  F  P  S  S  P  P  T  T  P  P  S  P  A
553 aagaccgacgagcagaaaaagaaagtaagttccttccattcctc
     K  T  D  E  Q  K  K  E  S  K  F  L  P  F  L
598 accaacatcgaaactctatataacaacctggtgaacaagattgat
     T  N  I  E  T  L  Y  N  N  L  V  N  K  I  D
643 gactacttaatcaacttgaaggcgaaaattaatgactgtaacgtc
     D  Y  L  I  N  L  K  A  K  I  N  D  C  N  V
688 gaaaaggatgaagcccacgttaagatcaccaagctttccgatctc
     E  K  D  E  A  H  V  K  I  T  K  L  S  D  L
733 aaagccatcgacgataagattgacctgtttaagaaccacaacgat
     K  A  I  D  D  K  I  D  L  F  K  N  H  N  D
778 ttcgacgcaatcaaaaagttgatcaacgacgatactaagaaagac
     F  D  A  I  K  K  L  I  N  D  D  T  K  K  D
823 atgcttggaaaactgctgtcgacaggcttggtccaaaacttcccg
     M  L  G  K  L  L  S  T  G  L  V  Q  N  F  P
868 aacaccattataagcaagctgatcgaaggaaagtttcaggatatg
```

Figure 12 Cont.

```
          N  T  I  I  S  K  L  I  E  G  K  F  Q  D  M
    913  ctgaacatctctcagcatcaatgcgtgaagaagcaatgtcccgag
          L  N  I  S  Q  H  Q  C  V  K  K  Q  C  P  E
    958  aattcaggttgcttccgccacttagacgaaagggaggaatgtaaa
          N  S  G  C  F  R  H  L  D  E  R  E  E  C  K
   1003  tgcctgctgaattataaacaggaaggagacaagtgcgtagagaat
          C  L  L  N  Y  K  Q  E  G  D  K  C  V  E  N
   1048  cctaacccaacctgtaacgaaaataacggtggctgcgatgctgac
          P  N  P  T  C  N  E  N  N  G  G  C  D  A  D
   1093  gctaagtgtaccgaggaggacagcggttccaatggcaagaaaata
          A  K  C  T  E  E  D  S  G  S  N  G  K  K  I
   1138  acttgcgaatgcacgaagcccgatagttaccctctcttcgacggt
          T  C  E  C  T  K  P  D  S  Y  P  L  F  D  G
   1183  atcttctgctcc
          I  F  C  S ccacctcatcatcatcatcatcattaataaggtaccta
 P  P  H  H  H  H  H  H  *  *
```

FIGURE 14

DNA AND AMINO ACID SEQUENCE OF P42-K

```
  1 GGATCCCTAAAATGTGGAGCTGGAAGTGCCTCCTCTTCTGGGCTGTCCTG
                 M  W  S  W  K  C  L  L  F  W  A  V  L
 51 GTCACAGCCACACTCTGCACCGCGGGCGCCGCAGTAACTCCTTCCGTAAT
     V  T  A  T  L  C  T  A  G  A  A  V  T  P  S  V  I
101 TGATAACATACTTTCTAAAATTGAAAATGAATATGAGGTTTTATATTTAA
     D  N  I  L  S  K  I  E  N  E  Y  E  V  L  Y  L
151 AACCTTTAGCAGGTGTTTATAGAAGTTTAAAAAAACAATTAGAAAATAAC
     K  P  L  A  G  V  Y  R  S  L  K  K  Q  L  E  N  N
201 GTTATGACATTTAATGTTAATGTTAAGGATATTTTAAATTCACGATTTAA
     V  M  T  F  N  V  N  V  K  D  I  L  N  S  R  F  N
251 TAAACGTGAAAATTTCAAAAATGTTTTAGAATCAGATTTAATTCCATATA
     K  R  E  N  F  K  N  V  L  E  S  D  L  I  P  Y
301 AAGATTTAACATCAAGTAATTATGTTGTCAAAGATCCATATAAATTTCTT
     K  D  L  T  S  S  N  Y  V  V  K  D  P  Y  K  F  L
351 AATAAAGAAAAAGAGATAAATTCTTAAGCAGTTATAATTATATTAAGGA
     N  K  E  K  R  D  K  F  L  S  S  Y  N  Y  I  K  D
401 TTCAATAGATACGGATATAAATTTTGCAAATGATGTTCTTGGATATTATA
        S  I  D  T  D  I  N  F  A  N  D  V  L  G  Y  Y
451 AAATATTATCCGAAAAATATAAATCAGATTTAGATTCAATTAAAAAATAT
     K  I  L  S  E  K  Y  K  S  D  L  D  S  I  K  K  Y
501 ATCAACGACAAACAAGGTGAAAATGAGAAATACCTTCCCTTTTTAAACAA
     I  N  D  K  Q  G  E  N  E  K  Y  L  P  F  L  N  N
551 TATTGAGACCTTATATAAAACAGTTAATGATAAAATTGATTTATTTGTAA
        I  E  T  L  Y  K  T  V  N  D  K  I  D  L  F  V
601 TTCATTTAGAAGCAAAAGTTCTAAATTATACATATGAGAAATCAAACGTA
     I  H  L  E  A  K  V  L  N  Y  T  Y  E  K  S  N  V
651 GAAGTTAAAATAAAAGAACTTAATTACTTAAAAACAATTCAAGACAAATT
     E  V  K  I  K  E  L  N  Y  L  K  T  I  Q  D  K  L
701 GGCAGATTTTAAAAAAAATAACAATTTCGTTGGAATTGCTGATTTATCAA
     A  D  F  K  K  N  N  N  F  V  G  I  A  D  L  S
751 CAGATTATAACCATAATAACTTATTGACAAAGTTCCTTAGTACAGGTATG
     T  D  Y  N  H  N  N  L  L  T  K  F  L  S  T  G  M
```

```
801 GTTTTTGAAAATCTTGCTAAAACCGTTTTATCTAATTTACTTGATGGAAA
     V  F  E  N  L  A  K  T  V  L  S  N  L  L  D  G  N
851 CTTGCAAGGTATGTTAAACATTTCACAACACCAATGCGTAAAAAAACAAT
     L  Q  G  M  L  N  I  S  Q  H  Q  C  V  K  K  Q
901 GTCCACAAAATTCTGGATGTTTCAGACATTTAGATGAAAGAGAAGAATGT
     C  P  Q  N  S  G  C  F  R  H  L  D  E  R  E  E  C
951 AAATGTTTATTAAATTACAAACAAGAAGGTGATAAATGTGTTGAAAATCC
     K  C  L  L  N  Y  K  Q  E  G  D  K  C  V  E  N  P
1001 AAATCCTACTTGTAACGAAAATAATGGTGGATGTGATGCAGATGCCAAAT
      N  P  T  C  N  E  N  N  G  G  C  D  A  D  A  K
1051 GTACCGAAGAAGATTCAGGTAGCAACGGAAAGAAAATCACATGTGAATGT
      C  T  E  E  D  S  G  S  N  G  K  K  I  T  C  E  C
1101 ACTAAACCTGATTCTTATCCACTTTTCGATGGTATTTTCTGCAGTCATCA
      T  K  P  D  S  Y  P  L  F  D  G  I  F  C  S  H  H
1151 TCATCATCATCATTAATAAGGTACC
      H  H  H  H  *  *
```

Underlined sequences represent restriction sites.
Bold letters represent alterations done to the leader sequence as described in the methods.
The boxed letter represents the original sequence where a mis-sense mutation to a cytosine occurred.
"*" represent stop codons.

Figure 14 Cont.

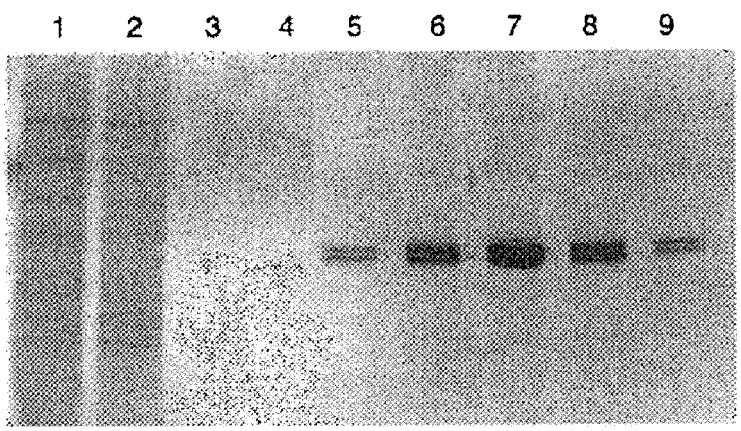
FIG._15
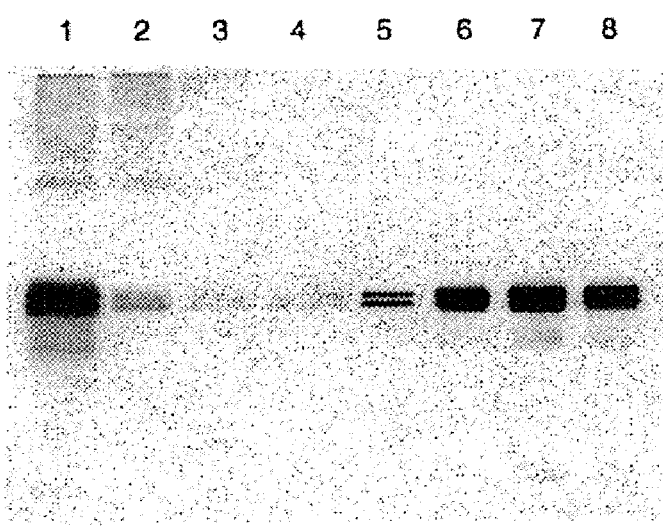
FIG._16
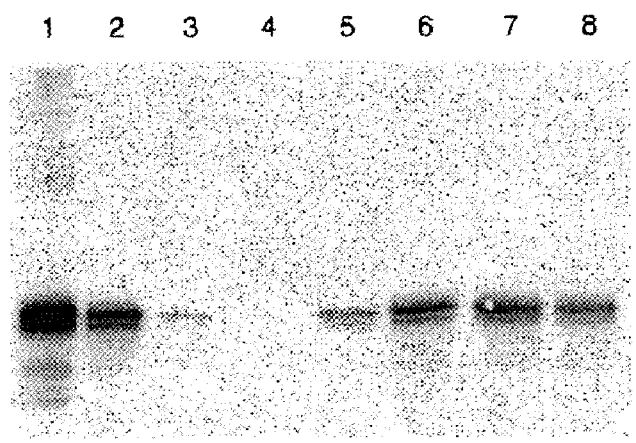
FIG._17

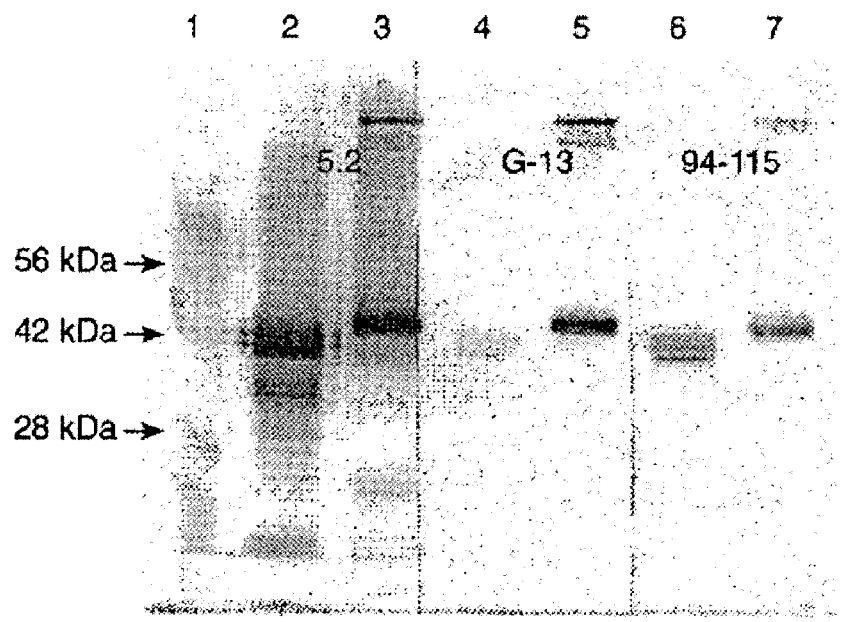
FIG._18A
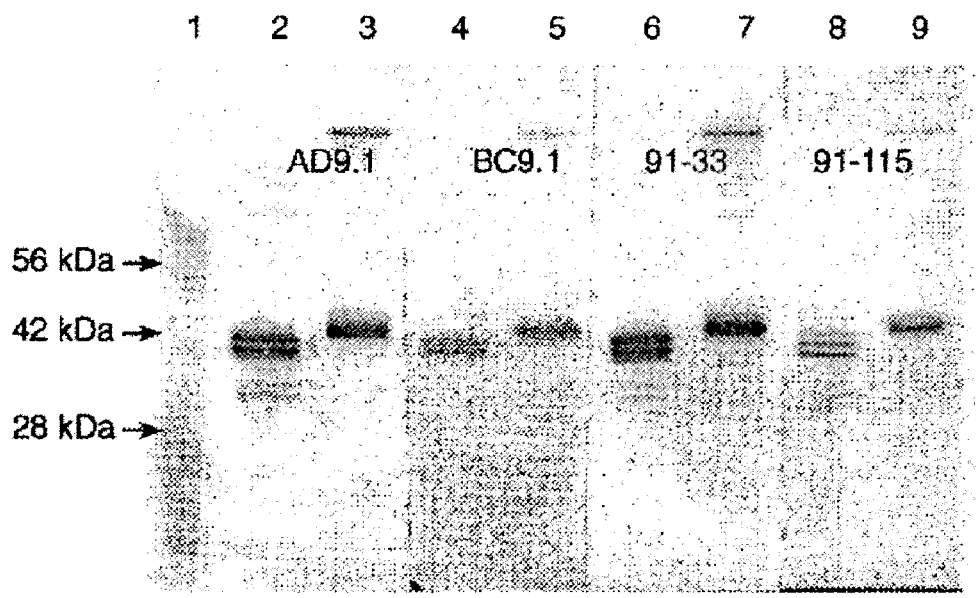
FIG._18B

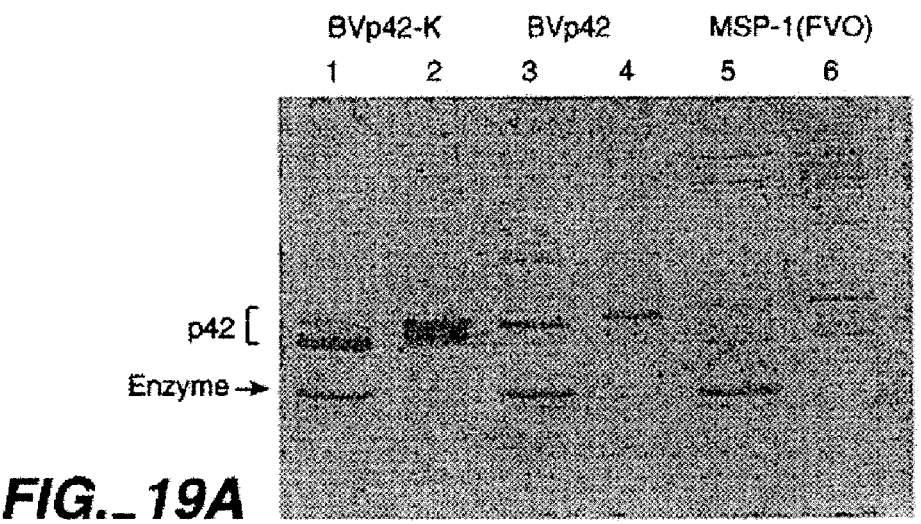
*FIG._19A*
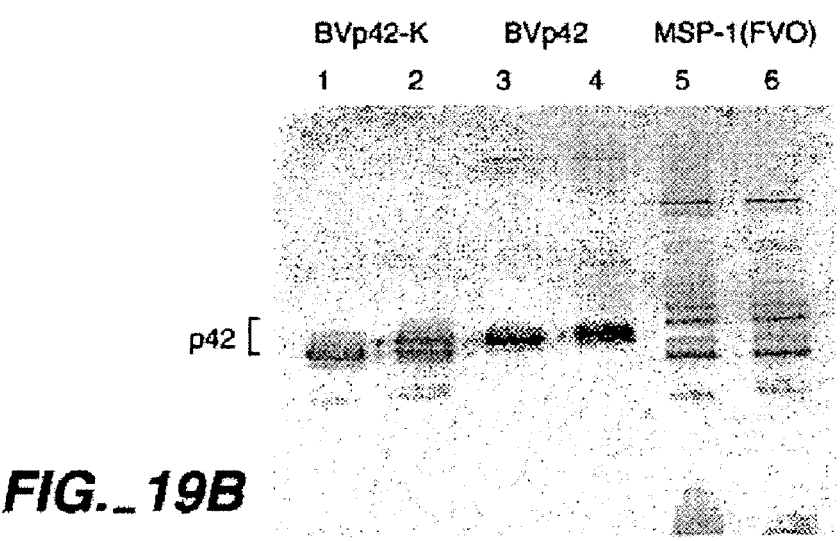
*FIG._19B*
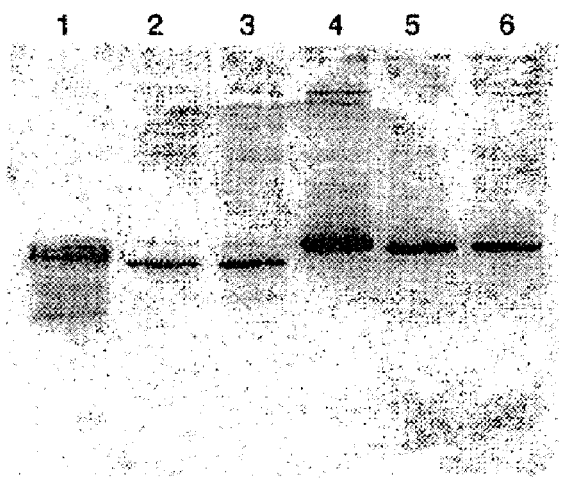
*FIG._20*

FIGURE 23A
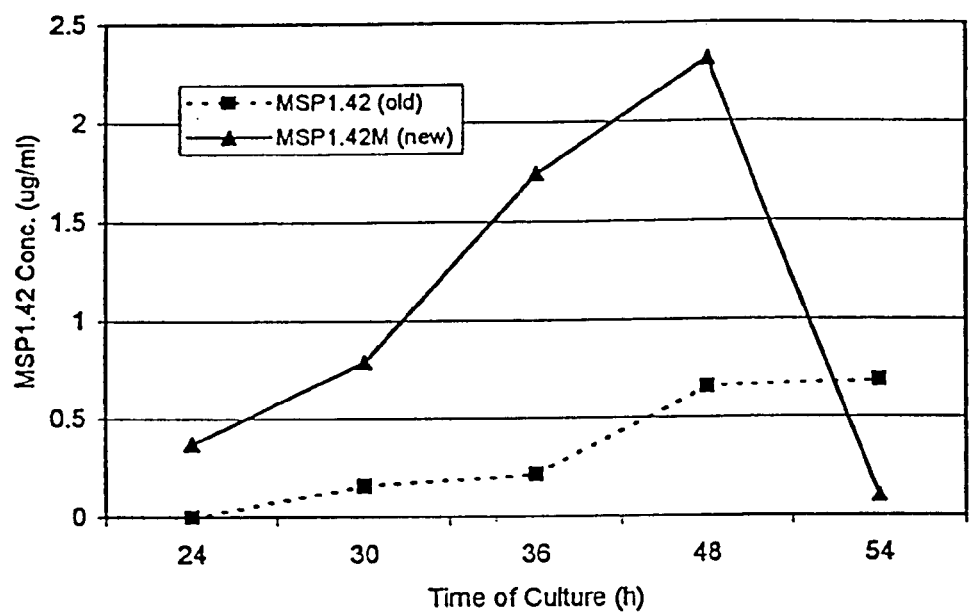
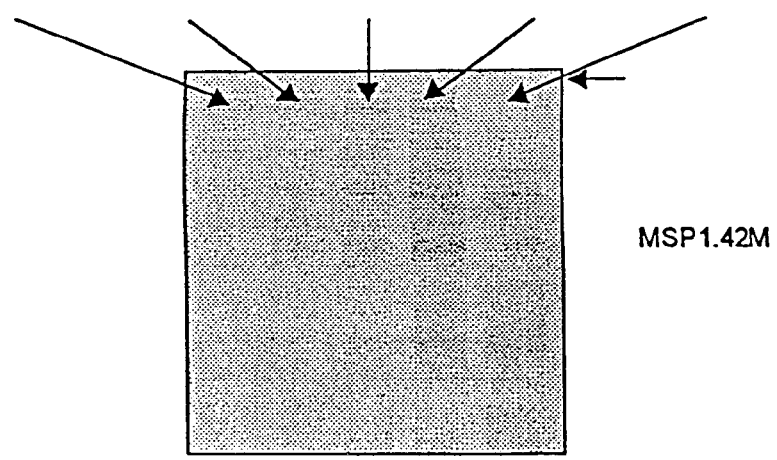
FIGURE 23B

← 42 kDa

| LANE NO. | |
|---|---|
| 1 | MW MARKERS |
| 2 | COLUMN 1 ELUATE ("PARTIALLY-PURIFIED MSP1.42") |
| 3 | COLUMN 2 EFFLUENT, FRACTION #1 |
| 4 | COLUMN 2 EFFLUENT, FRACTION #2 |
| 5 | COLUMN 2 ELUATE, BUFFER A FRACTION #1 |
| 6 | COLUMN 2 ELUATE, BUFFER A FRACTION #2 |
| 7 | COLUMN 2 ELUATE, BUFFER B FRACTION #1 |
| 8 | COLUMN 2 ELUATE, BUFFER B FRACTION #2 ("PURIFIED MSP1.42") |
| 9 | COLUMN 2 ELUATE, BUFFER B FRACTION #3 |

PLASMODIUM FALCIPARUM POLYPEPTIDES AND METHODS OF USING SAME

This application is a division of application Ser. No. 10/062,809, filed Feb. 1, 2002 (now abandoned), which claims the benefit of provisional Application Ser. No. 60/266,281, filed Feb. 1, 2001; and which also is a continuation-in-part of application Ser. No. 09/500,376, filed Feb. 8, 2000, now U.S. Pat. No. 6,855,316, the disclosures of which are expressly incorporated by reference herein.

FIELD OF THE INVENTION

This invention is in the field of recombinant *Plasmodium falciparum* polypeptides, vaccines, and vaccine formulations.

BACKGROUND OF THE INVENTION

The major merozoite surface protein of *Plasmodium* species has been shown to be a target of varying degrees of protective immunity against the asexual blood stages in rodent and human malaria. For example, vaccination of mice with purified P230, the major merozoite surface protein of the rodent malaria *Plasmodium yoelii*, has resulted in reduced parasitemias in comparison to controls upon intravenous challenge with a lethal dose of parasitized erythrocytes (Holder et al. 1981. Nature 294:361). Mice have also been protected against *P. yoelii* by passive transfer of a monoclonal antibody (Mab) specific for P230 (Majarian et al. 1984. J. Immunol. 132:3131) and against (rodent malaria) *Plasmodium chabaudi adami* challenge by passive immunization with a Mab specific for the homologous 250-kDa molecule of this *plasmodium* species (Lew et al. 1989. Proc. Natl. Acad. Sci. USA 86:3768). The ability to confer resistance to parasite challenge by passive transfer of antibodies suggests that antibody-mediated mechanisms play an important role in antigen-specific immunity to malaria.

Despite these findings, however, no commercially viable vaccine has been developed against the major merozoite surface antigen of the major human malaria pathogen, *Plasmodium falciparum*.

For example, using naturally derived materials, such as the precursor of the major merozoite surface protein (MSP) alone (gp195: 195,000-200,000 Da molecular species; merozoite surface protein-1 (MSP-1)), gp195 mixed with certain of its natural processing fragments, or a natural processing fragment by itself, partial protection against *Plasmodium falciparum* infection has been achieved by some researchers (Hall et al. 1984. Nature 311:379; Perrin et al. 1984. J. Exp. Med. 160:441; Patarroyo et al. 1987. Vaccines 87 (Brown, Chanock, Lerner, ed.) Cold Spring Harbor Laboratory Press, CSH, NY. 117-124). An effective vaccine against *Plasmodium falciparum* should not convey merely partial protection, i.e. a partial lowering of parasitemia, since even low parasitemias of this organism cause serious illness. A commercially useful vaccine should substantially eliminate parasitemia. It is generally thought that an acceptable malaria vaccine that would reduce parasitemia to a low level and, consequently, result in a substantial reduction in morbidity and mortality.

In one instance, substantially complete protection using natural materials against *Plasmodium falciparum* challenge has been achieved in *Aotus* monkeys, in particular by the use of a mixture of gp195 and some of its natural processing fragments obtained by affinity purification using a Mab, designated Mab 5.2 (Siddiqui et al. 1987. Proc. Natl. Acad. Sci. USA 84:3014). In follow up experiments using Mab 5.2 affinity purified, parasite gp195, a correlation was found between protection against infection with *Plasmodium falciparum* and the ability of serum antibodies to strongly inhibit parasite growth in vitro. In particular, monkeys and rabbits hyperimmunized with Mab 5.2 affinity purified parasite gp 195 in complete Freund's adjuvant produced antibodies that inhibited in vitro parasite growth (Hui et al. 1987. Exp. Parasitol. 64:519).

The difficulty in developing an effective naturally derived vaccine, however, has been compounded with the difficulty in developing an effective recombinant or synthetic vaccine. Recombinant or synthetic vaccines are desirable for several reasons. They have the potential to focus immune response(s) on the most effective portion of gp 195, an important advantage since there may be decoy determinants in gp 195 which prevent the most effective response. Also, more homogeneous preparations are possible using recombinant techniques than in preparations of naturally derived products. In addition, recombinant and synthetic based vaccines avoid the potential contamination of naturally derived gp195 with pathogens from its human source.

Although a number of investigators have designed and tested gp195-based synthetic peptides and recombinant products as vaccine antigens, no strongly protective vaccine has resulted. Thus, synthetic peptides corresponding to various segments of the N-terminal 83 kDa processing fragment of gp195 induced antibodies in rabbits which displayed only a low level of cross reactivity with asexual blood stage parasites (Cheung et al. 1986. Proc. Natl. Acad. Sci. USA 83:8328). One of these synthetic peptides, corresponding to a non-repetitive, conserved sequence, partially protected *Saimiri* monkeys against *Plasmodium falciparum* challenge (Cheung et al. 1986). In a vaccination study in *Aotus* monkeys using an 83 kDa processing fragment-based recombinant polypeptide produced in *E. coli* there was no significant difference between the course of infection of control animals and animals immunized with the recombinant polypeptide. In addition, very low levels of antibodies cross-reactive with native gp 195 by immunofluorescence were induced (Knapp et al. 1988. Behring Inst. Mitt. 82:349). A bacterial recombinant polypeptide based on a fusion of two conserved regions located towards the amino terminus and center of the gp195 molecule induced only low indirect fluorescent antibody (IFA) titers when used to immunize *Aotus* monkeys (Herrera et al. 1990. Proc. Natl. Acad. Sci. USA 87:4017) and two out of five immunized animals were partially protected.

Holder et al. studied two recombinant polypeptides which corresponded to portions of the 42 kDa C-terminal processing fragment of gp195 (p42) fused to trp E and beta-galactosidase carrier sequences, respectively (Holder et al. 1988. Parasite. Immunol. 10:607). While immunized animals produced high antibody titers against the carrier portion of the recombinant polypeptides, much lower titers were detected against the gp 195 antigen. Some of the *Aotus* monkeys immunized with both of these recombinant polypeptides were partially protected against parasite challenge.

Murphy et al. (1990. Parasitology. 2:177-183) attempted to recombinantly produce portions of the p42 antigen of the Wellcome isolate of gp195 in insect host cells. gp95 is believed to exist in at least two allelic forms, of which the Wellcome isolate ("Wellcome allele") and the MAD isolate ("MAD allele") are representative (Tanabe et al. 1987. J. Mol. Biol. 195:273). While Murphy et al. reported producing a product which folded in a similar manner to the natural antigen, they did not report obtaining a purified polypeptide but only reported multiply banded antigens speculated to have resulted from post-translational processing or degradation. No follow-up immunogenicity or efficacy studies have been reported using any materials obtained.

A mixture of three synthetic peptides, one peptide from the 83 kDa processing fragment of gp195 and two non-gp195 malaria peptides, partially to completely protected monkeys against parasite challenge; a hybrid synthetic polymer including the sequences of the three synthetic peptides in addition to a circumsporozoite region was reported to provide a delay or suppression of parasitemias (Patarroyo et al. 1987. Nature 328:629; Rodriguez et al. 1990. Am. J. Trop. Med. Hyg. 43:339; Patarroyo et al. 1988. Nature 332:158). Field trials of this hybrid are under way. It is unclear whether any gp 195 epitopes in the mixture or hybrid resulted in any protection. In addition there have been two reported studies which were unable to duplicate the prior results obtained using the peptide mixture (Reubush et al. 1990. Am. J. Trop. Med. Hyg. 43:355-366) or the hybrid peptide multimer (Herrera et al. 1991. Abstract in the IV International Congress on Malaria and Babesiosis). Thus, there has been no gp195-based recombinant or synthetic vaccine antigen which has been shown sufficiently effective against *Plasmodium falciparum* challenge.

Accordingly, it is an object of the invention to provide recombinant or synthetic antigens, compositions comprising these antigens, and methods of use that are effective against *Plasmodium falciparum* challenge.

SUMMARY OF THE INVENTION

In accordance with these objectives, the present invention provides a composition comprising a malarial polypeptide expressed by an insect cell which contains a vector encoding the malarial polypeptide that is immunogenic in a mammalian host.

In another aspect, the invention provides a composition comprising a malarial polypeptide and an adjuvant.

In a further aspect, the invention provides methods of inducing an anti-*plasmodium* immune response in a primate. The immune response preferably substantially reduces parasitemia in a *plasmodium*-infected primate.

In a yet another aspect, the invention provides methods of making an anti-*plasmodium* immunogen.

BRIEF DESCRIPTION OF THE DRAWINGS

FIGS. 1A-B are schematic representations of a baculovirus p42 gene construct. In FIG. 1A the structure of baculovirus p42 consists of the flg5 leader sequence (flg$_L$, solid box) fused to the p42 coding region from amino acids Ala$_{1333}$ to Ser$_{1705}$. In FIG. 1B synthetic DNA (solid boxes) encodes the flg5 leader and 5' region of p42 as a BamHI(B)/HindIII fragment. A synthetic PstI(P)/SalI(L) linker encodes the termination codon (solid box) at the 3' end of the construct. The HindIII/PstI fragment was derived from cloned parasite DNA.

FIGS. 2A-B depict silver stains (lane 1) and immunoblots (lane 2) of BVp42 (FIG. 2A) and Yp42 (FIG. 2B) electrophoresed in a 10% SDS-polyacrylamide gel. Immunoblots were reacted with rabbit anti-parasite gp195.

FIGS. 3A-B show immunoblots of purified parasite gp 195 electrophoresed under nonreducing (FIG. 3A) or reducing (FIG. 3B) conditions and reacted with anti-gp195 Mab 5.2 (lane 1); rabbit anti-parasite gp195 (lane 2); rabbit anti-BVp42; (#131, lane 3 and #132, lane 4); rabbit anti-Yp42 (#93, lane 5 and #96, lane 6). FIG. 3C shows immunoblots of BVp42 (lane 1, non-reduced; lane 2, reduced) and Yp42 (lane 3, non-reduced: lane 4, reduced) reacted with Mab 5.2.

FIGS. 4A-C are graphs depicting a competition ELISA using purified, parasite gp195 coated plates and BVp42 and gp195 inhibitors.

FIG. 6 shows amino acid sequences of FUP isolate p42 (SEQ ID NO:2) and of the corresponding MAD (SEQ ID NO:3), K1 (SEQ ID NO:4) and Wellcome strains (SEQ ID NO:5). Amino acids shown in the MAD, K1 and Wellcome strains are those that are different from those of the FUP strain. Deletions are shown by a period. Also indicated are the sites for post-translational modification (conserved potential N-glycosylation sites are shown as filled diamonds and non-conserved sites by open diamonds; conserved cysteines are shown by filled circles and non-conserved by open circles) and the beginning of the putative transmembrane region is indicated by the arrow. Number of amino acids is according to Chang et al. 1988. Exp. Parasitol. 67:1.

FIGS. 7A-C show the nucleic acid sequence of the original BVp42 construct (SEQ ID NO: 1) described in Example 1. The construct codes for a flg5 leader polypeptide adjacent to amino acids 1333 to 1705 of the FUP isolate gp195, as those amino acids are numbered in FIG. 6.

FIG. 8A: BVp42/MF59 (Group I); FIG. 8B: BVp42/MTP-PE+MF59 (Group II); FIG. 8C: BVp42/QS21 (Group III); FIG. 8D: BVp42/ISA51 (Group IV).

FIG. 11A: BVp42/MF59; FIG. 11B: BVp42/QS21; FIG. 11C: BVp42/MTP-PE+MF59; FIG. 11D: BVp42/ISA51.

FIG. 12 shows the nucleotide sequence of the p42-M construct modified for optimized insect cell line expression comprising nucleotides 1-1235 of SEQ ID NO:6, its deduced amino acid sequence comprising amino acids 1-402 of SEQ ID NO: 16, the nucleotide sequence of the p42-M (SEQ ID NO:6) construct in which the 18 nucleotides encoding the histidine tail have been removed comprising nucleotides 1-1203 of SEQ ID NO: 17 (p42-M.2) and its deduced amino acid sequence comprising amino acids 1-396 of SEQ ID NO:18.

FIG. 14 shows the DNA sequence of BVp42-K (SEQ ID NO:7) and deduced amino acid sequence (SEQ ID NO:8).

FIG. 15 shows a silver stain of affinity chromatography purified BVp42-K. Lane 1: starting material; Lane 2: column filtrate; Lane 3: binding buffer flow through; Lane 4: washing buffer flow through; Lanes 5-9: purified protein aliquots 3-7. Samples were electrophoresed on an 11.5% polyacrylamide gel.

FIG. 16 shows a western blot of affinity chromatography purified BVp42-K. Lane 1: starting material; Lane 2: column filtrate; Lane 3: binding buffer flow through; Lane 4: washing buffer flow through; Lanes 5-8: purified protein aliquots 3-6. Samples were electrophoresed on an 11.5% polyacrylamide gel.

FIG. 17 shows a western blot of phenyl HIC and Ni-NTA chromatography purified BVp42-K. Lane 1: pooled staring material after phenyl HIC chromatography; Lane 2: column filtrate; Lane 3 is washing buffer flow through; Lanes 4-8: purified protein aliquots 3-7. Samples were electrophoresed on an 11.5% polyacrylamide gel.

FIGS. 18A and 18B show western blots of various Mabs with BVp42 (MAD20 allele) and BVp42-K (K1 allele). Numbers and letters above the lanes correspond to the specific monoclonal antibody used. Panel A: Lane 1: benchmark ladder; Lanes 2, 4, 6: BVp42-K; Lanes 3, 5, 7: BVp42. Panel B: Lane 1: benchmark ladder; Lanes 2, 4, 6, 8: BVp42-K; Lanes 3, 5, 7, 9: BVp42. Samples were electrophoresed on an 11.5% polyacrylamide gel.

FIGS. 19A and 19B show the results of N-glycosidase F digestions of BVp42-K, BVp42, and FVO MSP-1. All samples were electrophoresed on an 11.5% polyacrylamide gel.

Panel A: silver stained gel: Lanes 1-2: BVp42-K; Lanes 3-4: BVp42; Lanes 5-6: FVO MSP-1. Lanes 1, 3, 5 were digested with 0.1 units of N-glycosidase F. Lanes 2, 4, 6 are controls. Samples were electrophoresed on an 11.5% polyacrylamide gel. Panel B: western blot: Lanes 1-2: BVp42-K; Lanes 3-4: BVp42; Lanes 5-6: FVO MSP-1. Lanes 1, 3, 5 were digested with 0.1 units of N-glycosidase F. Lanes 2, 4, 6 are controls.

FIG. 20 shows a western blot of recombinant baculovirus infected insect cell supernatants incubated with tunicamycin. Lanes 1-3: BVp42-K; Lanes 4-6: BVp42. Lanes 1 and 4 are control wells without tunicamycin. Lanes 2 and 5 contain 2.5 µg/ml tunicamycin. Lanes 3 and 6 contain 5 µg/ml tunicamycin. Aliquots of cell supernatants were taken at 55 hours post-infection and electrophoresed on an 11.5% polyacrylamide gel.

Figure 21:
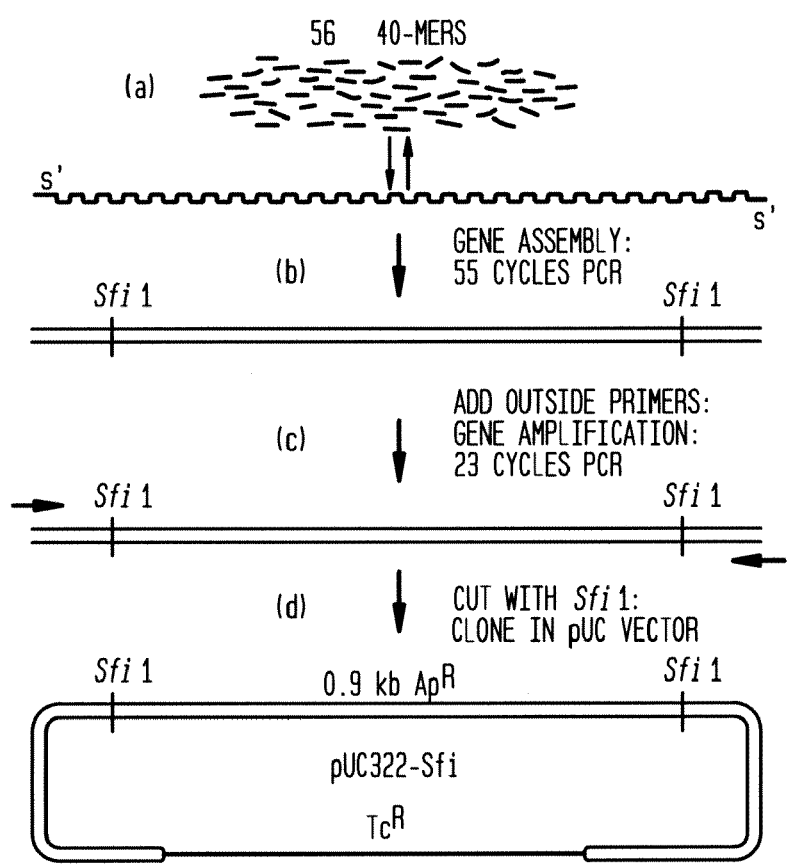

FIG. 21 depicts the general protocol for gene synthesis by PCR gene assembly. (a) overlapping 40-mer oligonucleotides encompassing the region of interest are synthesized using standard phosphoramidite chemistry, (b) gene assembly PCR with equal concentration of each oligonucleotide, heat-stable DNA polymerase, PCR mix (55 cycles), (c) gene amplification with 40-fold dilution of gene assembly product with heat stable DNA polymerase, 2 outside primers (23 cycles), (d) purification and restriction digestion of PCR DNA fragment product, cloning of DNA fragment into suitable plasmid vector using T4 DNA ligase, and transformation into E. coli host cells (adapted from Stemmer et al., Gene 164:49-53, 1995).

Figure 22:
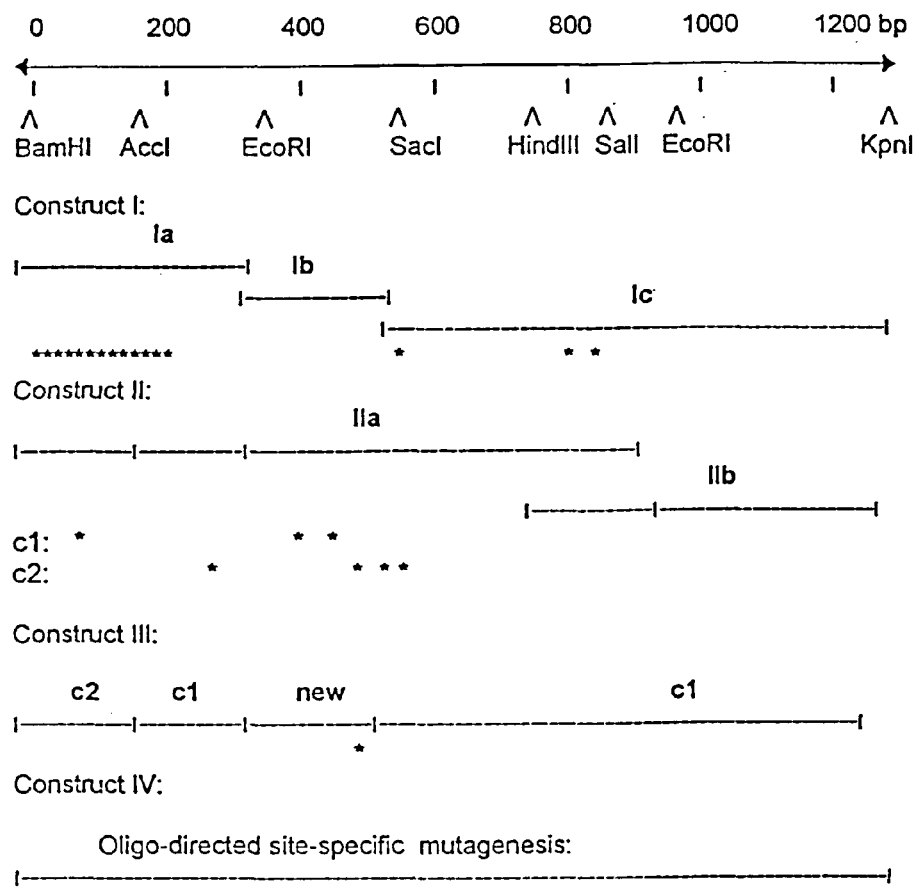

FIG. 22 depicts the restriction enzyme map of reconstructed Positions of restriction endonuclease cleavage sites are indicated with arrowheads. Regions of nucleotide errors discovered in the nucleotide sequence of each construct are indicated as asterisks.

Construct I was generated from three PCR assembled fragments: Ia, Ib, and Ic. Two clones of Construct II (c1 and c2) were generated from PCR assembled fragments IIa and IIb. Construct III was produced from restriction fragments of c1 and c2 and a new PCR assembled fragment Construct IV was produced by oligonucleotide-directed site specific mutagenesis of construct III to yield the correct nucleotide sequence for the entire p42-C6His (p42-M) gene.

FIGS. 23A and 23B depict the kinetics of protein expression of the original BVp42 construct and the new BVp42-M construct. MOI=1.5 for both constructs. FIG. 23A shows capture ELISA quantitation of p42/p42-M polypeptide in crude, culture supernatants. FIG. 23B shows Coomassie blue staining of SDS-PAGE of crude, culture supernatants of p42-M polypeptide.

Figure 24:
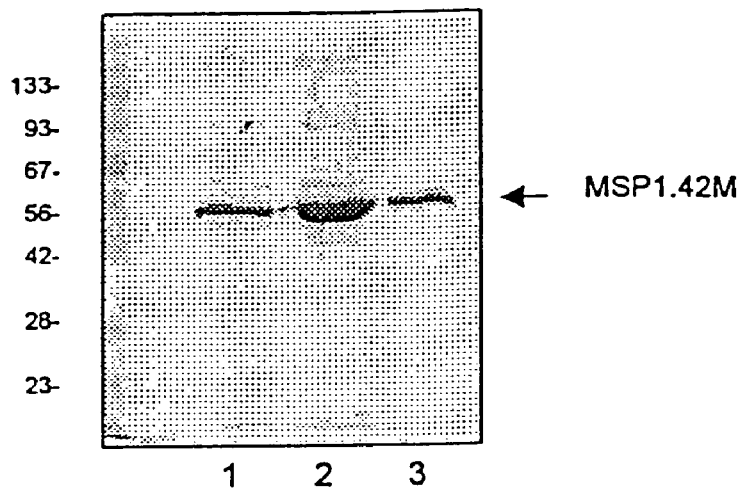

FIG. 24 shows Coomassie stain of p42-M.2 protein (hexa-histidine tag deleted) purified from 75 ml of culture supernatant by monoclonal antibody affinity chromatography.

Lanes 1, 2, and 3 correspond to three peak column fractions. The total purified p42-M.2 protein yield for the three peak tubes was approximately 500 µg, corresponding to a protein yield of 7 mg per liter of culture supernatant.

Figure 25:
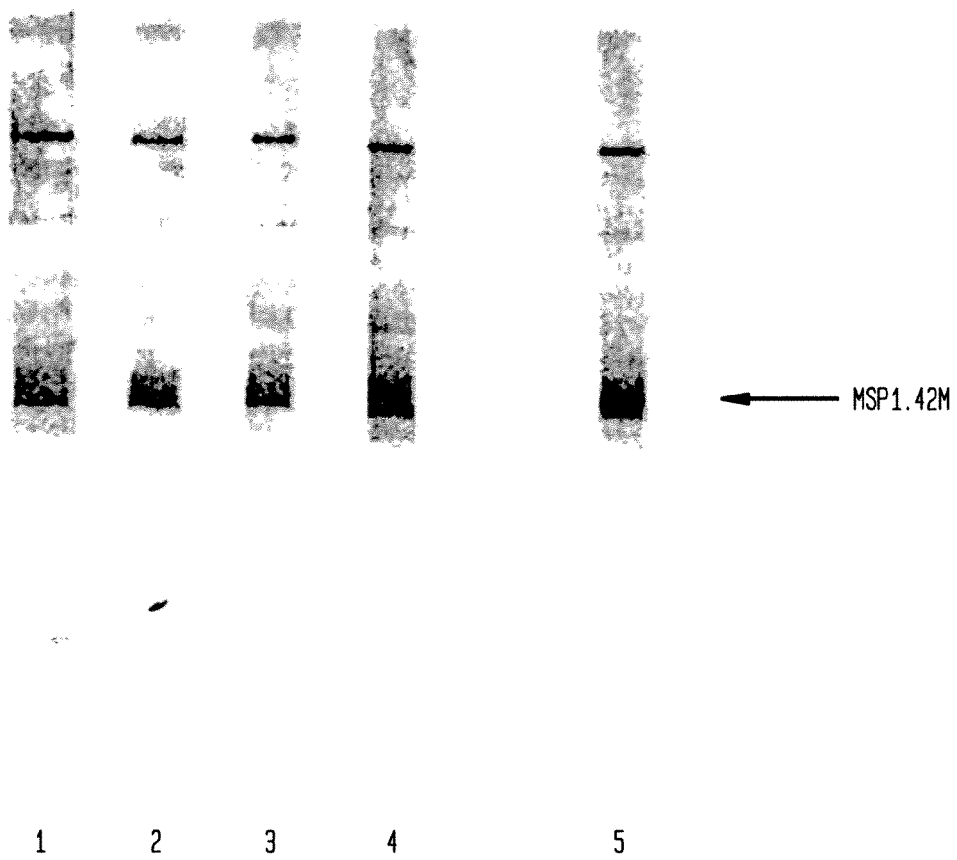

FIG. 25 shows an immunoblot of purified p42-M.2 protein (hexa-histidine tag deleted) with monoclonal antibodies specific for disulfide-dependent, conformational determinants of native p42 (MSP 1.42) (lanes 1-4) and a polyclonal antiserum against the original recombinant p42 encoded by BVp42. Lanes 1, 5.2; 2, G13; 3, AD9.1; 4, G14(S.L.) and 5, polyclonal rabbit anti-MSP 1.42.

FIG. 26 shows Coomassie blue staining of SDS-PAGE of p42-M.2 (hexa-histidine tag deleted) polypeptide material at various stages during chromatography. Column 1: Phenyl Sepharose. Column 2: Cibachron Blue Sepharose.

FIG. 27 shows the codon preferences for the nucleotide sequence of the p42-M and p42-M.2 (hexa-histidine tag deleted) constructs modified for optimized insect cell line *Trichoplusia ni* (HIGH FIVE™) expression.

DETAILED DESCRIPTION OF THE INVENTION

BVp42 antigen of *Plasmodium falciparum* gp195 induces antibodies that strongly, if not substantially completely, inhibit parasite growth and forms the basis of a vaccine. The antibodies are extensively crossreactive with different parasite strains, and have been found to strongly or completely inhibit parasite growth of heterologous parasites to the same degree as homologous parasites. BVp42, as described herein, is a variant of the natural p42 processing fragment of gp195 that has been recombinantly expressed in insect cells using a baculovirus expression vector. The term "BVp42" as used herein to refer to the p42 amino acid sequence as characteristically produced in insect cells, in particular in sf9 insect cells or HIGH FIVE™/BTI-TN-5B1-4 cells. The amino acid sequence of p42 of different isolates is shown in FIG. 6, i.e. amino acids nos. 1333 to 1726 in the FUP isolate, 1308 to 1701 in the MAD isolate, 1264 to 1640 in the Wellcome isolate, and 1255 to 1631 in the K1 isolate (the numbers refer to the amino acids of the precursor molecule, gp195). The term "p42" as used herein refers to the corresponding sequences in other isolates as well. A preferred embodiment of the invention includes only the amino acids $Ala_{1333}$ to $Ser_{1705}$ of the FUP isolate (Chang et al. Exp. Parasitol. 67:1), or the corresponding amino acids of other isolates (e.g. $Ala_{1308}$ to $Ser_{1680}$ of the MAD isolate (Mackay et al. 1985. EMBO J. 4:3823-3829), $Ala_{1264}$ to $Ser_{1619}$ of the Wellcome isolate (Holder et al. 1985. Nature 317:270-273), $Ala_{1255}$ to $Ser_{1610}$ of the K1 isolate (Mackay et al. 1984. EMBO J. 4:3823-3829). (The numbering of these amino acids also corresponds to that shown in FIG. 6.) The antigen of this embodiment preferably deletes the anchor sequence at the C-terminus of p42, allowing easier recovery of the product because it is secreted from the host cells.

The amino acid sequences of isolates bearing the same designation may vary somewhat, as may the DNA sequences coding for those isolates. Similarly, the numberings of the amino acid and DNA sequences in other publications may differ from the numberings shown herein. These and other aspects of the invention are more fully described below. For example, a particular amino acid and DNA sequence of a FUP isolate corresponding to amino acids $Ala_{1333}$ to $Ser_{1705}$ (SEQ ID NO:2) (as shown in FIG. 6) is described in the examples below and has the sequences shown in FIG. 7 (SEQ ID NO: 1).

Accordingly, by "p42 polypeptide" herein is meant a polypeptide comprising a p42 amino acid sequence, including fragments and variants thereof, of the *Plasmodium* major merozoite surface protein (gp195). The p42-M polypeptide is included within the definition of a p42 polypeptide and comprises a p42 polypeptide encoded by a p42-M nucleic acid sequence (see e.g., SEQ ID NO: 6) which differs from the p42 nucleic acids (see e.g., SEQ ID NO: 1). The "p42-M nucleic acid" comprises a nucleic acid in which one or more codons have been substituted with codons encoding the same or similar amino acid (see e.g., the amino substitutions as described herein) wherein the p42-M mRNA transcript is preferentially recognized by the tRNAs present in the insect host cell expression system (see, e.g., FIG. 27 which discloses the codons preferentially used by insect host cell *Trichoplusia ni*). One p42-M amino acid sequence, as set forth in SEQ ID NO: 16, differs from the amino acid sequence encoded by the p42 nucleic acid sequence set forth in FIG. 7, by a single residue at position 257. The p42-M.2 polypeptide is further included within the definition of a p42 polypeptide and comprises a p42 polypeptide encoded by a p42-M.2 nucleic acid (see e.g., SEQ ID NO: 17) wherein the histidine tail of p42 or p42-M has been deleted (see e.g., amino acid residues 1-392 of SEQ ID NO: 18).

By "polypeptide" and grammatical equivalents herein are meant proteins, oligopeptides, and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. In some embodiments, for example when the p42 polypeptides are made synthetically, it may be desirable to utilize protein analogs to retard degradation by sample contaminants.

In a preferred embodiment, the p42 polypeptide is isolated. By "isolated polypeptide" herein is meant a polypeptide which has been identified and separated and/or recovered from a component of its natural environment. Contaminant components of its natural environment are materials which would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least about 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated p42 polypeptide includes the p42 polypeptide expressed by recombinant cells since at least one component of the polypeptide's natural environment will not be present. Ordinarily, however, isolated p42 polypeptide will be prepared by at least one purification step.

In a preferred embodiment, a p42 polypeptide comprises a native sequence p42-polypeptide. A "native sequence" p42 polypeptide comprises a polypeptide having the same amino acid sequence as a p42 polypeptide derived from nature. The term "native sequence" specifically encompasses naturally-occurring truncated or secreted forms (e.g., an extracellular domain sequence), naturally-occurring variant forms (e.g., alternatively spliced forms) and naturally-occurring allelic variants and naturally-occurring *Plasmodium* species variants. In one embodiment of the invention, the native sequence p42 is a mature or full-length native sequence p42 polypeptide.

The p42 "extracellular domain" refers to a form of the p42 polypeptide which is essentially free of the transmembrane (Haldar et al. 1985. J. Biol. Chem. 260(8):4969-4974) and cytoplasmic domains. Ordinarily, a p42 polypeptide extracellular domain will have less than about 1% of such transmembrane and/or cytoplasmic domains and preferably, will have less than about 0.5% of such domains. It will be understood that any transmembrane domain(s) identified for the p42 polypeptides of the present invention are identified pursuant to criteria routinely employed in the art to identify that type of hydrophobic domain. In a preferred embodiment the transmembrane domain is identified as that portion of the p42 polypeptide that anchors the p42 polypeptide to a membrane. In an alternative embodiment, in the absence of the transmembrane domain, the p42 polypeptide is not anchored to a membrane and is therefore not associated with the cell in which the p42 polypeptide is expressed. Accordingly, in a preferred embodiment the p42 polypeptide extracellular domain comprises amino acids from about $Ala_{1333}$ to about $Ser_{1705}$ of the FUP isolate (SEQ ID NO:2) (Chang et al. Exp. Parasitol. 67:1), or the corresponding amino acids of other isolates (e.g. $Ala_{1308}$ to $Ser_{1680}$ of the MAD isolate (SEQ ID NO:4) (Mackay et al. 1985. EMBO J. 4:3823-3829), $Ala_{1264}$ to $Ser_{1619}$ of the Wellcome isolate (SEQ ID NO:5) (Holder et al. 1985. Nature 317:270-273), $Ala_{1255}$ to $Ser_{1610}$ of the K1 isolate (SEQ ID NO:3) (Mackay et al. 1984. EMBO J. 4:3823-3829).

In one embodiment, p42 polypeptides are identified by having substantial amino acid sequence homology with the amino acid sequences provided herein. In another embodiment, p42 polypeptide is identified as being encoded by a nucleic acid having substantial nucleic acid sequence homology with the nucleic acid sequences that are provided herein or with the nucleic acid sequences that encode the amino acid sequences provided herein. By "homology" herein is meant sequence similarity and identity with identity being preferred. Such sequence identity or similarity can be based upon the overall amino acid or nucleic acid sequence.

In a preferred embodiment, a polypeptide is a p42 polypeptide as defined herein if the overall sequence identity of the amino acid sequences of FIG. 6 is preferably greater than about 60%, more preferably greater than about 70%, even more preferably greater than about 80% and most preferably greater than 90%. In some embodiments the sequence identity will be as high as about 93 to 95 or 98%.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman. 1981. Adv. Appl. Math. 2:482, which is expressly incorporated by reference, by the sequence identity alignment algorithm of Needleman & Wunsch. 1970. J. Mol. Biol. 48:443, which is expressly incorporated by reference, by the search for similarity method of Pearson & Lipman. 1988. PNAS USA 85:2444, which is expressly incorporated by reference, by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. 1984. Nucl. Acid Res. 12:387-395, all of which are expressly incorporated by reference, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc., which is expressly incorporated by reference.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle. 1987. J. Mol. Evol. 35:351-360; the method is similar to that described by Higgins & Sharp. 1989. CABIOS 5:151-153, all of which are expressly incorporated by reference. Useful PILEUP parameters include a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., PNAS USA 90:5873-5787 (1993), all of which are expressly incorporated by reference. A particularly useful BLAST program is the WU-BLAST-2 program which was obtained form Altschul et al., Method in Enzymology, 266: 460-480 (1996), all of which are expressly incorporated by reference. WU-BLAST-2 uses several search parameters, most of which are set to the default values. The adjustable parameters are set with the following values: overlap span=1, overlap fraction=0.125, word threshold (T)=11. The HSP S and HSP S2 proprameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389-3402, which is expressly incorporated by reference. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of p42 polypeptide. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids or nucleic acid residues than the sequences in the figures, it is understood that in one embodiment, the percentage of sequence identity will be determined based on the number of identical amino acid or nucleic acid residues in relation to the total number of residues. Thus, for example, sequence identity of sequences shorter than that shown in FIG. 1, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "longer" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

The p42 polypeptides of the present invention may be shorter or longer than the amino acid sequences shown in the figures. Thus, in a preferred embodiment, included within the definition of p42 polypeptides are portions or fragments of the amino acid sequences provided herein. In one embodiment, fragments of p42 polypeptides are considered p42 polypeptides if a) they share at least one antigenic epitope; b) have at least the indicated sequence identity; and/or c) preferably have p42 polypeptide immunologic activity as defined herein. The nucleic acids encoding the p42 polypeptides also can be shorter or longer than the sequences in the figures.

In addition, as is more fully outlined below, p42 polypeptides can be made that are longer than those depicted in the figures. For example, by the addition of an epitope or purification tags, the addition of other fusion sequences, or the elucidation of additional coding and non-coding sequences. As described below, the fusion of a p42 polypeptides to a polypeptide, such as a flg5 leader polypeptide, is particularly preferred.

p42 polypeptides may also be identified as encoded by p42 nucleic acids which hybridize to the sequences depicted in the figures or to nucleic acid sequences that encode the amino acid sequences depicted in the figures, or the complement thereof, as outlined herein. Hybridization conditions are further described below.

In a preferred embodiment, p42 polypeptide must share at least one epitope or determinant with the full length protein. By "epitope" or "determinant" herein is meant a portion of a protein which will generate and/or bind an antibody. Thus, in most instances, antibodies made to smaller p42 polypeptides will be able to bind to the full length protein. In another embodiment, antibodies made to native p42 polypeptide will bind to smaller p42 polypeptides, provided that the smaller polypeptides contain an epitope found on the full-length polypeptide that is recognized by the antibodies made to native p42 polypeptide. Accordingly, in a preferred embodiment p42 polypeptide is immunogenic. By "immunogenic" or "immunogen" and grammatical equivalents herein is meant a substances that induces or evokes an immune response, such as a cell-mediated and/or humoral (antibody) immune response, in a mammal. In a preferred embodiment the immune response substantially reduces the symptoms and manifestations associated with *plasmodium* infection, as described herein.

In the case of the nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. Thus the sequence identity of the nucleic acid sequence as compared to the nucleic acid sequence of the figures is preferably greater than 75%, more preferably greater than about 80%, particularly greater than about 85% and most preferably greater than 90%. In some embodiments the sequence identity will be as high as about 93 to 95 or 98%.

In a preferred embodiment, a p42 nucleic acid encodes a p42 polypeptide. As will be appreciated by those in the art, due to the degeneracy of the genetic code, an extremely large number of nucleic acids may be made, all of which encode the p42 polypeptides of the present invention. Thus, having identified a particular amino acid sequence, those skilled in the art could make any number of different nucleic acids, by simply modifying the sequence of one or more codons in a way which does not change the amino acid sequence of the p42 polypeptide.

In one embodiment, a p42 polypeptide is identified as being encoded by a nucleic acid that hybridizes under high stringency to the nucleic acids sequence shown in the figures, or their complement. High stringency conditions are known in the art; see for example Maniatis et al., Molecular Cloning: A Laboratory Manual, 2d Edition, 1989, and Short Protocols in Molecular Biology, ed. Ausubel, et at., both of which are hereby incorporated by reference. Stringent conditions are sequence-dependent and will be different in different circumstances. Longer sequences specifically hybridize at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993), which is expressly incorporated by reference. Generally, stringent conditions are selected to be about 5-10° C. lower than the thermal melting point ($T_m$) for the specific sequence at a defined ionic strength, pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at about pH 7.0 to 8.3 and the temperature is at least about 30° C. for short probes (e.g. about 10 to 50 nucleotides) and at least about 60° C. for long probes (e.g. greater than about 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

As used herein and further defined below, "nucleic acid" may refer to either DNA or RNA, or molecules which contain both deoxy- and ribonucleotides. The nucleic acids include genomic DNA, cDNA, and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in the figures also include the complement of the sequence.

By the term "recombinant nucleic acid" herein is meant nucleic acid, originally formed in vitro or in a cell in culture, in general, by the manipulation of nucleic acid by endonucleases and/or exonucleases and/or polymerases and/or ligases and/or recombinases, to produce a nucleic acid not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

The p42-M nucleic acids (see e.g., nucleotides 1-1232 of SEQ ID NO:6) are included within the definition of p42 nucleic acids and comprise nucleic acids encoding p42 and p42-M polypeptides (see e.g., amino acid residues 1-402 of SEQ ID NO: 16) which differ from p42 nucleic acids (see e.g., SEQ ID NO: 1) by the substitution of one or more codons with codons encoding the same or similar amino acid (see e.g., the amino substitutions as described herein) wherein the p42-M mRNA transcript is preferentially recognized by the tRNAs present in the insect host cell expression system (see, e.g., FIG. 27 which discloses the codons preferentially used by insect host cell *Trichoplusia ni*). This results in enhanced translation of the p42-M mRNA transcripts and enhanced production of the p42-M polypeptide. The p42-M.2 nucleic acids (see e.g., nucleotides 1-1200 of SEQ ID NO: 17) are further included within the definition of p42 nucleic acids and comprise nucleic acids encoding p42 and p42-M.2 polypeptides (see e.g., amino acid residues 1-392 of SEQ ID NO:18) wherein the 18 nucleotides encoding the histidine tail have been deleted.

The p42-M and p42-M.2 nucleic acid sequences exhibit one or more of the properties of optimizing recombinant polypeptide expression in insect host cells, of expressing higher recombinant polypeptide concentrations of immunogen in culture supernatants, and of expressing a more homogenous (or purified) recovered p42 immunogen. In a preferred embodiment, the p42-M nucleic acids exhibit a 1-2 fold increase in p42-M polypeptide expression levels relative to p42 nucleotide expression of p42 polypeptides, more preferably the p42-M nucleic acids exhibit a 2-3 fold increase in p42-M polypeptide expression levels relative to p42 nucleotide expression of p42 polypeptides, even more preferably the p42-M nucleic acids exhibit a 3-4 fold increase in p42-M polypeptide expression levels relative to p42 nucleotide expression of p42 polypeptides, and most preferably the p42-M nucleic acids exhibit at least a 4 fold increase in p42-M polypeptide expression levels relative to p42 nucleotide expression of p42 polypeptides.

In another preferred embodiment, the p42-M.2 nucleic acids exhibit a 1-3 fold increase in p42-M.2 polypeptide expression levels relative to p42 nucleotide expression of p42 polypeptides, more preferably the p42-M.2 nucleic acids exhibit a 4-5 fold increase in p42-M.2 polypeptide expression levels relative to p42 nucleotide expression of p42 polypeptides, even more preferably the p42-M.2 nucleic acids exhibit a 6-7 fold increase in p42-M.2 polypeptide expression levels relative to p42 nucleotide expression of p42 polypeptides, and most preferably the p42-M.2 nucleic acids exhibit at least an 8 fold increase in p42-M.2 polypeptide expression levels relative to p42 nucleotide expression of p42 polypeptides.

In still another preferred embodiment, the p42-M and p42-M.2 nucleic acids are expressed in a recombinant baculovirus (BV) possessing an optimized promoter and translation initiation region operably linked to the p42-M or p42-M.2 nucleic acid. In a preferred embodiment, an optimized promoter and translation initiation region are operably linked to a p42-M.2 nucleic acid.

In still another preferred embodiment, the p42-M and p42-M.2 nucleic acids are expressed in a recombinant baculovirus (BV) possessing an optimized promoter and translation initiation region operably linked to the p42-M and p42-M.2 nucleic acid. In still another embodiment, Tn5 (*Trichoplusia ni* or HIGH FIVE™) host cells are transformed with baculovirus expressing the p42-M and p42-M.2 nucleic acids.

A p42, as previously described herein, "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and/or deletions, as discussed below.

Included in the definition of p42 polypeptides are p42 polypeptide variants. These variants fall into one or more of three classes: substitutional, insertional or deletional variants. These variants ordinarily are prepared by site specific mutagenesis of nucleotides in the DNA encoding a p42 polypeptide, using cassette or PCR mutagenesis, scanning mutagenesis, gene shuffling or other techniques well known in the art, to produce DNA encoding the variant, and thereafter expressing the DNA in recombinant cell culture as outlined above. However, variant p42 polypeptide fragments having up to about 100-150 residues may be prepared by in vitro synthesis using established techniques. Amino acid sequence variants are characterized by the predetermined nature of the variation, a feature that sets them apart from naturally occurring allelic or interspecies variation of the p42 polypeptide amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed p42 polypeptide variants are screened for the optimal combination of desired activity. Techniques for making mutations at predetermined sites in DNA having a known sequence are well known. For example, the variations can be made using oligonucleotide-mediated site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)], all of which are expressly incorporated by reference, PCR mutagenesis, or other known techniques can be performed on the cloned DNA to produce the p42 polypeptide variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989), which is expressly incorporated by reference]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976), which are expressly incorporated by reference]. If alanine substitution does not yield adequate amounts of variant, an isoteric amino acid can be used. Screening of the mutants or variants is done using assays of p42 polypeptide activities and/or properties as described herein.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the p42 polypeptide are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |

CHART I-continued

| Original Residue | Exemplary Substitutions |
|---|---|
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the p42 polypeptide as needed, for example, to increase the immunogenicity of the p42 polypeptide. Alternatively, the variant may be designed such that the biological activity of the p42 polypeptide is not altered. For example, glycosylation sites may be added, altered or removed. p42 polypeptide may be designed to add phosphorylation sites.

p42 polypeptide fragments may be prepared by any of a number of conventional techniques. Desired peptide fragments may be chemically synthesized. An alternative approach involves generating p42 polypeptide fragments by enzymatic digestion, e.g., by treating the protein with an enzyme known to cleave proteins at sites defined by particular amino acid residues, or by digesting the DNA with suitable restriction enzymes, expressing the digested DNA and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, p42 polypeptide fragments share at least one biological and/or immunological activity with the native polypeptides shown in the figures.

In another aspect of the invention, as noted above, we have found that when a p42 amino acid sequence is expressed in insect cells, a pure product can be obtained without degradation or cleavage if DNA coding for a MAD allele sequence is employed. An amino acid sequence of the p42 antigen is considered to be of the MAD allele if it corresponds to the parts of gp195 of the MAD *Plasmodium falciparum* isolate which are dimorphic as compared with the amino acid sequences of the Wellcome and K1 isolates (Tanabe et al. 1987. J. Mol. Biol. 195:273). For example, gp195 of the FUP isolate is of the MAD allele (Chang et al. 1989. Proc. Natl. Acad. Sci. USA 86:6343; Chang et al. 1988. Exp. Parasitol. 67:1) (FUP isolate p42 amino acid sequence is as well).

The method for producing BVp42 according to this aspect of the invention-involves infecting an insect cell host with a recombinant baculovirus vector, that vector containing DNA coding for a p42 amino acid sequence of surface protein gp 195 of the *Plasmodium falciparum* MAD allele, operably linked to a baculovirus polyhedron promoter. Production of BVp42 with the sequence of the MAD allele, preferably of the FUP isolate sequence, results in pure, undegraded antigen.

A high level of inhibition of parasite growth is exhibited by anti-BVp42 sera. As noted above, strong inhibition of parasite growth by sera of monkeys vaccinated with Mab 5.2 affinity purified parasite gp195 correlates with the ability to induce substantially complete protection against infection. Other types of purification systems also can be used as known in the art, such as, molecular exclusion chromatography, phenyl HIC. Affinity chromatography also may employ a specific sequence or moiety either native or added to p42 wherein the sequence or moiety specifically binds to a compound or chemical such as in Ni-NTA chromatography, or an epitope can be added or fused to the p42 protein which is purifed by affinity chromatography with an antibody the binds to the added epitoped.

Without wishing to be bound by any theory of the invention, our results provide new insights into the interpretation of the vaccination study discussed above utilizing parasite gp 195 that was affinity purified using Mab 5.2. As shown herein, utilization of this Mab (now found by us to be specific for a conformational epitope located within the p42 processing fragment) for affinity purification of parasite gp 195 results in an antigen preparation that contains the gp195 precursor but that is also highly enriched for several C-terminal processing fragments, including p42. Based on the analysis of the specificity of anti-parasite gp195 antibodies utilizing the BVp42 polypeptide, a majority of antibodies produced by immunization with Mab 5.2 affinity purified parasite gp195 is specific for the C-terminal p42 processing fragment. The importance of p42 epitopes in immunity is consistent with the strong inhibition of parasite growth obtained with anti-BVp42 sera. There have been reports of several Mabs specific for this region which inhibit in vitro parasite growth (Pirson et al. 1985. J. Immunol. 134:1946; Blackman et al. 1990. J. Exp. Med. 172:379); Thus, it is possible that the exceptional level of protection achieved in the previous vaccination study was due to the focusing of the immune response on C-terminal epitopes which appear to serve as targets of functional effects such as the direct inhibition of parasite growth.

A study of the influence of MHC genes on immunological responsiveness to gp195 had found that a variety of congenic mouse strains were capable of producing antibodies against gp195 (Chang et al. 1989. Proc. Natl. Acad. Sci. USA 86:6343). We have detected BVp42-specific antibodies in seven congenic mouse strains immunized with purified, parasite gp195, indicating that individuals of many H-2 haplotypes are capable of recognizing epitopes within the smaller, p42 region of gp195. Thus, BVp42 can likely be used as a vaccine antigen in hosts of diverse genetic makeup.

Techniques known to one skilled in the art for expressing foreign genes in insect host cells can be used to practice the invention. Methodology for expressing polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; and in U.S. Pat. No. 4,745,051, all hereby incorporated by reference in their entirety. The techniques are summarized below.

To make BVp42, or an effective immunogenic part thereof, a polyhedron shuttle vector is used to shuttle all or part of the p42 coding sequence into a nuclear polyhedrosis virus. This vector contains the promotor of the polyhedron gene of a nuclear polyhedrosis virus and an available cloning site for the insertion of a selected gene such that the selected gene is under transcriptional control of the polyhedron promotor. Thus, the shuttle vector is engineered to contain the p42 sequence operably linked to a baculovirus polyhedrin promoter.

For example, the p42 sequence can be inserted into a commonly used polyhedron transfer vector, such as pAC373, to produce a recombinant shuttle vector for introducing foreign genes into a nuclear polyhedrosis viruses, such as Polyhedron californica nuclear polyhedrosis virus (AcMNPV), resulting in a recombinant viral expression vector capable of expressing the gene encoding for p42 in a host insect cell. pAC373 contains a deletion of the sequence between −8 (8 bases upstream from the polyhedron ATG and approximately 40 bases downstream from the polyhedron transcriptional start site) and the natural BamHI sites at nucleotide+171 (Luckow et al. 1988. Trends in the Development of Baculovirus Expression Vectors, Biotechnology, 6:47) resulting in a construct which can be used to express full-length gene which contains an internal ATG (N-formyl methionine initiation).

Any p42 coding DNA can be used to make the expression vector. While natural DNA sequences of various *Plasmodium falciparum* isolates are described herein, it is within ordinary skill in the art to vary those sequences. Thus, non-natural DNA sequences, different from the particular ones listed herein, can be used effectively in practicing the invention. For example, given the degeneracy of the genetic code DNA sequences encoding a protein can be modified to optimize expression for particular organisms and/or cells types, such as, tailoring the codon usage to those codons that are preferred by a given expression system, without modifying the desired amino acid sequence of the expressed protein.

Similarly, non-natural amino acid sequences can be coded for by the DNA used in the transfer vector in order to obtain functional products that obtain the advantages of the invention.

The C-terminus of BVp42 is preferably truncated, as discussed above, to remove the hydrophobic tail sequence (i.e., membrane anchor) to allow for protein secretion. For example, the entire anchor sequence e.g. amino acids 1708-1725 of the FUP isolate and corresponding amino acids of other isolates, can be deleted. An embodiment discussed in the examples below deletes an additional two amino acids at the N-terminus of the anchor sequence.

Thus it is within the scope of the invention to delete portions of the p42 amino acid sequence which do not affect the beneficial result obtained with the BVp42 products exemplified herein.

Transfer of the hybrid DNA to an expression vector is accomplished by transfection of the host insect cell, e.g. *Spodoptera frugiperda* (sf) cells, with a mixture of both the recombinant transfer plasmid DNA and wild type nuclear polyhedrosis virus (MNPV).

The transfected plasmid DNA recombines with the homologous sequences in the wild-type baculovirus genome to produce a viral genome that carries an integrated copy of the foreign gene.

The recombinant expression vector, comprising the hybrid polyhedron-p42 gene incorporated in the MNPV genome is then selected from the mixture of nonrecombinant and recombinant baculoviruses. For example, the supernatant containing the mixture of wild-type and recombinant budded viruses is collected, clarified by centrifugation and used for subsequent plaque assays. The preferred means of selection is by visual screening for the absence of viral occlusion bodies or by plaque hybridization with nucleic acid coding for p42, such as described in Kiefer et al. 1991. Growth Factors 5:115-127.

Expression of the p42 gene is accomplished by infecting susceptible host insect cells, such as sf cells, with the recombinant baculovirus p42-expression vector in an appropriate medium for growth. Propagation of the baculovirus p42-expression vector is achieved in the insect cells through replication and assembly of infectious virus particles.

Various nuclear polyhedrosis viruses can be employed in making expression vectors for use in the invention. Suitable viruses include, but are not limited to, *Polyhedron californica* nuclear polyhedrosis virus (AcMNPV), *Spodoptera frugiperda* nuclear polyhedrosis virus, *Choristoneura fumiferana* nuclear polyhedrosis virus, *Spodoptera littoralis* nuclear polyhedrosis virus, or *Trichoplusia ni* nuclear polyhedrosis virus, all known in the art and commonly available.

Suitable insect host cells for use in the invention include, but are not limited to, Sf9 (*Spodoptera frugiperda*), *Spodoptera exiaua, Choristoneura fumiferana, Trichoplusia ni*, and *Spodoptera littoralis, Drosophila* and other cells known in the art.

The polypeptide may be produced as either a fusion product, such as a heterologous protein containing part baculovirus amino acid sequence fused to *Plasmodium falciparum* sequence, or the product may merely contain a *Plasmodium falciparum* sequence. Methods of making both types of proteins are well known to one skilled in the art.

Accordingly, in a preferred embodiment, the invention provides fusion polypeptides comprising a, first, p42 polypeptide and at least a second polypeptide, wherein the second polypeptide is a p42 polypeptide, as defined herein, or a heterologous polypeptide. The p42 polypeptide and second polypeptide are fused covalently or non-covalently, with covalently being preferred. As will be appreciated by those in the art, the fusion polypeptides of the invention can be configured in a variety of ways. In one embodiment, the p42 polypeptide is fused to the carboxy terminus of the second polypeptide. Alternatively, the p42 polypeptide is fused to the amino-terminus of the second polypeptide. In another alternative embodiment, the p42 polypeptide is at a position internal to the carboxy and amino termini or the second polypeptide. Accordingly, the p42 polypeptide and the second polypeptide are joined to produce linear fusions or branched fusions in any manner as the biology and activity permits, although in general, N- or C-terminal fusions are preferred to internal fusions.

In general, the fusion polypeptides of the invention can be made either recombinantly or synthetically.

In a preferred embodiment, the p42 and second polypeptides are attached through the use of functional groups on each that can then be used for attachment. Preferred functional groups for attachment are amino groups, carboxy groups, oxo groups and thiol groups. These functional groups can then be attached, either directly or indirectly through the use of a linker. Linkers are well known in the art; for example, homo-or hetero-bifunctional linkers as are well known (see 1994 Pierce Chemical Company catalog, technical section on cross-linkers, pages 155-200, incorporated herein by reference). Preferred linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and C2 alkene being especially preferred. Suitable crosslinking agents include, e.g., 1, 1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl) dithio]propioimidate. Accordingly, at least one amino acid that reacts with a crosslinking agent may be added to a p42 polypeptide or the second polypeptide antibody by insertion and/or substitution to facilitate crosslinking.

In a preferred embodiment, the p42 and second polypeptides are crosslinked to a third molecule, which accordingly provides a scaffold for linking the p42 and second polypeptides. Suitable scaffolds include, for example, peptides, carbohydrates, nucleic acids, lipids, small organic molecules and the like. The crosslinkers function to join the p42 and second polypeptide and preferably allow each component to function without interference from the other component or the crosslinker.

In one embodiment, linear fusions are preferred. Accordingly, the p42 polypeptide is directly fused either to the amino terminus, carboxy terminus, and/or is internal to the termini of the second polypeptide. In a preferred embodiment, linkers, spacers, or adapters comprised of amino acids are used to join the p42 polypeptide and second polypeptide. In some embodiments, the fusion nucleic acid optionally encodes linkers, crosslinkers, spacers, or adapters, as needed. The number of amino acids comprising the linker can be determined by routine experimentation by a skilled artisan. The linkers comprising a sufficient number of amino acids such that the p42 and second polypeptides function without interference from the other. Accordingly, amino acids that comprise the linker preferably do not substantially alter biological activity of the p42 or second polypeptide.

For example, useful linkers include glycine polymers $(G)_n$, glycine-serine polymers (including, for example, $(GS)_n$, $(GSGGS)_n$ (SEQ ID NO:77) and $(GGGS)_n$ (SEQ ID NO:78), where n is an integer of at least one), glycine-alanine polymers, alanine-serine polymers, and other flexible linkers such as the tether for the shaker potassium channel, and a large variety of other flexible linkers, as will be appreciated by those in the art. Glycine and glycine-serine polymers are preferred since both of these amino acids are relatively unstructured, and therefore may be able to serve as a neutral tether between components. Glycine polymers are the most preferred as glycine accesses significantly more phi-psi space than even alanine, and is much less restricted than residues with longer side chains (see Scheraga, Rev. Computational Chem. III73-142 (1992), expressly incorporated by reference). Secondly, serine is hydrophilic and therefore able to solubilize what could be a globular glycine chain. Third, similar chains have been shown to be effective in joining subunits of recombinant proteins such as single chain antibodies.

In a preferred embodiment, either or both p42 and the second polypeptide of the invention can comprise additional components or may be modified in other ways. For example, modification of the fusion polypeptides include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "amino groups of lysine, arginine, and histidine side chains [T. E. Creighton, *Proteins: Structure and Molecular Properties*, W.H. Freeman & Co., San Francisco, pp. 79-86 (1983), expressly incorporated by reference], acetylation of the N-terminal amine, and amidation of any C-terminal carboxyl group.

Another type of covalent modification of the p42 and second polypeptide included within the scope of this invention comprises altering the native glycosylation pattern of the polypeptide. "Altering the native glycosylation pattern" is intended for purposes herein to mean deleting one or more carbohydrate moieties found in native sequence of the fusion polypeptide components, and/or adding one or more glycosylation sites that are not present in the native sequences.

Addition of glycosylation sites may be accomplished by altering the amino acid sequence thereof. The alteration may be made, for example, by the addition of, or substitution by, one or more serine or threonine residues to the fusion polypeptide sequence (for O-linked glycosylation sites). The alteration also may be made, for example, by the addition of, or substitution by one or more Asn-Xaa-Ser/Thr sites (Xaa=any amino acid; for N-linked glycosylation sites) in the fusion polypeptide sequence. The fusion polypeptide amino acid sequence may optionally be altered through changes at the DNA level, particularly by mutating the DNA encoding the p42 polypeptide at preselected bases such that codons are generated that will translate into the desired amino acids.

Another means of increasing the number of carbohydrate moieties on the fusion polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981), all of which are expressly incorporated by reference.

Removal of carbohydrate moieties present on p42 or the fusion polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981), all of which are expressly incorporated by reference. Enzymatic cleavage of carbohydrate moieties on polypeptides can be achieved by the use of a variety of endo- and exo-glycosidases as described by Thotakura et al., *Meth. Enzymol.*, 138:350 (1987), expressly incorporated by reference.

Another type of covalent modification of p42 or the fusion polypeptide comprises linking the p42 or fusion polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337, all of which are expressly incorporated by reference.

In one embodiment, the p42 polypeptide is fused to an epitope tag which provides an epitope to which an anti-tag antibody can selectively bind. The epitope tag is generally placed at the amino-or carboxyl-terminus of the p42 polypeptide but may be incorporated as an internal insertion or substitution as the biological activity permit. The presence of such epitope-tagged forms of a p42 polypeptide can be detected using an antibody against the tag polypeptide. Also, provision of the epitope tag enables the p42 polypeptide to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988), which is expressly incorporated by reference]; the c-myc tag and the 8F9, 3C7, 6E10, G4, B7 and 9E10 antibodies thereto [Evan et al., *Molecular and Cellular Biology,* 5:3610-3616 (1985), which is expressly incorporated by reference]; and the Herpes Simplex virus glycoprotein D (gD) tag and its antibody [Paborsky et al., *Protein Engineering,* 3(6):547-553 (1990), which is expressly incorporated by reference]. Other tag polypeptides include the Flag-peptide [Hopp et al., *BioTechnology,* 6:1204-1210 (1988), which is expressly incorporated by reference]; the KT3 epitope peptide [Martin et al., *Science,* 255:192-194 (1992), which is expressly incorporated by reference]; tubulin epitope peptide [Skinner et al., *J. Biol. Chem.,* 266:15163-15166 (1991)]; and the T7 gene protein peptide tag [Lutz-Freyermuth et al., *Proc. Natl. Acad. Sci. USA,* 87:6393-6397 (1990), which is expressly incorporated by reference] and the histidine tag and metal binding sites (Smith, Ann. NY. Acad. Sci., 646:315-321 (1991), which is expressly incorporated by reference], with the Flag and histidine tag being preferred.

In a preferred embodiment, nucleic acid encoding a leader sequence can be included in the expression vector and fused to the amino terminus of the p42 polypeptide to facilitate sorting through the endoplasmic reticulum and proper folding of the polypeptide product. For example, flg5 cDNA encoding a leader sequence can be inserted 5' to the p42 coding region using conventional techniques. The flg5 leader is described in Kiefer et al. 1991.

Growth Factors 5:115-127. It is also disclosed in the Genebank and EMBL data bases (accession no. M60485). In addition, the flg5 DNA sequence used in a construct described in the examples below is shown in FIG. 7. The final purified product according to the invention may include a leader sequence, or the sequence may be cleaved during expression. Amino-terminal amino acid sequencing indicates that the polypeptide is appropriately cleaved.

The many variations in techniques for expressing and isolating BVp42 will be apparent to one skilled in the art. For example, promoters known in the art can be modified to alter expression. In addition, the number and composition of the nucleotides in the region between the promoter and start of the open reading frame can be modified to alter expression.

The BVp42 product can be conventionally purified, such as, in part, by affinity chromatography with a Mab specific for natural p42. Mab 5.2 is one such antibody. In another embodiment, BVp42 can be purified, for example, by the addition of a tag to the p42 polypeptide as described herein, preferably at the carboxy terminus, and purified by the appropriate affinity purification methods.

The BVp42 obtained is a variant of naturally occurring p42 that results from characteristic post-translational processing occurring in insect cells, especially Sf9 cells. Potential sites for post-translational modifications are shown in FIG. 6.

BVp42 has been found to be highly immunogenic in rabbits. High antibody titers against the immunogen can be obtained which meet or exceed titers of animals immunized with purified parasite gp195. ELISA titers were found similar in assays utilizing plates coated with either purified, parasite gp 195 or BVp42. More importantly, high titers were obtained when anti-BVp42 antibodies were reacted with purified, parasite gp195 in an ELISA and in an indirect immunofluorescence assay with schizonts and merozoites. IFA titers obtained after the fourth immunization with BVp42 reached levels exceeding those obtained by immunization with purified, parasite gp195.

Yeast produced p42 (Yp42) consisting of the same p42 sequence (amino acids nos. 1333 to 1705 in the FUP isolate) was found to be less immunogenic than BVp42, inducing lower antibody titers against the immunogen. In addition, the cross-reactivity of anti-Yp42 antibodies with parasite gp195 in the ELISA was much lower than cross-reactivity of anti-BVp42 antibodies. Yp42 also induced much lower IFA titers than BVp42, and statistically insignificant levels of parasite inhibition.

Immunoblotting studies demonstrated that most of the anti-BVp42 and anti-parasite gp 195 antibodies produced are specific for disulfide-dependent, conformational epitopes present on the same set of gp 195 processing fragments.

Accordingly, once made and purified, if necessary, the p42 polypeptides and p42 polypeptide fusions are useful in a number of applications, for example, in the induction of an anti-*plasmodium* immune response or treatment of a disease state in a patient or individual. The p42 polypeptides and fusions thereof of the present invention can be use alone or in combination with other therapeutic agents or carriers. In a preferred embodiment, the p42 polypeptides are employed as a vaccine.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

By "patient" or "individual" herein refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents or carriers includes simultaneous (concurrent) and consecutive administration in any order.

In a preferred embodiment, an adjuvant should be included with the BVp42 in the vaccine of the invention in order to enhance the immune response. Such adjuvants include Freund's complete adjuvant, B30-MDP, LA-15-PH, (Hui et al. 1990. Vaccine. Cold Spring Harbor Press. 477-483; Hui et al. 1991. Infection and Immunity 59:1585-1591; Hui et al. 1991 J. Immunol. 147:3935-3941), Freund's incomplete adjuvant, saponin, aluminum hydroxide, MF59, MTP-PE, QA-21, ISA51 or other available adjuvants or adjuvant combinations. Freund's complete adjuvant is not generally used clinically for human vaccines.

In a preferred embodiment, a pharmaceutically acceptable carrier is included in the therapeutic formulation, preferably a vaccine. Such carriers are well known to one skilled in the art and can be formulated according to known methods to prepare pharmaceutically useful compositions. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980), which is expressly incorporated by reference), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intramuscular, intraarterial or intralesional routes, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96, which is expressly incorporated by reference.

When in vivo administration of a fusion polypeptide is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212, which are expressly incorporated by reference. It is anticipated that different formulations will be effective for different treatment compounds and different disorders, that administration targeting one organ or tissue, for example, may necessitate delivery in a manner different from that to another organ or tissue.

Where sustained-release administration of a polypeptide is desired in a formulation with release characteristics suitable for the treatment of any disease or disorder requiring administration of the polypeptide, microencapsulation of the polypeptide is contemplated. Microencapsulation of recombinant proteins for sustained release has been successfully performed with human growth hormone (rhGH), interferon- (rhIFN—), interleukin-2, and MN rgp120. Johnson et al., *Nat. Med.*, 2:795-799 (1996); Yasuda, *Biomed. Ther.*, 27:1221-1223 (1993); Hora et al., *Bio/Technology.* 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010, all of which are expressly incorporated by reference.

The sustained-release formulations of polypeptides were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41, which is expressly incorporated by reference.

The vaccine preferably contains from about 0.1 to 5 mg in about a 0.1 ml to about 1.0 ml dose of BVp42. The vaccine can be administered in one or more doses, the amount administered being adjusted to correspond with the number of inoculations, either together or over a period of time. Administration can be carried out conventionally, preferably parenterally.

In a preferred embodiment, the vaccine preferably induces an immune response that substantially reduces the symptoms and manifestations associated with *plasmodium* infection, such as, the onset, the severity, and/or the duration of illness. The symptoms and manifestations include, for example, parasitemia, fever and chills which begin irregularly and later become synchronous in a non-immune individual. In a most preferred embodiment the immune response prevents overt or clinical disease.

In a preferred embodiment, the vaccine substantially delays the onset of a symptom in comparison to a non-vaccinated individual following infection at a dose that occurs normally in nature. Preferably, the symptom is parasitemia. Accordingly, the vaccine delays the onset of a symptom by about 2 days, preferably reduces onset of a symptom by about 4 days, more preferably by about 8 days, even more preferably by about 16 days or higher.

In a preferred embodiment, the vaccine substantially reduces parasitemia in comparison to a non-vaccinated individual following infection at a dose that occurs normally in nature. Accordingly, the vaccine reduces parasitemia by about 2 fold, preferably reduces parasitemia by about 10 fold, more preferably by about 100 fold, even more preferably by about 1,000 fold. In an even more preferred embodiment, parasitemia is reduced by 10,000 fold or higher and parasites can not be detected.

The present invention is further described in the examples below. The examples are for illustration purposes, and are not intended to limit the scope of the invention. All patents, patent applications, and publications and references cited therein are hereby expressly incorporated by reference in their entirety.

EXAMPLES

Example 1

Production and Purification of Baculovirus p42 (BVp42)

The Uganda Palo Alto (FUP) *Plasmodium falciparum* p42 coding region from $Ala_{1333}$ to $Ser_{1705}$, was cloned into a Polyhedron californica nuclear polyhedrosis virus (AcM-NPV) polyhedrin promoter regulated expression system (Luckow. 1988. Biotechnology 6:47).

FIG. 1 shows, schematically, the sequences that were cloned into a BVp42 encoding shuttle vector. The coding sequence, shown at top, included the flg5 leader (Flg$_L$, solid box) fused to the FUP isolate p42 coding region from Ala$_{1333}$ to Ser$_{1705}$. The BamHI fragment finally obtained was cloned into a AcMNPV transfer plasmid, shown at the bottom of the figure. The leader sequence for flg5 has been shown to direct secretion of the mature flg5 protein (Kiefer et al. 1991. Growth Factors 5:115-127). When fused to p42 coding DNA in the baculovirus expression system, the mature protein is also found to be secreted from the insect cells. "RV" is an EcoRV restriction site. The construct was made as follows.

Oligomers encoding the flg5 leader (Kiefer et al. supra), 5' portion of FUP isolate p42 from Ala$_{1333}$ to the HindIII site at amino acid Arg$_{1362}$ and BamHI sites were made on an automated DNA synthesizer (Applied Biosystems, Foster City, Calif.), kinased, annealed, and ligated. The overlapping oligomers consisted of six 43-mers, two 46-mers and two 19-mers. After digestion with BamHI, the ligation product was ligated into BamHI-digested and phosphatased pAB 114, a HindIII/SalI deletion of pBR322 containing a BamHI linker (Barr et al 1988. J. Biol. Chem. 263:16471). The HindIII/SalI fragment of p42 from a pAB 125 ADH$_2$-GAPDH alpha-factor construct (Hui et al. 1991. J. Immunol. 147:3935-3941), which includes an in-frame stop codon following Ser$_{1705}$, was ligated in-frame into this pAB114 vector to yield a flg5 leader fused to full-length p42 flanked by unique BamHI sites. The BamHI fragment was subsequently cloned into the BamHI site of the AcMNPV transfer plasmid pAc373 (Luckow. 1988. Biotechnology 6:47). The recombinant shuttle vector obtained was then used to transfer the coding sequence into AcMNPV by homologous recombination through transfection of sf9 cells (Summers et al. 1986. Tex. Agr. Exp. Station Bull. No. 7555, College Station, Tex.). Recombinant viruses were initially identified visually by occlusion negative phenotype and plaque hybridization with the BamHI fragment labeled by the oligomer primed extension method (Feinberg et al. 1984. Anal. Biochem. 137:266). The recombinant AcMNPV expression vector obtained, Flg5LFUP42AcNPV, was deposited with the American Type Culture Collection, 12301 Parklawn Drive, Rockville, Md., USA 20852, on Jan. 28, 1992 and has been assigned accession number VR2354. Infection of sf9 cells was carried out conventionally per Summers et al. 1986. supra.

Protein expression was initially monitored in roller bottles. Production was then scaled up to 0.5 liter batches in 2.8 liter Fembach shaker flasks. Culture supernatants were concentrated 10 to 50-fold by tangential flow ultrafiltration (Amicon). Recombinant BVp42 was purified from the concentrated supernatant by the affinity chromatography technique utilized to purify parasite gp195 as described by Siddiqui et al. 1987.

FIG. 2A shows silver stains (lane 1) and immunoblots (lane 2) of the affinity chromatography purified BVp42. The silver stained antigens were electrophoresed in SDS polyacrylamide gels. The immunoblots were reacted with a rabbit anti-parasite gp195 serum pool.

A single band migrating at approximately 44 kDa was observed in the silver stain. In the immunoblots, the purified BVp42 displayed major immunoreactive species at the positions of the major protein bands, accompanied by minor reactivities with proteins of higher and lower molecular weight.

The DNA sequence of the BVp42 construct from BamHI to SalI is shown in FIG. 7, the numbering starting with the first nucleotide of BamHI and ending with the last nucleotide of SalI. A restriction map is shown schematically at the top of the figure and the same sites are shown adjacent to the corresponding sequences below.

Edman sequence of the expressed protein of BVp42 resulted in a main N-terminal sequence consistent with the expected p42 N-terminus: ISVTMDNILS (SEQ ID NO:9) The yield of this sequence was lower than expected, suggesting that some of the material may have a blocked N-terminus. A minor sequence corresponding to the N-terminus of bovine serum albumin (BSA) was also detected, indicating that there was a trace amount of BSA in the preparation.

Example 2

Production and Purification of Modified p42 Nucleic Acid Constructs (p42-M and p42-M.2)

The original p42 nucleotide sequence (SEQ ID NO: 1) was substantially modified in order to optimize recombinant p42 polypeptide expression, achieve higher recombinant polypeptide concentrations of immunogen in culture supernatants, and to enhance the purity of recovered p42 immunogen. The first embodiment of the modified p42 nucleotide sequence (p42-M) comprises nucleotides 1-1232 of SEQ ID NO: 6 (FIG. 12) and includes 18 nucleotides which encode a histidine tail. The deduced amino acid sequence for p42-M (p42-M polypeptide) comprises amino acids 1-402 of SEQ ID NO: 16. The second embodiment of the modified p42 nucleotide sequence (p42-M.2) comprises nucleotides 1-1200 of SEQ ID NO: 17 (FIG. 12) and excludes the 18 nucleotides encoding the histidine tail. The deduced amino acid sequence for p42-M.2 (p42-M.2 polypeptide) comprises amino acids 1-392 of SEQ ID NO: 18.

The strategy for production of the p42-M (SEQ ID NO: 6) and p42-M.2 (SEQ ID NO: 17) constructs was implemented in order to alter the codon usage in the p42 gene for compatibility with the codon usage of genes of the *Trichoplusia ni* (HIGH FIVE™) host cells used for p42 polypeptide expression. The following steps were involved in this strategy: (a) a codon usage table (FIG. 27) was obtained for *Trichoplusia ni* genes from a public data base (e.g., the codon usage database of Y. Nakamura, Kazusa DNA Research Institute; (b) based on the codon usage table, the nucleic acid sequence of p42 was altered to obtain the same frequency for each codon as a typical *Trichoplusia ni* gene. This modification involved calculating the number of codons for each animo acid of the P. falciparum MSP-1 gene sequence within the p42 coding region, determining the codon usage for each amino acid in the p42 nucleic acid coding region, and altering this codon usage frequency to be consistent with the *Trichoplusia ni* usage. Once the actual and desired codon frequencies were determined, appropriate codons were substituted over the entire p42 coding region sequence to achieve the desired codon frequencies. The modified sequence was then scanned for any stop codons that may have been inadvertently introduced as a result of these substitutions. Stop codons which were identified were corrected. The promoter and translation initiation region were additionally modified to conform to optimal sequences for gene expression (Ranjan, A., Hasnain, S.E., *Virus Genes*. 9(2): 149-153, 1995). Finally, conservative nucleotide substitutions were included in the construct to introduce several convenient restriction endonuclease cleavage sites throughout the gene in order to facilitate genetic manipulations.

The p42-M (SEQ ID NO: 6) and p41-M.2 (SEQ ID NO: 17) nucleic acid sequences were further modified to contain an optimized promoter and translation initiation region (GGATCCACTAAAATGTGGTCTTGGAAG) based on Ranjan and Hasnain, 1995. The translation initiation region was selected by comparing codon usage of all the known gene sequences from *Autographa californica* nuclear polyhedrosis virus (AcNPV) with codon usage of the gene sequence for firefly luciferase (luc) and codon usage of the gene sequence for the beta subunit of human chorionic gonadotropin (beta hCG). The luc gene and beta hCG gene are expressed at different levels in the baculovirus system. The highly expressed luc gene showed a codon usage similar to AcNPV genes, as reflected by a very low D-squared statistic value (0.78) and a similar G/C usage (45%) at wobble positions. However, the underexpressed beta hCG gene displayed a high D-squared value (7.3) and G/C usage (82.5%) at the wobble base position. Alignment of the 20 nucleotides around the initiation codon of 23 AcNPV genes identified a novel consensus translation initiation sequence of aag/ta/tat/aa/cAAaATGaa/ct/ag/aAan (SEQ ID NO:79). The most critical feature of this translation initiation region, the triple A string immediately before the initiation codon, was selected for use with the p42-M and p41-M.2 constructs.

The process for generating the final p42-M and p42-M.2 constructs using a modified PCR gene assembly protocol (FIG. 21) with overlapping oligonucleotides (40- to 50-mers; Table 12) encoding the complete p42-M (SEQ ID NO: 6) and p42-M.2 (SEQ ID NO: 17) constructs was more complex than originally contemplated and the various steps taken to generate these constructs is described below. The complete sequences of the final p42-M (SEQ ID NO: 6) and p42-M.2 (SEQ ID NO: 17) constructs are provided in FIG. 12.

Initial studies to determine feasibility of the protocol were carried out with 20 forward and 20 reverse p42 MSP-1 oligonucleotide primers (provided by GIBCO Invitrogen Corp., Carlsbad, Calif.) encompassing the p42-M and p42-M.2 constructs under standard PCR conditions, using Taq polymerase. These initial studies indicated it was not possible to reconstruct the entire p42-M/p42-M.2 construct in a single step using each of the 40 oligonucleotides (GIBCO Invitrogen Corp., Carlsbad, Calif.). In later experiments, a more viable strategy was employed in which pools of nucleotides corresponding to sequence blocks flanked by introduced restriction endonuclease sites were assembled with the intention that several fragments would be generated which could subsequently be combined to form the complete p42-M and p42-M.2 constructs.

Production of Construct I:

The strategy for production of the first construct generated is illustrated in FIG. 22 as Construct I. It was necessary to develop unique conditions, described below, for the production of each fragment since it was often not possible to simply mix the overlapping nucleotides together and obtain the specific, desired PCR product.

Fragment I(a) was generated in two steps: (1) 3 sets of top and bottom strand primers for the first half and 3 sets of top and bottom strand primers for the second half of this fragment (GIBCO Invitrogen Corp., Carlsbad, Calif.) were amplified separately by PCR (60 cycles), and (2) the combination of the products (215 bp and 277 bp, respectively) of the two reactions were combined with the top (forward) and bottom (reverse) strand primers (Oligonucleotides #1, #36; Table 12) and carried through a second PCR reaction (60 cycles) to generate the desired 350 bp fragment. Attempts were made to utilize a high fidelity DNA polymerase such as the Turbo Pfu DNA polymerase (Stratagene) or Expand High Fidelity DNA polymerase (Boehringer Manneheim) for this reaction, however a product was obtained only when Taq polymerase was used.

Fragment I(b) was generated in three steps by sequentially (1) pooling Oligonucleotides #23 through #27 and #53 through #57 (Table 12) and carrying out a PCR assembly reaction for 45 cycles, (2) taking the product of this first PCR assembly step, combining it with the forward primer (Oligonucleotide #23) and the reverse primer (Oligonucleotide #53) and performing an amplification reaction for 45 cycles, resulting in a 215 bp amplified product, and (3) digesting this amplified product with EcoRI and SacI to generate the 170 bp Fragment I(b).

Fragment I(c) was the only fragment which could be generated by simply combining all of the overlapping oligonucleotides (Oligonucleotides #9 through 20 and #40 through 50; Table 12). Twelve top stand and twelve bottom strand oligonucleotides were mixed (Oligonucleotides #9 through 20 and #40 through 50; Table 12) and elongated in the assembly stage of the reaction. The product of this reaction was subsequently diluted and combined with the forward and reverse primers for the I(c) fragment (GIBCO Invitrogen Corp., Carlsbad, Calif.), amplified by PCR (60 cycles), and purified. High fidelity enzyme Turbo Pfu DNA polymerase (Stratagene) was used to generate the I(c) fragment.

Each of the three amplified fragments were purified by the Geneclean silica matrix method (Bio 101/Qbiogene, Carlsbad, CA digested with the appropriate restriction enzymes to generate the restriction fragments shown in FIG. 22, and ligated with T4 DNA ligase. Since it was not possible to obtain cloned inserts directly with the ligation product, the ligated mixture was reamplified by PCR (35 cycles) with end primers (GIBCO Invitrogen Corp., Carlsbad, CA) and a high fidelity DNA polymerase(EXPAND™, a combination of Taq and Pwo DNA polymerases). This amplified product was digested with the restriction enzymes BamHI and KpnI, and ligated to an appropriately digested pUC 18 vector to generate a number of clones with the appropriate 1.2 kb insert.

Several of the clones containing the correct insert were evaluated by automated DNA sequencing. Several nucleotide errors were noted in the beginning of the sequence within fragment I(a) and a few additional point mutations were scattered in other portions of the gene. (FIG. 22, Construct I, location of mutations indicated by aserisks).

Production of Construct II:

The large number of sequence errors obtained in the beginning of the gene (FIG. 22) were thought to be due to amplification of this region in multiple stages involving several amplification reactions, the large number of cycles in each amplification, and usage of the error-prone Taq polymerase. Consequently, it was decided that this region of the gene would be reconstructed using a different approach in order to generate fewer mutations. The reconstruction included defining conditions under which it was possible to use the high fidelity Pfu polymerase (Stratagene) for PCR amplification of this region as well as fewer cycles (40 vs. 50 cycles) for PCR reactions.

In the first step of this process, the 5'-terminal BamHI-AccI fragment was generated in a separate PCR assembly reaction using Oligonucleotides #1, #2, #3, #31, #32, and #33 (Table 12), and 45 cycles. The BamHI-AccI fragment was then ligated using DNA T4 ligase with the AccI-EcoRI fragment to produce fragment II(a). The 3' end of this fragment was created by the assembly of overlapping oligonucleotides (Oligonucleotides #4 through #6 and #34 through #36; Table 12) corresponding to the 200 bp AccI-EcoRI fragment and production of a secondary amplification product by combining this AccI-EcoRI fragment with the 615 bp EcoRI-EcoRI internal fragment obtained by restriction digestion of Construct I in a PCR assembly reaction.

Since the rest of the gene in Construct I had been generated using high fidelity polymerases, it was likely that the few errors obtained in this region were due to contamination of the oligonucleotide primers with error sequences. New primers of higher purity (HPLC-purified oligonucleotides) were used (GIBCO Invitrogen Corp., Carlsbad, Calif.) to encompass the HindIII-SalI region of fragment II(b). The HindIII-SalI 180 bp fragment assembled from these oligonucleotides was then combined with the entire insert of Construct I (as a template) to produce the complete fragment II(b) using the 180 bp HindIII-SalI fragment as the forward primer and Oligonucleotide #50 (Table 12) as the reverse primer (GIBCO Invitrogen Corp., Carlsbad, Calif.).

Fragments II(a) and II(b) were then digested with the appropriate restriction endonucleases. These fragments were purified by Geneclean and ligated with DNA T4 ligase to the pUC vector to generate Construct II. Two clones (c1 and c2) containing the appropriate sized insert were obtained of Construct II and both were sequenced. They, however, were found to contain a few, new, mutations, as indicated in FIG. 22 (Construct II, c1 and c2; location of mutations indicated by asterisks).

Production of Construct III:

It was noted that between the two clones (c1 and c2), the correct sequence of the complete gene could be generated by fragment reassembly with the exception of the internal EcoRI-SacI region. Therefore, it was decided to resynthesize the EcoRI-SacI region using a new set of oligonucleotides (GIBCO Invitrogen Corp., Carlsbad, Calif.) and to recombine this gene assembly product after restriction enzyme treatment with the appropriate restriction fragments for the other regions from either the c1 or the c2 clones (FIG. 2, Construct III). These fragments were inserted into pUC 18 using T4 DNA ligase and recombinant colonies (Epicurean Coli XLI-Blue cell line, Stratagene, La Jolla, Calif.) containing the appropriate insert were sequenced. At the same time, the EcoRI-SacI fragment was subcloned into pUC and sequenced. The sequencing results indicated a single deletion within the EcoRI-SacI region in both the complete gene construct and the construct containing only the EcoRI-SacI region (FIG. 22, Construct III; location of mutation indicated by asterisk).

Production of Construct IV:

Since only a single mutation remained in the complete p42-M/p42-M.2 construct, this error was repaired using oligonucleotide-directed site specific mutagenesis. To accomplish this, a complementary primer pair (Oligonucleotides #29 and 59; Table 12), provided by GIBCO Invitrogen Corp., Carlsbad, Calif. was designed which encompassed the deletion and met appropriate criteria for site-directed mutagenesis (GC content, length, $T_m$). In order to avoid further problems with mutations, highly purified oligonucleotides prepared by polyacrylamide gel electrophoresis were used (GIBCO Invitrogen Corp., Carlsbad, Calif.). This oligonucleotide pair was used to prime synthesis of the entire recombinant plasmid using a minimal number of PCR cycles (15 cycles) and the high fidelity Turbo Pfu DNA polymerase (Stragene) which creates blunt-ended PCR products. The double stranded product was treated with DpnI to remove any parental template and the blunt-end product was circularized using T4 DNA ligase. This product was then used to transform E. coli to generate clones containing Construct IV. Construct IV was sequenced and the results indicated the correct DNA sequence over the entire gene. The insert of this plasmid was purified and subcloned into the pAC 373 transfer vector in order to generate a recombinant baculoviris containing the final form of the modified, optimized p42-M (or p42-M.2) baculovirus_construct.

The modified p42 baculovirus, now referred to as BVp42-M (modified BVp42 of the MAD20 allele) was plaque-purified and studied in small-scale (shaker flask) expression experiments. A comparison of p42 and p42-M polypeptide expression between parallel cultures infected with either the original BVp42 construct or the new BVp42-M construct is presented in FIGS. 23A and 23B. In terms of the kinetics of expression, the p42-M polypeptide encoded by BVp42-M appears to be expressed much more rapidly than the p42 polypeptide encoded by the BVp42 construct, and the p42-M polypeptide reaches peak expression levels relatively early (between 36 and 48 hours after infection) as can be visualized by both the capture ELISA results (FIG. 23A) and by Coomassie staining of SDS-Page (FIG. 23B). This peak is rather sharp, and is followed by a rapid drop in p42-M polypeptide levels. This drop is most likely due to degradation by cellular proteases. The drop in p42-M polypeptide levels detected in the capture ELISA assay at 54 h is accompanied by a disappearance of the p42-M polypeptide band in the corresponding Coomassie-stained gel. The magnitude of peak expression also appears to be much higher for the new BVp42-M construct as compared to the original BVp42.

In this experiment, the peak p42 polypeptide concentration of the original BVp42 construct was estimated at 0.7 µg/ml using the antigen-capture ELISA while the peak p42-M polypeptide concentration of the new BVp42-M construct was estimated at 2.3 µg/ml, approximately a four-fold increase. This is consistent with the fact that this is the first time that the p42-M band is detectable in Coomassie stains of crude supernatants of the infected culture. The enhanced level of expression of p42-M led to the development of the p42-M.2 construct (lacking the 18 nucleotides encoding the hexahistidine tag). The projected higher yield for the p42-M.2 construct should enable purification of the p42-M.2 polypeptide using alternative chromatographic techniques and the avoidance of the use of metal chelate chromatography.

It should be noted that the cultures were infected at an MOI which may not be the optimal MOI for p42-M/p42-M.2 polypeptide expression by this construct. The accelerated kinetics of p42-M/p42-M.2 expression provide an advantage for protein recovery since it will be possible to harvest supernatants while cell viability is still high and protease concentrations are minimal. The kinetic studies are being refined to determine the precise peak of expression, since there appears to be some proteolysis by 48 h, and the actual peak for p42-M/p42-M.2 is likely to occur between 36 and 48 h.

A mAb affinity chromatography assay was carried out with 75 ml p42-M.2 culture supernatant harvested at 40 h post-infection. A total of 500 µg of highly purified p42-M 0.2 protein was obtained, indicating an actual yield of 6.6 mg p42 per liter of culture. A Coomassie stained SDS-PAGE gel of this preparation is shown in FIG. 24. It is noted that the p42-M.2 band is the predominant band in this gel, with no indication of degradation or processing. In previous studies, an approximately ten-fold increase in expression levels has been observed in the bioreactor (collaborative studies performed at Ares-Serono, Geneva) as compared to shaker flasks. Consequently, it is projected that bioreactor expression levels of the BVp42-M.2 construct will be approximately 70 µg/ml or 70 mg/L. This level of expression would be more than adequate for large scale production and for clinical trials of this malaria antigen. Thus, a 20 L culture would be projected to produce 1.4 g of p42-M.2 protein.

Immunoreactivity of purified p42-M.2 polypeptide has been evaluated using several available mAbs specific for disulfide-dependent, conformational C-terminal determinants: Mabs 5.2 and AD9.1, Siddiqui et al., 1987. Proc Natl Acad Sci 84(9): 3014-3018; Locher et al., 1996. Exp Parasitol 84(1): 74-83); mAb G13; as well as Dr. S. Longacre' G14 mAb, the kind gift of Dr. Shirley Longacre; and a rabbit polyclonal antiserum against p42, Chang et al., 1992. J Immunol 149(2): 548-555. The p42-M.2 polypeptide reacted strongly with each of these antibodies by immunoblot (FIG. 25).

Development of a Simplified, Non-Denaturing Purification Scheme for Enhancing Recovery and Purity of p42-M.2

The purification scheme of p42-M.2 outlined below is based on the polypeptide's novel binding characteristics. Due to its amphipathic nature, p42-M.2 polypeptide displays a high affinity for hydrophobic ligands attached to a chromatographic matrix. Preliminary method scouting experiments demonstrated that one matrix exhibiting a high binding interaction and selective elution properties for p42-M.2 polypeptide was Phenyl Sepharose. The p42-M.2 polypeptide bound quantitatively and with high affinity to Phenyl Sepharose. Contaminants bound with a lower affinity could be eluted with a low salt buffer. Subsequently, a partially-purified p42-M.2 polypeptide preparation was obtained by elution with distilled water. This preparation was greatly enriched for the p42-M.2 polypeptide but also contained high and low molecular weight contaminants (FIG. 26, lane 2).

The p42-M.2 polypeptide enriched preparation was further purified by chromatography using Cibachron Blue Sepaharose, a ligand which binds to kinases, dehydrogenases and most other enzymes requiring adenyl-containing cofactors (e.g., NAD+), coagulation factors, interferons, lipoproteins and albumin. The p42-M.2 polypeptide binds with high affinity to Cibachron Blue and may be eluted only under high-stringency elution conditions (FIG. 26, lanes 7-8), enabling its separation from the remaining contaminants, some of which do not bind to this ligand, or can be eluted under milder conditions (FIG. 26, lanes 3-6). Consequently, a highly purified p42-M.2 polypeptide preparation is obtained in essentially a two-step purification procedure.

In addition to its relevance for purification, it is possible that the Cibachron Blue binding properties to p42-M.2 polypeptide may have implications for anti-malarial drug development. If binding can be shown to be adenyl-cofactor specific, it is possible that structural analogs of this ligand may inhibit parasite invasion, growth, and/or differentiation. The nature of the binding interaction between p42-M.2 polypeptide and Cibachron Blue is currently under investigation for drug development potential.

TABLE 12

Oligonucleotide Primers Used for the Production of the Modified p42 Nucleic Acid Sequence (p42-M and p42-M.2).

FORWARD OLIGONUCLEOTIDE PRIMERS (5'→3') Numbers (#s) 1-29

1  ATT GGA TCC ACT AAA ATG TGG TCT TGG AAG TGT
    CTT TTA TTC TGG GCT GT (F1)
    (SEQ ID NO: 19)

2  CCA CTC TTT GCA CAG CAG CGA TCT CTG TTA CTA
    TGG ACA ACA TCC TCA GTG (F2)
    (SEQ ID NO: 20)

TABLE 12-continued

Oligonucleotide Primers Used for the Production of the Modified p42 Nucleic Acid Sequence (p42-M and p42-M.2).

3  CGA GTA CGA CGT AAT CTA CCT AAA GCC CCT TGC
     CGG TGT CTA CCG TTC AT (F3)
     (SEQ ID NO: 21)

4  GAA AAG AAT ATT TTC ACG TTC AAC CTC AAC CTA
     AAT GAC ATC CTC AAC TCG CG (F4)
     (SEQ ID NO: 22)

5  CGA AAA TAC TTC CTC GAC GTG TTG GAA TCC GAC
     CTT ATG CAA TTT AAG CAC (F5)
     (SEQ ID NO: 23)

6  ACG AGT ACA TCA TAG AGG ACA GCT TCA AGC TCT
     TGA ATT CAG AAC AGA AGA ACA (F6)
     (SEQ ID NO: 24)

7  GTC CTA CAA ATA CAT TAA GGA GTC TGT TGA GAA
     CGA CAT CAA GTT CGC CCA GGA (F7)
     (SEQ ID NO: 25)

8  TAC TAT GAG AAA GTC CTG GCT AAA TAC AAG GAC
     GAC TTG GAA AGC ATT AA (F8)
     (SEQ ID NO: 26)

9  AAA GAA GAG AAG GAA AAG TTT CCG AGC TCT CCA
     CCC ACA ACT CCC CC (F9)
     (SEQ ID NO: 27)

10  AAG ACC GAC GAG CAG AAA AAA GAA AGT AAG TTC
     CTT CCA TTC CTC AC (F10)
     (SEQ ID NO: 28)

11  ACT CTA TAT AAC AAC CTG GTG AAC AAG ATT GAT
     GAC TAC TTA ATC AAC TTG AAG GCG (F11)
     (SEQ ID NO: 29)

12  GAC TGT AAC GTC GAA AAG GAT GAA GCC CAC GTT
     AAG ATC ACC AAG CTT TCC (F12)
     (SEQ ID NO: 30)

13  CCA TCG ACG ATA AGA TTG ACC TGT TTA AGA ACC
     ACA ACG ATT TCG ACG CA (F13)
     (SEQ ID NO: 31)

14  TGA TCA ACG ACG ATA CTA AGA AAG ACA TGC TTG
     GAA AAC TGG TGT CGA CAG (F14)
     (SEQ ID NO: 32)

15  AAA CTT CCC GAA CAC CAT TAT AAG CAA GCT GAT
     CGA AGG AAA GTT TCA (F15)
     (SEQ ID NO: 33)

16  AAC ATC TCT CAG CAT CAA TGC GTG AAG AAG CAA
     TGT CCC GAG AAT TCA G (F16)
     (SEQ ID NO: 34)

17  CCA CTT AGA CGA AAG GGA GGA ATG TAA ATG CCT
     GCT GAA TTA TAA ACA GG (F17)
     (SEQ ID NO: 35)

18  GTG CGT AGA GAA TCC TAA CCC AAC CTG TAA CGA
     AAA TAA CGG TGG CT (F18)
     (SEQ ID NO: 36)

19  CGC TAA GTG TAC CGA GGA GGA CAG CGG TTC CAA
     TGG CAA GAA AAT AAC T (F19)
     (SEQ ID NO: 37)

20  GAA GCC CGA TAG TTA CCC TCT CTT CGA CGG TAT
     CTT CTG CTC CCC ACC (F20)
     (SEQ ID NO: 38)

TABLE 12-continued

Oligonucleotide Primers Used for the Production of the Modified p42 Nucleic Acid Sequence (p42-M and p42-M.2).

21 TTC GAC GCA ATC AAA AAG TTG ATC AAC GAC GAT ACT AAG (F-14A)
(SEQ ID NO: 39)

22 AAA GAC ATG CTT GGA AAA CTG CTG TCG ACA GGC TTG GTC CA (F-14B)
(SEQ ID NO: 40)

23 GAG GAC AGC TTC AAG CTC TTG AAT TCA GAA CAG AAG AAC AC (F-6A)
(SEQ ID NO: 41)

24 CCT CCT AAA GTC CTA CAA ATA CAT TAA GGA GTC TGT TGA G (F-7B)
(SEQ ID NO: 42)

25 AAC GAC ATC AAG TTC GCC CAG GAA GGA ATT AGC TAC TAT G (F-7C)
(SEQ ID NO: 43)

26 AGA AAG TCC TGG CTA AAT ACA AGG ACG ACT TGG AAA GCA T (F-8D)
(SEQ ID NO: 44)

27 TAA GAA GGT AAT CAA AGA AGA GAA GGA AAA GTT TCC GAG (F-9E)
(SEQ ID NO: 45)

28 CTC TCC ACC CAC AAC T (F-9F)
(SEQ ID NO: 46)

29 GGA ATT AGC TAC TAT GAG AAA GTC CTG GCT AAA TAC AAG G (F-7D)
(SEQ ID NO: 47)

REVERSE OLIGONUCLEOTIDE PRIMERS (5'→3') Numbers (#S) 31-59

31 CTG CTG TGC AAA GAG TGG CGG TCA CCA AGA CAG CCC AGA ATA AAA GAC A (R1)
(SEQ ID NO: 48)

32 AGG TAG ATT ACG TCG TAC TCG TTC TCG AAG CCA CTG AGG ATG TTG TCC ATA (R2)
(SEQ ID NO: 49)

33 TTG AAC GTG AAA ATA TTC TTT TCT ATC TGT TTC TTC AAT GAA CGG TAG ACA (R3)
(SEQ ID NO: 50)

34 ACG TCG AGG AAG TAT TTT CGC TTG TTG AGG CGC GAG TTG AGG ATG TC (R4)
(SEQ ID NO: 51)

35 CTG TCC TCT ATG ATG TAC TCG TTA GAG CTA ATG TGC TTA AAT GCA TAG GTC (R5)
(SEQ ID NO: 52)

36 AGA CTC CTT AAT GTA TTT GTA GGA CTT TAG GAG GGT GTT CTT CTG TTC TGA ATT CAA (R6)
(SEQ ID NO: 53)

37 GCC AGG ACT TTC TCA TAG TAG CTA ATT CCT TCC TGG GCG AAC TTG A (R7)
(SEQ ID NO: 54)

38 AAA CTT TTC CTT CTC TTC TTT GAT TAC CTT CTT AAT GCT TTC CAA GTC GTC (R8)
(SEQ ID NO: 55)

39 TTT CTG CTC GTC GGT CTT TGC AGG CGA TGG GGG AGT TGT GGG TG (R9)
(SEQ ID NO: 56)

40 GTT CAC CAG GTT GTT ATA GAG AGT TTC GAT GTT GGT GAG GAA TGG AAG GAA CT (R10)
(SEQ ID NO: 57)

41 TCC TTT TCG ACG TTA CAG TCA TTA ATT TCG CCT TCA AGT TGA TTA AGT AGT (R11)
(SEQ ID NO: 58)

42 GTC AAT CTT ATC GTC GAT GGC TTT GAG ATC GGA AAG CTT GGT GAT CCT AAC (R12)
(SEQ ID NO: 59)

43 TTC TTA GTA TCG TCG TTG ATC AAC TTT TTG ATT GCG TCG AAA TCG TTG TGG T (R13)
(SEQ ID NO: 60)

44 ATG GTG TTC GGG AAG TTT TGG ACC AAG CCT GTC GAC AGC AGT TTT CC (R14)
(SEQ ID NO: 61)

45 CAT TGA TGC TGA GAG ATG TTC AGC ATA TCC TGA AAC TTT CCT TCG ATC AG (R15)
(SEQ ID NO: 62)

46 CTC CCT TTC GTC TAA GTG GCG AAG CAA CCT GAA ATT CTC GGG ACA TTG (R16)
(SEQ ID NO: 63)

47 GGT TAG GAT TCT CTA CGC ACT GTT CTC CTT CCT GTT TAT AAT TCA GCA GGC (R17)
(SEQ ID NO: 64)

48 CTC CTC GGT ACA CTT AGC GTC AGC ATC GCA GCC ACC GTT ATT TTC G (R18)
(SEQ ID NO: 65)

49 AGG GTA ACT ATC GGG CTT CGT GCA TTC GCA AGT TAT TTT CTT GCC ATT GG (R19)
(SEQ ID NO: 66)

50 GGC GTA GGT ACC TTA TTA ATG ATG ATG ATG ATG ATG AGG TGG GGA GCA GAA GAT AC (R20)
(SEQ ID NO: 67)

51 TTT TTG ATT GCG TCG AAA TCG TTG TGG (R-13A)
(SEQ ID NO: 68)

52 CAG TTT TCC AAG CAT GTC TTT CTT AGT ATC GTC GTT GAT CAA C (R-13B)
(SEQ ID NO: 69)

53 AGT TGT GGG TGG AGA GCT CGG AAA CTT TTC CTT CT (R-9A')
(SEQ ID NO: 70)

54 CTT CTT TGA TTA CCT TCT TAA TGC TTT CCA GTC GTC CTT T (R-9B')
(SEQ ID NO: 71)

55 GTA TTT AGC CAG GAC TTT CTC ATA GTA GCT AAT TCC TTC CT (R-8C')
(SEQ ID NO: 72)

56 GGG CGA ACT TGA TGT CGT TCT CAA GAG ACT CCT TAA TGT A (R-8D')
(SEQ ID NO: 73)

57 TTT GTA GGA CTT TAG GAG GGT GTT CTT CTG TTC TGA ATT C (R-7E')
(SEQ ID NO: 74)

58 AAG AGC TTG AAG CTG TCC TC (R-6F')
(SEQ ID NO: 75)

TABLE 12-continued

Oligonucleotide Primers Used for the Production
of the Modified p42 Nucleic Acid Sequence
(p42-M and p42-M.2).

59  CCT TGT ATT TAG CCA GGA CTT TCT CAT AGT AGC
     TAA TTC C (R-7D)
     (SEQ ID NO: 76)

p42-M.2 Polypeptide Purification Scheme

Phenyl Sepharose Primary Purification Protocol:

Mix an equal volume of p42-M.2 polypeptide lysate with 3M ammonium sulfate (pH 7.2). Mix gently. Centrifuge at 15K (4° C.; 30 minutes) to clear lysate of particulates. Lipids will float and form a layer on the top. Carefully decant. Avoid lipid top layer if possible.

Prepare Phenyl Sepharose column. Pour slurry into column. Use peristaltic pump to add washes and eluants. Wash beads with 10 volumes water, 10 volumes of 1.5 M ammonium sulfate in 20 mM NaH$_2$PO$_4$ (pH 7.2). Pass lysate over column.

Wash column with 10 volumes of 1.5 M Ammonium Sulfate in 20 mM 20 mM NaH$_2$PO$_4$ (pH 7.2).

Elute column with 5 volumes of 0.75M Ammonium Sulfate in 20 mM NaH$_2$PO$_4$ (pH7.2). Follow with 5 volumes of 20 mM NaH$_2$PO$_4$ (pH 7.2) and 5 volumes of dH$_2$O.

Check fractions for p42-M.2 polypeptide by dot blot. The purest p42-M.2 protein will be in water eluate.

Cibachron Blue Secondary Purification:

Pool fractions of Phenyl Sepharose purified p42-M.2 polypeptide. Add Tween-80 for a final concentration of 0.5%.

Prepare column. Wash with 10 volumes water. Equilibrate column with 10 volumes of 20 mM NaH$_2$PO$_4$ (pH 7.2) and 0.5% Tween-80.

Pass sample over column. Collect flow-thru to check if it has all bound. Wash column with 10 volumes of 20 mM NaH$_2$PO$_4$ (pH 7.2) and 0.5% Tween-80.

Elute column with 10 volumes of 2M NaCl in 20 mM NaH$_2$PO$_4$ (pH 7.2). Elute with 10 volumes [50% Ethylene Glycol and 50% 2M NaCl in 20 mM NaH$_2$PO$_4$ (pH 7.2). Check fractions. The p42-M.2 protein will elute in the 50% ethylene glycol fractions.

Example 3

Production and Purification of Baculovirus p42-K

Figure 13:
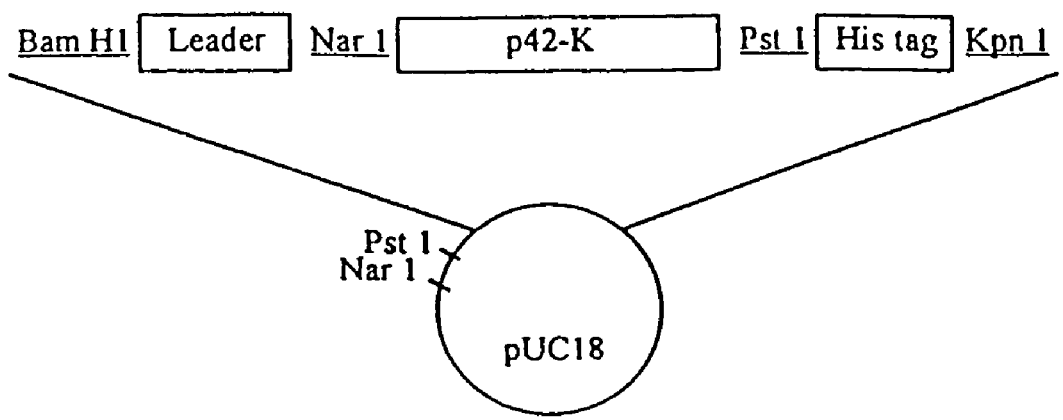
FIG. 13 shows the three-part construction of the p42-K coding region of the K1 allele of MSP-1 derived from the FVO strain of *P. falciparum*. Restriction sites used to ligate the fragments are underlined.

The K1 type (p42-K) of the p42 antigen was constructed using the Vietnam-Oak Knoll *P. falciparum* isolate (FVO). There are three parts to this construct: a leader sequence, the p42-K coding region and the histidine tag (FIG. 13). Restriction sites were incorporated into the primers to enable a "sticky-end" ligation of the three fragments. The leader sequence was altered from the original p42-M sequence such that three adenines were added three bases prior to the start site to optimize the codon preference for baculovirus and insect cells as well as the distance between the promoter sequence and the methionine start codon (Ranjan et al. 1995. Virus Genes 9(2):149-153). Primers containing NarI and PstI restriction site sequences were used to amplify the 1,065 base pair p42-K coding region corresponding to the Ala$_{1349}$ to Ser$_{1723}$ (as numbered by Miller et al. 1993. Mol. Biochem. Parasitol 59(1):1-14.) of MSP-1 from genomic *P. falciparum* DNA. Primers containing BamHI and NarI restriction site sequences were used to amplify the 91 base pair leader sequence. Oligonucleotides containing PstI and KpnI restriction site sequences were made to generate the 25 base pair histidine tag. All primers and oligonucleotide sequences used for the p42-K constructs are shown in Table 1.

TABLE 1

PCR Primer Sequences used in the Construction of p42-K

| Primer Name | | Sequence (5' to 3') |
|---|---|---|
| Leader F | (SEQ ID NO: 10) | ATT<u>GGATCC</u>ACTAAAATGTGGAGCTGGAAG |
| Leader R | (SEQ ID NO: 11) | TAT<u>GGCGCC</u>CGCGGTGCAGAGTGTGGCTGT |
| p42 F | (SEQ ID NO: 12) | TTA<u>GGCGCC</u>GCAGTAACTCCTTCCGTAATT |
| p42 R | (SEQ ID NO: 13) | TAA<u>CTGCAG</u>AAAATACCATCGAAAAGT |
| His F | (SEQ ID NO: 14) | TAA<u>CTGCAG</u>TCATCATCATCATCATCATTAATAA<u>GGTACC</u>GAG |
| His R | (SEQ ID NO: 15) | ATA<u>GGTACC</u>TTATTAATGATGATGATGATGATGA<u>CTGCAG</u>TTA |

Underlined sequences represent restriction sites.
Bold letters represent changes to the leader sequence.

The leader sequence of the BVp42 constructs and the p42-K coding region from FVO malaria parasite DNA were amplified by a high fidelity PCR reaction containing both Taq and Pwo DNA polymerases. This allows for the cloning of the leader and p42-K coding region into the transfer vector without mutations, since Pwo DNA polymerase contain 3' to 5' exonuclease proofreading activity. PCR reaction mixtures were brought up to 100 microliters with 200 micromolar of each dNTPs (Gibco BRL), 0.4 micormolar primers, 10 microliters of DNA template, 0.75 units of high fidelity polymerase (Roche Molecular Biochemicals, Indianapolis, IN) and 1X high fidelity reaction buffer (Roche Molecular Biochemicals). In order to amplify the leader sequence 1 cycle of 95° C. 5 min., and 35 cycles of 95° C. 1 min., 56° C. 1min., and 72° C. 1 min were used. For the amplification of the p42-K coding region, 1 cycle of 95° C. 5 min, and 35 cycles of 95° C. 1 min., 56° C. 1 min., and 72° C. 2 min. were used. The 1.1 kb p42-K PCR product was electrophoresed on a 1% Sea Plaque GTG (FMC) low melt agarose gel in 1X TAE and purified using the Geneclean III kit (Bio101, Vista, CA; ). The 90 base pair leader PCR product was electrophoresed on a 2% BioGel (Bio101 ) low melt agarose gel designed for small DNA fragments, excised, and purified using the Mermaid Spin Kit (Bio 101, Inc., 1070 Jushua Way, Vista, CA 92083. To construct the histidine tag, the His F and His R oligonucleotides were diluted to 5 μM in dH$_2$O. To anneal the oligonucleotides, equal volumes were heated to 37° C. for 10 min. and at room temperature for 20 min.

The leader sequence, MSP-1 p42-K coding region and histidine tag were restriction enzyme digested, purified by Geneclean III or Mermaid Spin Kit as needed and ligated into pUC18 (FIG. 13). The ligation was used to transform competent bacteria prepared as described by Sambrook et al. (1989). Plasmids from colonies were isolated and analyzed. Once a plasmid with the insert was identified as being in the correct orientation, the insert was subcloned into the transfer vector pAC373 and operably linked to the polyhedron promoter. Sequencing of the p42-K construct revealed a minor discrepancy when compared to the published MSP-1 sequence (Miller et al. 1993. Mol Biochem Parasitol. 59(1): 1-14.) A nucleic acid base mutation occurred at position 670 of the p42-K coding region, which resulted in an adenine to cytosine nucleotide substitution and in the CCA codon for proline instead of the ACA codon for threonine. The complete nucleic acid and amino acid sequences are sown in FIG. 14.

Transfection of *Spodoptera frugiperda* (Sf9) cells with a pAC373 and the *Autographa california* nuclear polyhedrosis virus (AcMNPV) DNA successfully produced recombinant virus. Supernatant containing the recombinant baculovirus was plaque assayed, plaque purified, and expanded to obtain high tittered stocks. Plaque assay results show that stocks contained titers to $1.6 \times 10^8$ pfu/ml or recombinant baculovirus. These high titers stocks were used to infect HIGH FIVE™ insect cells at a multiplicity of infection (MOI) of about 5. Western blots (Sambrook et al. 1989. Molecular Cloning: A Laboratory Manual. Cold Spring Harbor Laboratory Press. Plainview, NY) showed that HIGH FIVE™ cells produce BV p42-K protein beginning at 18 hours post infection (data not shown). At 42 hours the protein concentrations reached their peak levels of about 3-4 mg/L and the insect supernatants were harvested. Purification by affinity chromatography using 5.2 Mabs or phenyl HIC followed by Ni-NTA removed extraneous proteins. Analysis of purified recombinant protein by silver stains and western blots showed that the recombinant protein could be purified from insect cell supernatants and was present in high quantities (FIGS. 15 and 16).

Results of the BCA Protein Assay (Pierce, Rockford, IL.) showed that reasonable amounts of purified protein are attainable. Affinity chromatography with monoclonal 5.2 antibodies yielded a protein concentration of 670 μg/ml at the peak aliquots. Phenyl HIC chromatography followed by Ni-NTA chromatography yielded lower concentrations of protein (<100 μg/ml) at peak aliquots. The histidine tag does not seem to be binding efficiently to the Ni-NTA resin as can be seen by the amount of residual material in western blots of the column filtrate (FIG. 17). While the reason for this is unknown, it can be speculated that the histidine tag is not fully exposed in BVp42-K. Interestingly, even the denaturation of the protein with 6 M urea did not increase the recovery of purified protein.

Example 4

Comparison of Polyclonal Antibodies

*Aotus lemurinus griseimembra* monkeys (n=5) and New Zealand white rabbits (n=5) were immunized with BVp42 protein from the original BVp42 construct (the MSP-1 p42 construct obtained from the FUP isolate of *P. falciparum* [representing the MAD 20 "M" allele]) as described by Chang et al. 1996. Their antibodies were tested for reactivity with recombinant BVp42 and BVp42-K using indirect ELISA. Absorbancies were plotted on a scatter graph against the reciprocal of the antibody dilutions. Data points were adjusted into a linear relationship by changing the reciprocal dilution axis into a logarithmic scale. Data points for which the reciprocal dilution was greater than $4\times10^6$ were not used due to non-linearity at these dilutions. A regression line for the data series was constructed and the equation of the line calculated. The equation was solved for the X-intercept to determine the titer of serum samples. A test for difference scores was performed on the data to determine if any significant differences existed between antibody titers of BVp42 and BVp42-K (Koosis DJ. 1997. Statistics: A Self-Teaching Guide. John Wiley and Sons Inc., New York, N.Y.).

TABLE 2

ELISA Titer Comparison of Monkeys and Rabbits Immunized with BVp42 for BVp42 and BVp42-K

| | BVp42 | BVp42-K | Ratio K/M | Difference |
|---|---|---|---|---|
| Monkey | | | | |
| 3005 | 1310000 | 2340000 | 1.79 | −1030000 |
| 82055 | 1060000 | 1660000 | 1.57 | −600000 |
| 81591 | 390000 | 360000 | 0.92 | 30000 |
| 3006 | 670000 | 480000 | 0.72 | 190000 |
| 414 | 520000 | 620000 | 1.19 | −100000 |
| Average | 790000 | 1092000 | 1.38 | −302000 |
| Rabbit | | | | |
| K192 | 2600000 | 2380000 | 0.92 | 220000 |
| K191 | 1590000 | 1860000 | 1.17 | −270000 |
| K171 | 1430000 | 1670000 | 1.17 | −240000 |
| K170 | 1210000 | 1380000 | 1.14 | −170000 |
| K151 | 1730000 | 2100000 | 1.21 | −370000 |
| Average | 1712000 | 1878000 | 1.10 | −166000 |

The results showed that *Aotus* monkey sera reacted well with both the homologous BVp42 and heterologous BVp42-K proteins (Table 2). Antibody titers of BVp42 ranged from $3.9\times10^5$ with monkey 81591 to $1.31\times10^6$ with monkey 3005. BVp42-K titers ranged from $3.6\times10^5$ with monkey 81591 to $2.34\times10^6$ with monkey 3005. The average titer of the five monkeys with BVp42 was $7.9\times10^5$ with the average titer with BVp42-K was $1.09\times10^6$. The "t" test difference score result showed that antibody titers with BVp42 were not significantly different from BVp42-K using a significance level of 5% (a=0.05). Monkeys were able to recognize both MAD20 and K1 types of BVp42 even though two-thirds of the protein differs in amino acid sequence. However, the K/M ratios between individual monkeys varied slightly indicating that there may be slight differences in the specificity of antibody populations produced by individual animals.

Rabbit sera reacted equally well with the heterologous BVp42-K and the homologous BVp42 (Table 2). Antibody titers of BVp42 ranged from $1.21\times10^6$ with rabbit K170 to $2.60\times10^6$ with rabbit K192. BVp42-K titers ranged from $1.38\times10^6$ with rabbit K170 to $2.38\times10^6$ with rabbit K192. The average titer of the five rabbits with BVp42 was $1.71\times10^6$ while the average titer with BVp42-K was $1.88\times10^6$. Like the monkey results, "t" test difference scores show that antibody titers with BVp42 were not significantly different than BVp42-K using a significance level of 5% ($\alpha=0.05$), emphasizing the fact the p42 dimorphism may not play an important role in B cell antigen recognition and antibody specificity. The rabbit K/M ratios were not as varied as the monkey K/M ratios but were similar averaging 1.1 and 1.4 respectively.

Example 5

Comparison of Monoclonal Antibodies

A panel of mouse Mabs made against the p42 region of MSP-1 was used to examine potential conformational differences between BVp42 and BVp42-K. These antibodies have been previously characterized and the areas of BVp42 reactivity established (Kaslow et al. 1993. Mol. Biochem. Parasitol. 63:283-2389). Mabs 4.2, 94-115, AD9.1, BC9.1, 91-33 and 91-115 all recognize conformational epitopes found in the conserved 19 kDa portion of BVp42. G13 is the only Mab found outside of the 19 KDa region and recognizes a linear epitope. Results from western blots with the various Mabs show that all of the antibodies react with both BVp42 and BVp42-K except for G13 (FIGS. 18A and 18B). Western blots show that G13 does not react with BVp42-K even though it has a high affinity for BVp42. Further tests with G13 (data not shown) using an ELISA, indicate that G13 may react very slightly with BVp42-K but not near the extent it reacts with BVp42. This slight cross-reactivity was unexpected since G13's epitope is located in the variable region of the 33 kDa area of BVp42 and was thought to be non-reactive with BVp42-K. Perhaps the dimorphism that exists in the N-terminal portion of the protein makes this epitope only very slightly accessible to G13 or perhaps a similar but not identical epitope exists on BVp42-K.

The positive results obtained with the other Mabs show that, despite its sequence differences at the N-terminus BVp42-K C-terminus seems to have the same general structure as the 19 kDa region of MSP-1. The 19 kDa region corresponding to block 17, which is considered to be a conserved region of MSP-1, contains four amino acid sties that can vary between strains. Antibodies used here (except for G13) recognize the conserved, conformational epitopes of the 19 kDa region (Kaslow et al. supra). This is important since the disulfide bridges found in the 19 kDa region play an important part in the tertiary structure of the protein. More importantly, the polyclonal antibody data presented here and by Hui et al. 1993. Infect. Immun. 61:3403-3411) suggest that the vast majority of BVp42 antibodies are made against the conserved portions of the protein, thus possibly down-playing the role of dimorphism in antibody recognition.

Example 6

Glycosylation Analysis

Visualization of BVp42-K with silver stains and western blots revealed that two forms of the protein were being produced by insect cells. Contamination with BVp42 was easily ruled out because neither form of BVp42-K reacted strongly with Mab G13, while BVp42 reacts strongly with the antibody. Glycosylation tests revealed that both BVp42-M and BVp42-K are glycosylated in the baculovirus expression system. Both silver stains and western blots reveal that digestion of the proteins with N-glycosidase F results in a shift of each of the proteins to a lower molecular weight (FIG. 19A-B). More significantly, incubation of N-glycosidase F with BVp42-K resulted in the resolution of the two form of the protein into one form of a smaller molecular weight. The shift to a lower molecular weight was less dramatic but still significant for BVp42. This difference corresponds to the presence of two potential N-glycosylation sites in the BVp42-K p42 sequence and only one potential N-glycosylation site in the BVp42 construct. Interestingly, this molecular weight shift was not seen in parasite isolated MSP-1, confirming other reports that N-glycosylation may not occur in *P. falciparum* (Blackman et al. 1991. Mol. Biochem. Parasitol. 49:2934; Holder et al. 1992. Mem. Inst. Oswaldo Cruz 87:37-42).

Tunicamycin experiments also supported the presence of N-glycosylation for both proteins in insect cells. Incubation of HIGH FIVE™ cells with tunicamycin during recombinant baculovirus infection with either construct resulted in the same molecular weight shift of the expressed protein as seen with the N-glycosidase F (FIG. 20). Incubation of BVp42-K with other glycosidases (O-glycosidase, β-galactosidase and neuraminidase) did not result in a molecular weight shift of the protein visualized by silver staining.

Example 7

Production and Purification of Yeast p42 (Yp42)

A yeast p42 construct was expressed in the alcohol dehydrogenase 2/glyceraldehyde-3-phosphate dehydrogenase ($ADH_2$-GAPDH) regulated expression system of *Saccharomyces cerevisiae* and has been described fully in Hui et al. 1991. J. Immunol. 147:3935-3941, expressing incorporated by reference. The p42 construct was based on the gp195 coding region from $Ala_{1333}$ to $Ser_{1705}$ of the FUP isolate (Chang et al. 1988. Exp. Parasitol. 67:1). The yeast p42 polypeptide (Yp42) was purified using an affinity chromatography technique described by Siddiqui et al. 1987 for the purification of parasite gp195, except that polyclonal rabbit anti-gp195 IgG was used for antigen purification instead of anti-gp195 Mab 5.2, because the Yp42 protein could not be recovered in significant amounts using this Mab.

FIG. 2B shows silver stains (lane 1) and immunoblots (lane 2) of the affinity chromatography purified Yp42. The silver stained antigens were electrophoresed in SDS polyacrylamide gels. The immunoblots were reacted with a rabbit anti-parasite gp195 serum pool. In the silver stain, a major species corresponding to Yp42 migrated as a 44 kDa molecule, although other minor bands were also present in varying amounts. In the immunoblots, the purified Yp42 displayed major immunoreactive species at the positions of the major protein bands, accompanied by minor reactivities with proteins of higher and lower molecular weight.

Example 8

Isolation of Purified, Parasite gp 195 with Selected Fragments that Induce Substantially Complete Protection Against *Plasmodium falciparum* Challenge A mixture of gp195 protein and certain of its processing fragments were obtained from in vitro cultured parasites (*P. falciparum* Uganda Palo Alto strain) using monoclonal-antibody affinity chromatography procedures employing Mab 5.2 (Siddiqui et al. 1987); i.e. the mixture is enriched in the epitope for which Mab 5.2 is specific. Importantly, this mixture has been previously shown to be capable of inducing substantially complete protection against a homologous challenge of *Plasmodium falciparum* in Aotus monkeys (Siddiqui et al. 1987). References in the examples below to "gp195" refer to the Mab 5.2-purified mixture of gp195 enriched with certain of its processing fragments.

In summary, saponin-lysed parasites were extracted with 1% NP-40 and the lysate was clarified by ultracentrifugation. The extracts were passed through a Protein G Sepharose column covalently conjugated with gp195-specific Mab 5.2

(U.S. Pat. No. 4,897,354: expressly incorporated by reference and deposited with the American Type Culture Collection, 12301 Parklawn Drive, Rockville, Md., USA 20852, on Jul. 17, 1986 under accession number HB 9148). Mab 5.2 is specific for an antigenic determinant contained in p42, as demonstrated below.

After extensive washing to remove non-specifically bound material, specifically-bound proteins were eluted with 0.1 M glycine (pH 2.5) and neutralized with 1 M Tris-HCl (pH 8.0). The purity of the isolated gp 195 was examined by SDS-PAGE followed by silver staining.

Example 9

In Vitro Inhibition Assay

Substantially complete parasite inhibition was found obtainable using BVp42 as an immunogen in in vitro parasite growth inhibition assays. This level of inhibition has only been observed by us to be induced by the Mab 5.2 affinity-purified mixture of gp195 and fragments (Hui et al. 1987. Exp. Parasitol. 64:519). In vitro parasite growth inhibition assays were performed by culturing parasites in the presence of immune rabbit serum using established methods (Hui et al. 1987. Exp. Parasitol. 64:519). Briefly, parasites were cultured in the presence of 15% preimmune serum or immune rabbit serum obtained 14, 21, 28, and 35 days after the fourth immunization with BVp42 in Complete Freund's Adjuvant (indicated as 4D14, 4D21, 4D28 and 4D35 in Table 3). The starting parasitemia (S) in each of the experiments was 0.2%. Growth inhibition was calculated according to the following equation:

$$\% \text{ inhibition} = \frac{(P - S) - (T - S)}{(P - S)} \times 100 \%, \text{ where}$$

P=% parasitemia of cultures containing 15% preimmune serum at 72 hours;

T=% parasitemia of cultures containing 15% immune serum at 72 hours; and

S=starting % parasitemia of cultures at 0 (zero) hours.

Quaternary sera were used in inhibition assays. The corresponding pre-immune serum of each animal was used as a control. Parasite cultures were synchronized by sorbitol lysis (Lambros et al. 1979. J. Parasitol. 65:418) to select for late trophozoite and schizont stages. Infected erythrocytes were adjusted to an initial parasitemia of approximately 0.2% and a hematocrit of 0.8% with fresh erythrocytes. Rabbit preimmune or immune serum was added to a final concentration of 15%, and 200 µl of the culture suspension were added-in duplicate wells to a 96-well microtiter plate. Cultures were incubated at 37° C. for 72 hours, and the parasitemia was determined by microscopy. The experiment was repeated three times for each of the rabbits used (rabbits given identification nos. 131 and 132). Results are shown in Table 3.

Quaternary sera of rabbits immunized with Yp42 had no significant effect on in vitro parasite growth (data not shown). In contrast, significant inhibition was obtained with quaternary sera of several bleeding dates from both rabbits immunized with BVp42 (Table 3). Sera obtained from later bleedings of rabbit 132 (4D21, 4D28, 4D35) nearly completely inhibited parasite growth; similar levels of inhibition have been observed previously only with antisera against Mab 5.2 purified, parasite gp195 (Hui et al. 1987).

TABLE 3

In Vitro Parasite Growth Inhibition Assay with Rabbit Anti-BVp42 Sera

| Rabbit Serum | % Parasitemia (% Inhibition) | | |
|---|---|---|---|
| | Expt. 1 | Expt. 2 | Expt. 3 |
| Anti-BVp42 (131): | | | |
| Preimmune | 13.3 | 6.8 | 9.8 |
| 4D14 | 10.3 (23) | — | — |
| 4D21 | 5.6 (58) | 3.9 (44) | 4.0 (60) |
| 4D28 | — | 1.7 (77) | 2.6 (75) |
| 4D35 | — | 1.6 (79) | 1.9 (82) |
| Anti-BVp42 (132): | | | |
| Preimmune | 9.0 (11) | 6.7 | 8.7 |
| 4D14 | 5.4 (47) | — | — |
| 4D21 | <0.1 (>99) | 0.4 (98) | 0.2 (100) |
| 4D28 | — | 0.3 (98) | 0.3 (99) |
| 4D35 | — | 0.3 (98) | 0.9 (92) |

Example 10

Determination of Immunogenicities and Cross-Reactivities of Recombinant Polypeptides A. ELISA Titers of Rabbits Immunized with Purified Parasite gp195 Against gp195, BVp42 and Yeast p42.

Rabbits were immunized with BVp42, Yp42 or enriched gp195 mixture (i.e. enriched for gp195 and C-terminal containing processing fragments through Mab 5.2 affinity purification) to determine the immunogenicity of the recombinant polypeptides and the cross-reactivity of anti-recombinant p42 antibodies with native gp195.

Rabbits given identification nos. 103, 104, 106 and 115 were immunized with purified, parasite gp195 emulsified in Complete Freund's Adjuvant as described (Hui et al. 1987). Rabbits 131 and 132 were immunized intramuscularly four times at 21-day intervals with 50 µg of purified BVp42 in Complete Freund's Adjuvant. Rabbits 93 and 96 were immunized intramuscularly five times at 21-day intervals with 50 µg of purified Yp42 in Complete Freund's Adjuvant. The amount of mycobacteria was reduced to one half of the first dose for the second immunization and one fourth of the first dose for subsequent immunizations, with the volume being replaced with Incomplete Freund's Adjuvant. Rabbits were bled before immunization and weekly after each immunization.

Serum antibodies produced against enriched gp 195 mixture, BVp42, or Yp42 were assayed by an enzyme-linked immunosorbent assay (Chang et al. 1989; Chang et al. 1988) using the following technique. Vinyl plates were coated with purified, parasite gp195 and fragments (0.08 µg/ml), recombinant BVp42 (0.08 µg/ml), or recombinant Yp42 (0.2 µg/ml) and washed and blocked with 1% bovine serum albumin in borate buffered saline (BBS: 167 mM borate/134 mM NaCl, pH 8.0). Rabbit and mouse sera were serially diluted in 1% BSA/BBS, and human sera were serially diluted in phosphate-buffered saline (PBS: 150 mM sodium phosphate, 500 mM NaCl, pH 7.4) containing 0.05% Tween 20, 1.5% powdered milk, 0.05% BSA and 0.05% thimerosal. Diluted sera were added to antigen-coated wells and incubated for 1 hr at room temperature. Plates were washed with BBS containing 0.5 M NaCl (HSBBS) (rabbit and mouse sera) or PBS with 0.05% Tween 20 (human sera), and an appropriate dilution of peroxidase-conjugated species-specific anti-IgG (heavy and light chain specific) was added and incubated for 1 hr (anti-rabbit and anti-mouse IgG) or 2 hrs (anti-human IgG) at room temperature. Plates were washed in HSBBS and finally in BBS. One hundred microliters of peroxidase substrate solution [$H_2O_2$ and 2,2'-azino-bis(3-ethylbenzothiazoline-6-sulfonate)] were added to each well, and the absorbance value at 410 nm was determined with a Dynatech 605 ELISA reader. The endpoint of ELISA titers for rabbit sera was designated to be the serum dilution producing an absorbance value of 0.2, which corresponded to twice the background O.D. reading. The ELISA endpoint titers for human sera was designated to be the serum dilution producing an absorbance value greater than 0.056, which was two standard deviations above the average reading for normal human sera.

A comparison of the reactivity of the polyclonal antisera from rabbits immunized with the purified, enriched parasite gp195, BVp42, and Yp42 in an ELISA is shown in Table 4.

TABLE 4

ELISA Titers of Rabbits Immunized with Purified, Parasite gp195 Against Parasite gp195, Baculovirus p42, and Yeast p42

| Rabbit Serum | gp195 Titer | BVp42 Titer | Yp42 Titer |
|---|---|---|---|
| 103 | 1/140,000 | 1/5,400 | 1/1,000 |
| 104 | 1/300,000 | 1/7,000 | 1/1,300 |
| 106 | 1/330,000 | 1/20,000 | 1/3,000 |
| 115 | 1/160,000 | 1/4,200 | 1/800 |

The highest ELISA titers were obtained against parasite gp195, the immunogen, with lower titers against BVp42, and the lowest titers against Yp42. These results are consistent with the expectation that antibodies are induced by gp 195 outside of the p42 fragment, leading to a higher titer against the gp195 preparation than against BVp42.

B. ELISA and IFA Titers of Rabbits Immunized with BVp42 and Yeast p42 Against Parasite gp195, BVp42 and Yp42.

Additional rabbits were immunized with purified BVp42 (nos. 131, 132) or purified Yp42 (nos. 93, 96) to determine the immunogenicity of the recombinant polypeptides and the cross reactivity of anti-recombinant p42 antibodies with native gp195. Rabbit sera were tested by ELISA, parasite indirect immunofluorescence (IFA), and immunoblotting with parasite gp195.

The IFA procedure used was as follows. Assays were performed on acetone-fixed thin blood smears of schizonts and merozoites as described (Siddiqui et al. 1986. Infect. Immun. 52:314). Endpoint IFA titers corresponded to the final serum dilution producing parasite immunofluorescence above background levels observed using preimmune rabbit sera.

Sera were obtained on the day indicated (day 14, 21, 28 or 35, indicated as 4D14, etc. in Table 5 below) after four immunizations of rabbits with 50 µg BVp42 or 50 µg Yp42. Serial dilutions of sera were titered for reactivity with plates coated with recombinant p42 (rp42) or parasite gp195. "rp42" corresponds to BVp42 for rabbit anti-BVp42 sera and Yp42 for rabbit anti-Yp42 sera. The method of determining the ELISA endpoint titer for rabbit sera was as discussed above. Endpoint IFA titers correspond to the final serum dilution producing parasite immunofluorescence above preimmune serum backgrounds.

BVp42 proved to be highly immunogenic as shown in Table 5, inducing antibody titers comparable to those of rabbits immunized with purified, parasite gp195 (Table 2).

As shown in Table 5, ELISA titers were similar in assays utilizing plates coated with either purified, parasite gp195 or BVp42. Very high ELISA titers were obtained late in the quaternary response (days 28 and 35). Yp42 was less immunogenic than BVp42, inducing lower antibody titers against the immunogen. In addition, the cross-reactivity of anti-Yp42 antibodies with parasite gp195 in the ELISA was much lower than the cross-reactivity of anti-BVp42 antibodies. Typical merozoite surface staining patterns were observed by IFA for the BVp42 antisera (data not shown), and IFA titers obtained after the fourth immunization (Table 5) reached levels exceeding those obtained by immunization with purified, parasite gp 195 (data not shown). Yp42 induced much lower IFA titers.

C. ELISA Inhibition Assay

In order to obtain an estimate of the degree of cross-reactivity of anti-parasite gp 195 (enriched mixture) antibodies with BVp42 and Yp42, we performed an ELISA inhibition assay utilizing the various antigens as inhibitors. The ELISA inhibition assay measures the reduction in reactivity of anti-parasite gp195 sera with parasite gp195 antigen in the presence of various concentrations of soluble parasite gp195 or recombinant p42. The ELISA inhibition assay was performed by diluting rabbit antisera to a point on the descending portion of the ELISA titration curve. The diluted sera (rabbit anti-parasite gp195 sera 103, 104, 106, and 115) were mixed with various concentrations of inhibitor (gp195, BVp42, or Yp42), incubated for 1 hour, and added to purified, parasite gp195-coated plates. Subsequent steps in the ELISA inhibition assay were identical to the standard ELISA assay described in section A above.

TABLE 5

ELISA and IFA Titers of Rabbits Immunized with Baculovirus p42 and Yeast p42 Against Parasite gp195, Baculovirus p42 and Yeast p42

| Rabbit Serum | rp42 ELISA Titer | Gp195 ELISA Titer | IFA Titer |
|---|---|---|---|
| Anti-BVp42 (131): | | | |
| 4D21 | 1/100,000 | 1/30,000 | 1/25,600 |
| 4D28 | 1/120,000 | 1/130,000 | 1/51,200 |
| 4D35 | 1/98,000 | 1/160,000 | 1/204,800 |
| Anti-BVp42 (132): | | | |
| 4D21 | 1/74,000 | 1/85,000 | 1/51,200 |
| 4D28 | 1/120,000 | 1/300,000 | 1/102,400 |
| 4D35 | 1/88,000 | 1/300,000 | 1/204,800 |
| 4D14 | 1/60,000 | 1/2,000 | 1/1,600 |
| 4D21 | 1/40,000 | 1/2,000 | 1/3,200 |
| 4D28 | 1/50,000 | 1/3,000 | 1/6,400 |
| Anti-Yp42 (96) | | | |
| 4D14 | 1/25,000 | 1/900 | 1/800 |
| 4D21 | 1/23,000 | 1/800 | 1/3,200 |
| 4D28 | 1/30,000 | 1/700 | 1/6,400 |

The results are shown in FIG. 4. Soluble parasite gp195 completely inhibited the binding of anti-gp 195 sera in this assay. A high level of inhibition (82-92%) was also obtained with soluble BVp42. Much lower levels of inhibition were seen with soluble Yp42 (28-47%). The average antigen concentration required to obtain 50% inhibition in The ELISA was similar for parasite gp195 (0.03 µg/ml) and BVp42 (0.04 µg/ml), while >5 µg/ml Yp42 was required for 50% inhibition. These results suggest that a majority of antibodies against parasite gp195 also recognize BVp42, i.e. purified, parasite gp195 and BVp42 are highly cross-reactive.

D. Reactivity with Human Sera

The recognition of gp195 (without Mab 5.2 affinity purified fragments) and related recombinant polypeptides by serum antibodies of individuals from a malaria-endemic area of the Philippines have been analyzed by Kramer and Oberst. Several individuals from this study were examined for antibody reactivity with parasite gp195 (Mab 5.2 affinity purified), BVp42 and Yp42. The results are shown in Table 6

TABLE 6

Reactivity of Human Sera from a Malaria-Endemic Area with Purified, Parasite gp195, the Baculovirus p42 Polypeptide, and the Yeast p42 Polypeptide

| Individual | gp195 ELISA Titer | BVp42 ELISA Titer | Yp42 ELISA Titer |
|---|---|---|---|
| 14270 | 1/100 | 1/200 | neg. |
| 14103 | 1/102,400 | 1/51,200 | 1/400 |
| 14122 | 1/102,400 | 1/51,200 | 1/400 |
| 14184 | 1/3,200 | 1/3,200 | 1/800 |
| 13563 | 1/200 | 1/1,600 | neg. |
| 13691 | 1/51,200 | 1/12,800 | 1/200 |
| 14187 | 1/21,800 | 1/12,800 | 1/100 |

Serial serum dilutions were tested for reactivity with the plates coated with parasite gp195, BVp42 and Yp42. Endpoint titers were designated as the serum dilution producing an O.D.>0.056, which was two standard deviations above the average reading for normal human sera. There was an excellent correlation between ELISA titers obtained with parasite gp195 and BVp42 (Pearson's correlation coefficient r=0.96, p<0.001). A lower correlation was obtained for gp195 and Yp42 ELISA titers (Pearson's correlation coefficient r=0.86, p<0.01). Thus, BVp42 cross reacts with serum antibodies of humans from the malaria endemic area of the Philippines.

E. Recognition of Conformational Determinants by Antibodies of Rabbits Immunized with Parasite gp195 and Recombinant p42 and by a gp195 specific, Mab 5.2.

FIG. 3, Panels A and B show immunoblots of purified parasite gp195 electrophoresed under nonreducing (panel A) or reducing (panel B) conditions in a 11.5% SDS-polyacrylamide gel. Immunoblots were reacted with the following antibody preparations: lane 1, anti-gp195 Mab 5.2; lane 2, rabbit anti-parasite gp195; lane 3, rabbit anti-BVp42 (#131); lane 4, rabbit anti-BVp42 (#132); lane 5, rabbit anti-Yp42 (#93); lane 6, rabbit anti-Yp42 (#96). Panel C: Immunoblots of BVp42 (lane 1, non-reduced; lane 2, reduced) and Yp42 (lane 3, non-reduced; lane 4, reduced) reacted with Mab 5.2.

The procedure for immunoblotting was as follows. Purified gp195 and BVp42 polypeptides were dissolved in Laemmli's buffer with or without 2-mercaptoethanol as a reducing agent and separated on NaDodSO$_4$ polyacrylamide gels (Laemmli. 1970. Nature 227:680). The separated proteins were electrophoretically transferred to nitrocellulose (Towbin et al. 1979. Proc. Natl. Acad. Sci. USA 76:4350) and reacted with rabbit and mouse antisera as described by Chang et al., 1989.

FIGS. 3A-B, lane 1, show that Mab 5.2 is specific for a conformational determinant of the p42 fragment of gp195 since reactivity with this antibody was diminished by reduction of the parasite antigen. FIG. 3B lanes 2, 3, and 4 also demonstrates that reactivity with the p42 processing fragments of both anti-gp 195 sera and anti-BVp42 sera was markedly decreased when parasite gp 195 was electrophoresed under reducing conditions. This indicates that both these antisera primarily recognize disulfide, conformational determinants of parasite gp195. In contrast, reactivity of anti-Yp42 sera, as shown in FIG. 3B (lanes 5 and 6) was slightly enhanced for reduced gp195, and the reduced 19 kDa processing fragment was recognized by these sera. Thus, the anti-Yp42 appears to recognize gp195 epitopes that are not disulfide-dependent.

The strong reactivity of BVp42 with Mab 5.2, as shown in FIG. 3C, lane 1, and the loss of this reactivity by reduction of BVp42, as shown in FIG. 3C, lane 2, indicates that the conformation of BVp42 closely resembles that of the native protein.

Example 11

Recognition of BVp42 by Antibodies from Congenic Mouse Strains

It has previously been shown that responsiveness to purified, parasite gp195 is present in mice of diverse major histocompatibility complex makeup (Chang et al. 1989). We determined whether the BVp42 antigen would be similarly recognized by anti-gp195 antibodies from a panel of congenic mouse strains.

Figure 5:
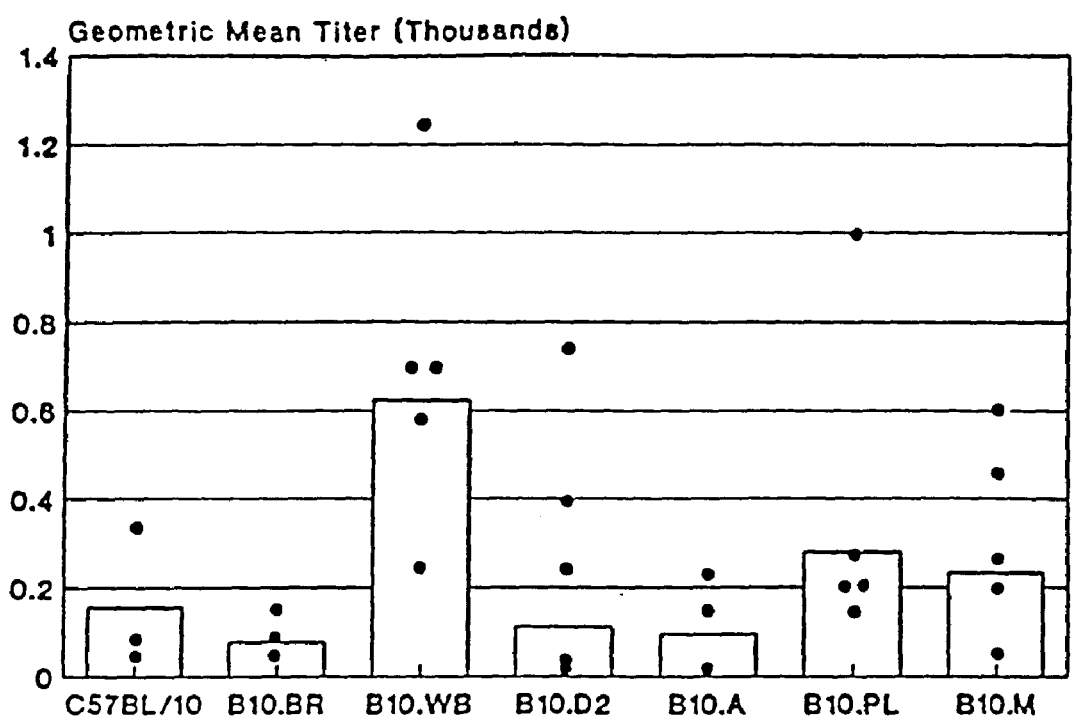
FIG. 5 is a graph showing ELISA titers against a BVp42 antigen of anti-parasite gp195 sera of congenic mice.
Figure 8A:
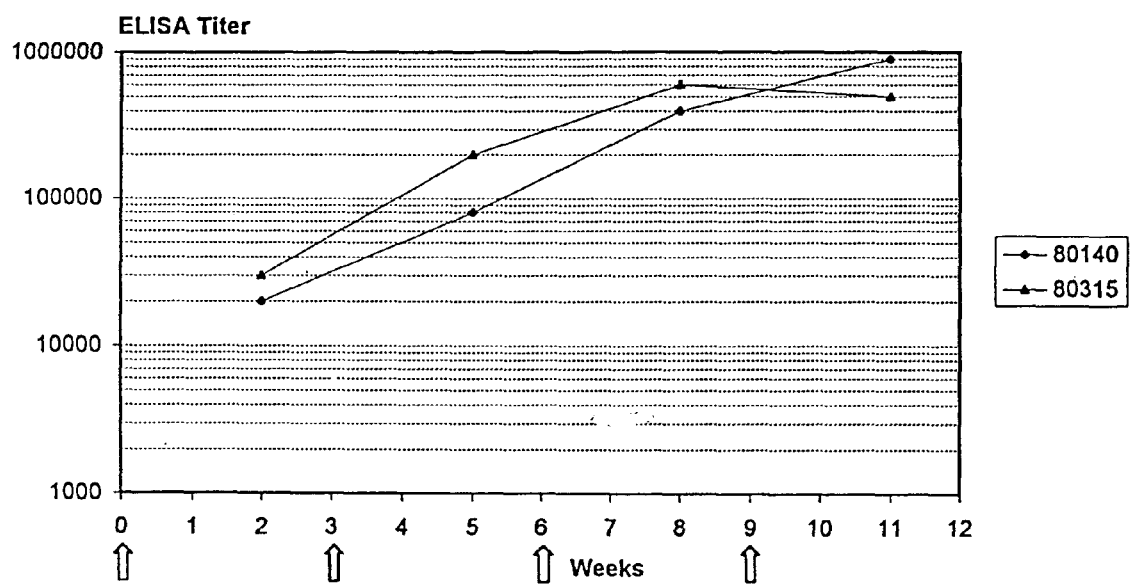
FIGS. 8A-D show the ELISA titer of *Aotus* monkeys immunized with BVp42 adjuvant preparations. ELISAs were performed as described by Chang et al. 1989. The endpoint of ELISA titers for *Aotus* sera was determined as the X-axis intersection of the ELISA titration curve.
Figure 8B:
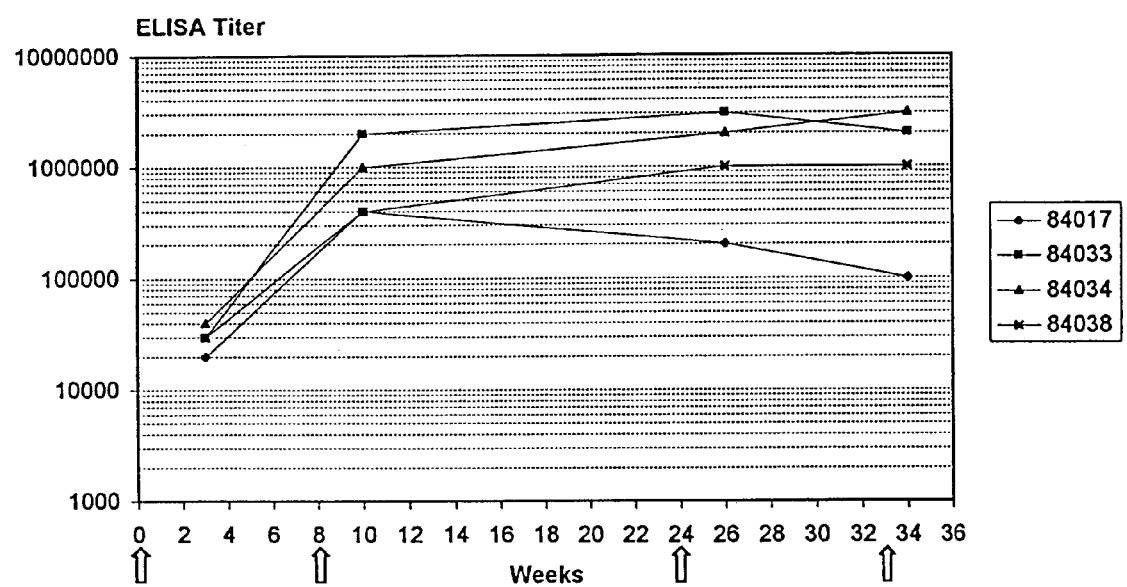
Figure 8C:
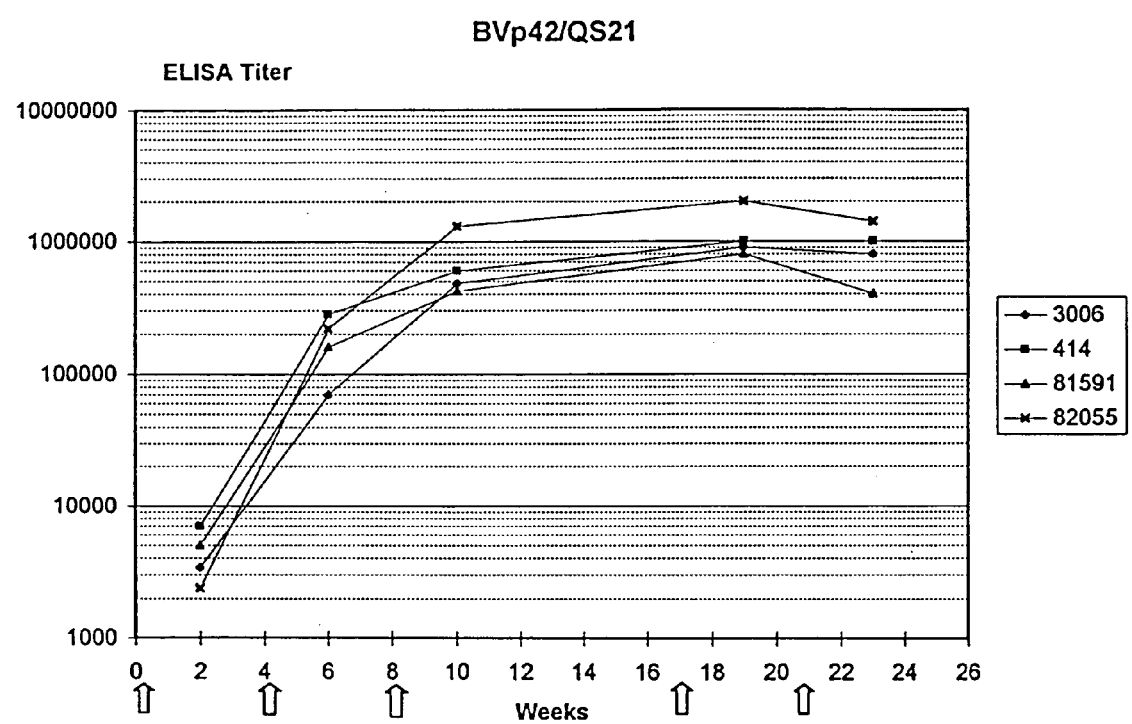
Figure 8D:
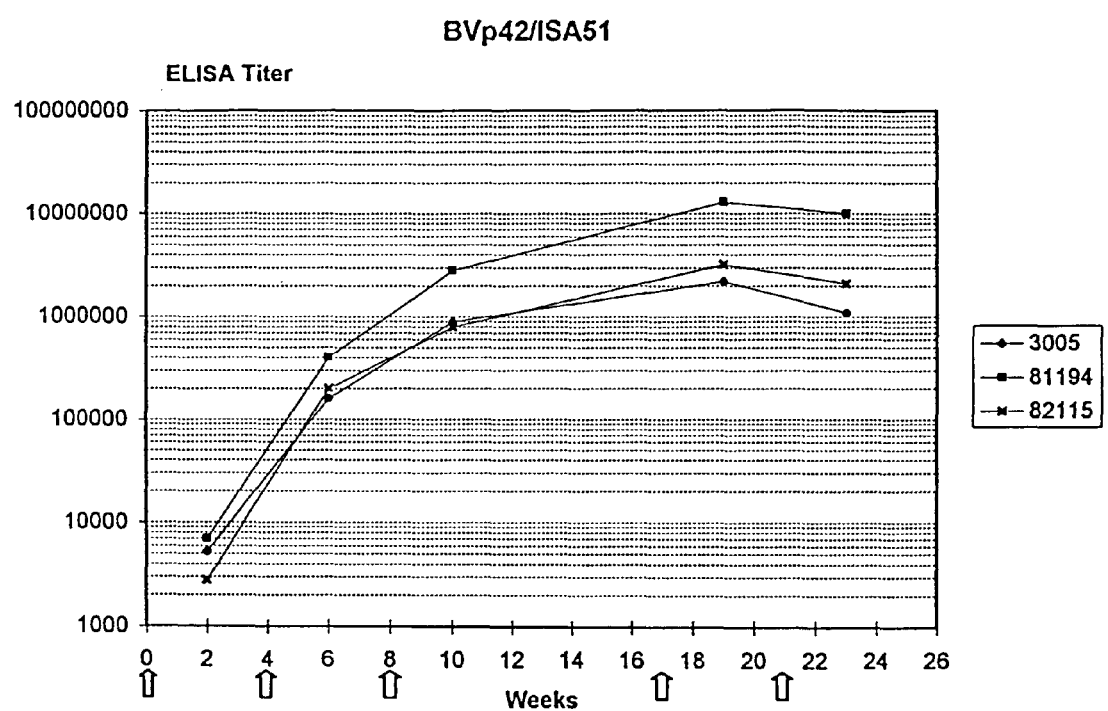

Sera of seven congenic mouse strains possessing different H-2 haplotypes on the B 10 background and that had been immunized with purified, parasite gp195 were tested for reactivity with the BVp42 antigen (FIG. 5). Congenic mice of the following strain designations differing in H-2 haplotype but sharing the C57BL/10 genetic background were immunized: C57BL/10 SnJ, B10.A/SgSnJ, B10.D2/nSnJ, B10.M/SN, B10.WB (69NS), B10.BR/SgSnJ, and B10.PL (Jackson Laboratories, Bar Harbor, Me.). Five mice per group were immunized intraperitoneally four times at 2-week intervals with 5 µg of purified, parasite gp195 emulsified in Complete Freund's Adjuvant. Mice were bled before immunization, on days 7 and 10 after the first immunization and on days 5, 7, and 14 after subsequent immunizations.

All seven strains produced anti-gp195 antibodies recognizing epitopes of BVp42 with some variation in titer among strains. Thus, similar to parasite gp195, individuals of diverse MHC haplotypes are capable of producing antibodies recognizing BVp42.

Example 12

Reactivity of Anti-BVp42 with Homologous vs. Heterologous Antigens

Since the gp42 processing fragment contains both conserved and allelic determinants, the reactivity of anti-BVp42 antibodies with homologous vs. heterologous gp195 antigens was characterized. Four parasite isolates, FUP, FVO, Hond-1 and Pf857 were used and by Southern blot analyses with allele specific oligonucleotide probes showed that FUP and Pf857 belong to the MAD allele, and FVO and Hond-1 belong to the K1 allele. Native gp195 antigens were purified by affinity chromatography from FUP and FVO parasites. In ELISAs, identical titers and binding curves were obtained with anti-BVp42 antibodies using either FUP (homologous) or FVO (heterologous) gp195 as antigens. Similar results were obtained in indirect immunofluorescent assays with FVO and FUP merozoites. More importantly, anti-BVp42 antibodies strongly or completely inhibited the in vitro para-

Example 13

Immunogenicity of Various Adjuvant Formulation of BVp42 in Aotus monkeys Aotus lemurinus griseimembra monkeys of karyotypes II and III with no history of previous *P. falciparum* exposure were screened for lack of BVp42 antibody reactivity by enzyme-linked immunosorbent assay (ELISA), the ability of the sera to support in vitro growth of plasmodia, normal blood chemistry and hematology values, absence of blood and intestinal parasites, absence of cardiovascular abnormalities and overall good health. *Aotus* monkeys passing this screening process were stratified by gender before being randomly assigned to the control or experimental groups. All animals were maintained at the University of Hawaii Laboratory Animal Service facility in accordance with National Institutes of Health and institutional guidelines.

The recombinant BVp42 antigen is based on the C-terminal merozoite surface protein-I (MSP 1) sequence of the Uganda-Palo Alto *P. falciparum* isolated (FUP) (Chang et al. 1988) which is closely related to the MAD20 MSP1 allele. BVp42 corresponds to the p42 coding region from $Ala_{1333}$ to $Ser_{1705}$ cloned into the *Autographica californica* nuclear polyhedrosis virus polyhedron promoter-regulated expression system (Luckow et al. 1988). A similar construct, designated BVp42-K, was generated consisting of the corresponding p42 coding region of the Vietnam-Oak Knoll isolate which is closely related in sequence to the Wellcome-K1 MSP1 allele (T. Nishimura, unpublished data). The recombinant p42 polypeptides were isolated from culture supernates of baculovirus infected *Trichoplusia ni* cells by immuno-affinity chromatography as previously described (Siddiqui et al. 1987). BVp42 purity was assessed by silver staining of antigen preparations separated by polyacrylamide gel electrophoresis.

Native MSP-1 protein and its processing fragments were purified from in vitro cultured parasites by immuno-affinity chromatography (Siddiqui et al. 1987).

Immunizations consisted of 100 µg of BVp42 in 0.25-0.5 ml of bacteriostatic 0.9% saline solution (Abbott Laboratories, North Chicago, IL) formulated with the adjuvants: MF59 (Chiron Corporation), MTP-PE (CIBA-Geigy), STIMULON™ QS21 (Aquila Biophamaceuticals), or MONTANIDE™ ISA51 oil-in water emulsion (Seppic Inc.) according to the manufacturers instructions. In the case of MF59, immunizations were administered on weeks 0, 3, 6 and 9. An extended immunization protocol was used for MTP-PE+MF59 (MTP-PE: mutamyl tripeptide covalently linked to dipalmitoyl phosphatidyl ethanolamine; MF-59: and oil-in-water emulsion containing squalene, polysorbate 80 (Tween-20), sorbian trioleate (Span85), and thimersol) for which immunizations were administered on weeks 0, 8, 24 and 33. Monkeys received 200 µg MTP-PE in 0.5 ml MF-59 for each immunization (Keitel et al. 1993. Vaccine 11:9090-913). For both QS-21 and ISA51 formulations, immunizations were given on weeks 0, 4, 8, 17, and 21. Each dose was given intramuscularly into alternating left and right thigh areas. In the first experiment, approximately 3 ml blood samples were collected from the femoral vein 14 days after each immunization and, for experiment 2, blood samples were collected monthly between the secondary and tertiary immunizations. Unimmunized animals or animal immunized with adjuvant alone served as controls.

TABLE 7

Experimental Groups Receiving various Adjuvant Formulation of the BVp42 Merozoite Surface Protein 1 Vaccine

| Adjuvant Group | Adjuvant | Animal Nos. |
|---|---|---|
| I | MF-59 | 80140, 80315 |
| II | MTP-PE + MF-59 | 84017, 84033, 84034, 84038 |
| III | QS21 | 3006, 414, 81591, 82055 |
| IV | Montanide ISA-51 | 3005, 81194, 82115 |

All of the adjuvant formulations tested were generally well tolerated and produced no systemic side effects in vaccinated monkeys. Local effects produced from immunization with BVp42/MF-59 included persistent induration at the site of injection and enlarged inguinal lymph nodes. Animals immunized with BVp42/MTP-PE+MF59 also developed enlarged inguinal lymph nodes but no induration at the site of injection. No local effects were observed at the site of injection or in the area of the regional lymph nodes for the BVp42/QS21 and BVp42/ISA51 formulations.

FIGS. 8A-D present the kinetics of the antibody response to BVp42 induced by immunization with the various adjuvant formulations. Significant boosting of antibody titer was observed after the second immunization with all four adjuvant formulations. Boosting was more variable after subsequent immunizations. For BVp42 in MF59, the peak titer for one animal (80315) was obtained after the third immunization while the titer for another animal (80140) continued to increase after the fourth immunization. Similarly, animals immunized with BVp42 in the MTP-PE+MF59 formulation developed peak titers after the third or fourth immunization although the titer of one animal (84017) reached its maximum after two immunizations, declining somewhat with subsequent immunizations. All of the animals immunized with BVp42/QS21 or BVp42/ISA51 continued to develop increased antibody levels with repeated immunization and achieved peak antibody titers after four immunizations.

Figure 9:
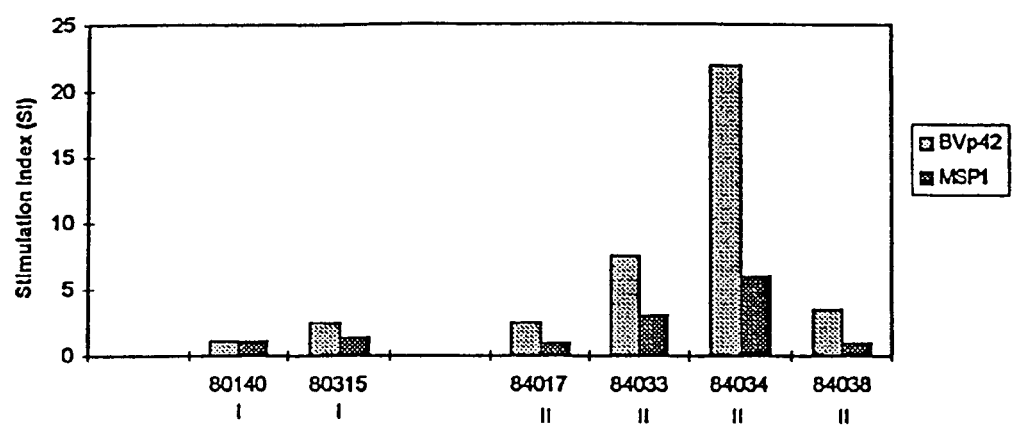
FIG. 9 shows the results of a T-cell proliferation assay of mononuclear cell cultures of *Aotus* vaccinated with BVp42 and either MF59 (I) or MTP-PE+MF-59 (II).
Figure 10A:
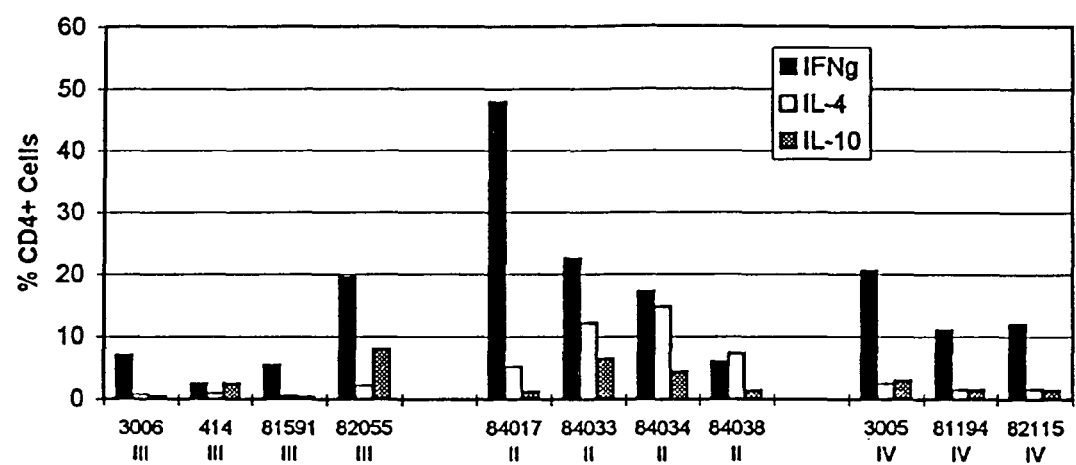
FIG. 10A shows the results of intracellular cytokine producing cells of unstimulated cultures of *Aotus* vaccinated with BVp42 in adjuvants QS21 (III), MTP-PE+MF59 (II), or ISA51 (IV). IFNγ: interferon-gamma; IL-4: interleukin-4; IL-10: interleukin-10.
Figure 10B:
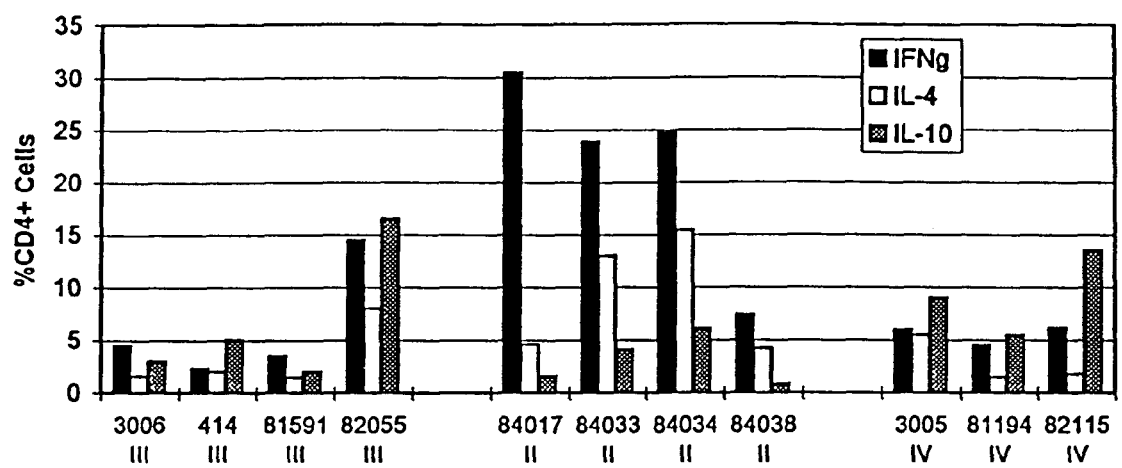
FIG. 10B shows the results of intracellular cytokine producing cells of BVp42 stimulated cultures of *Aotus* vaccinated with BVp42 in adjuvants QS21 (III), MTP-PE+MF59 (II), or ISA51 (IV). IFNγ: interferon-gamma; IL-4: interleukin-4; IL-10: interleukin-10.

The cell mediated immune response induced by immunization was assessed by either antigen specific T-cell proliferation assays (FIG. 9) or by the measurement of cytokine producing cells in antigen-stimulated and unstimulated T-cell cultures (FIGS. 10A-B). Significant antigen-specific T-cell proliferation was observed for peripheral blood mononuclear cell cultures of animals injected with the three formulations tested using this assay (FIG. 9: Groups I, II). Since cytokine production may be more informative than T-cell proliferation in assessing the type of T-cell response induced by the various adjuvant formulations, we also evaluated intracellular cytokine production in subsequent vaccination studies. Peripheral blood of *Aotus* receiving adjuvant formulations II, III, and IV contained high number of interferon-gamma (IFNγ) producing cells (FIG. 10A). Significant numbers of IL-4 and IL-10 producing cells were also detected in unstimulated peripheral blood CD4+ cells.

Effectiveness of T cell priming with the two adjuvant formulations, BVp42/ISA51 and BVp42/QS21, was evaluated by enumeration of intracellular cytokine producing cells of these animals that were unstimulated and BVp42 stimulated in vitro (Table 8). Prior to initiation of immunization, the level of cytokine-producing cells in all animals were <1% for IL-4 and IL-10 and 2% for IFNγ. Following immunization, significantly enhanced levels of cells producing the Th1 cytokine IFNγ and the Th2 cytokines IL-4 and IL-10 were detected in all immunized animals.

For animals immunized with BVp42/ISA51, a high percentage of IFNγ-producing cells (11-21%) were detected in unstimulated lymphocyte cultures of primed animals, indicating that immunization with this formulation induced an increase in peripheral blood cells producing this Th1 cytokine. Production of IL-10 was enhanced in BVp42-stimulated cultures as compared to cultures incubated without antigen, indicating that Antigen-specific, primed T cells included a significant Th2, IL-10-producing component that could be expanded by BVp42 stimulation. In the other BVp42-stimulated cultures, the percentage of cytokine producing cells either remained the same (IL-4) or was slightly reduced (IFNγ) as compared to unstimulated cultures containing no antigen.

In the case of *Aotus* immunized with BVp42/QS21, IFNγ was also the predominant cytokine for most animals in terms of percentage of cytokine producing cells in unstimulated cultures. However, both IL-4 and IL-10 producing cells were enhanced upon antigen stimulation in vitro, consistent with effective priming of the Th2 antigen-specific population with this formulation.

TABLE 8

Cytokine Production in Aotus Vaccinated with BVp42 Adjuvant Formulations

| Sample | Unstimulated | | | BVp42-stimulated | | |
|---|---|---|---|---|---|---|
| | IFNγ | IL4 | IL10 | IFNγ | IL4 | IL10 |
| BVp42/ISA51 | | | | | | |
| 3005 | 20.5[a] | 2.5 | 3 | 6 | 5.5 | 9 |
| 81194 | 11 | 1.5 | 1.5 | 4.5 | 1.5 | 5.5 |
| 82115 | 12 | 1.6 | 1.4 | 6.2 | 1.8 | 13.5 |
| BVp42/QS21 | | | | | | |
| 414 | 2.5 | 1 | 2.5 | 2.3 | 2 | 5.1 |
| 3006 | 7 | 0.8 | 0.5 | 4.5 | 1.6 | 3 |
| 81591 | 5.5 | 0.6 | 0.4 | 3.5 | 1.5 | 2 |
| 82055 | 19.5 | 2.2 | 8 | 14.5 | 8 | 16.5 |

[a]numbers correspond to the % CD4+ cells

In summary, the cytokine data indicate that both BVp42 adjuvant formulations induced priming of Th1- and Th2-like lymphocyte populations in vaccinated *Aotus*. While Th1-like IFNγ-producing cells comprised a major population of circulating lymphocytes in these animals, induction of antigen-specific Th2 cells producing IL-4 and IL-10 were also effectively induced with these formulations.

Example 14

In Vitro Inhibition by Sera from *Aotus* Vaccinated with BVp42 Adjuvant Formulations Purified serum immunoglobulin of *Aotus* immunized with the various adjuvant formulations were evaluated for biological activity in an in vitro assay of *P. falciparum* growth inhibition (Chang et al., Inf. Immun. 64:253-261, 1996). The results of two separate experiments are presented in Table 9. Preimmune immunoglobulin of all *Aotus* tested had no effect on in vitro parasite growth. A high level of growth inhibition (94.3% and 92.3%) was observed for the animal displaying the highest level of protective immunity, *Aotus* 81194, which was immunized with BVp42 in ISA51. A lower level of inhibition (82115) was noted for a second animal immunized with BVp42/ISA51 (*Aotus* 82115) although this animal showed no in vivo evidence of protective immunity. The third animal immunized with the BVp42/ISA51 formulation (*Aotus* 3005) showed a low level of inhibitory activity in one of the two experiments. *Aotus* immunized with the BVp42/QS21 formulation did not appear to produce significant levels of inhibitory antibodies as only low levels of inhibition were noted and inhibition was not consistent in duplicate experiments. These results suggest that the in vitro growth inhibition assay may be used as a marker to identify individuals with a high level of immunity, as reflected by high levels of growth inhibition of immunoglobulin from *Aotus* 81194, and this may reflect one mechanism of protective immunity. However, this mechanism does not appear to be itself sufficient nor essential for protective immunity since (1) one animal displaying a detectable (albeit lower than 81194) level of inhibition showed no evidence of protection against parasite infection, and (2) several animals showing partial protection against parasite infection (81591 and 3005) did not show significant or consistent inhibition of in vitro parasite growth.

TABLE 9

In vitro Inhibition by Sera from Aotus Vaccinated with BVp42 Adjuvant Formulations

| Animal No. (Vaccine Formulation) | | Expt #1* | | Expt. #2* | |
|---|---|---|---|---|---|
| | | Parasitemia (%) | % Inh. | Parasitemia (%) | % Inh. |
| Media Control | | 3 | | 3.8 | |
| 417 (BVp42/CFA) | | 0.4 | | 0.6 | |
| 414 (BVp42/QS21) | Preimmune | 2.2 | Neg. | 2.8 | Neg. |
| | Immune | 2.6 | | 3.1 | |
| 3005 (BVp42/ISA51) | Preimmune | 3 | Neg. | 3 | 21.4 |
| | Immune | 3.6 | | 2.4 | |
| 3006 (BVp42/QS21) | Preimmune | 2.8 | Neg. | 3.5 | 57.6 |
| | Immune | 2.8 | | 1.6 | |
| 81194 (BVp42/ISA51) | Preimmune | 3.7 | 94.3 | 2.8 | 92.3 |
| | Immune | 0.4 | | 0.4 | |
| 81591 (BVp42/QS21) | Preimmune | 3.3 | Neg. | 3 | Neg. |
| | Immune | 3.2 | | 3 | |
| 82055 (BVp42/QS21) | Preimmune | 3.8 | 16.7 | 3.4 | Neg. |
| | Immune | 3.2 | | 3.6 | |
| 82115 (BVp42/ISA51) | Preimmune | 3.3 | 29 | 3.8 | 41.7 |
| | Immune | 2.4 | | 2.3 | |

Starting Parasitemia: 0.2%

Example 15

Aotus monkeys Immunized with BVp42 Adjuvant Formulations are Protected from a Lethal Challenge of Plasmodium falciparum To generate the parasite challenge inoculum, a frozen stabilite of in vivo-passaged FUP isolate *P. falciparum* was thawed and inoculated into a malaria-naive *Aotus* monkey (Expts. 1 and 3) or into an in vitro culture of *Aotus* erythrocytes (Expt. 2). Peripheral blood containing parasitized erythrocytes was collected from infected animals or from overnight culture and adjusted to $7 \times 10^5$ parasites per ml, and 0.5 ml was injected into the saphenous vein of control animals and experimental animals at 1 week (Expt. 1), 3 weeks (Expt. 2) or 4 weeks (Expt. 3) after the final immunization. Parasitemias were monitored by Geimsa stained blood smears of peripheral blood. The experimental endpoint for these vaccination studies was defined as either parasitemia >10% erythrocytes, and erythrocyte count of $<3.0 \times 10^6$/ml, or declining health as determined by the attending veterinarian. Antimalarial therapy consisted of oral choloroquine (10 mg/kg of body weight per day for 4 days) or mefloquine (25 mg/kg of body weight, at one time). The experiment was terminated by antimalarial drug treatment of remaining, untreated animals 6 weeks after parasite challenge.

Prechallenge antibody titer values measured after the final immunization for the different adjuvant groups are presented in Table 10. High ELISA titers (>500,000) were achieved in all adjuvant groups. The highest ELISA titer (>10,000,000) was seen for an animal (81194) immunized with BVp42 in ISA51. At least one animal in each adjuvant group developed a prechallenge titer$\geq$1,000,000. Consistently higher antibody titers were noted for animals immunized with the MTP-PE+MF59 and ISA51 formulations than other adjuvant formulations. IFA titers followed a similar trend to the ELISA titers, ranging from 1:1600 in animals with the lowest ELISA titers to 1:6400 for the animal with the highest ELISA titer.

TABLE 10

Relationship of prechallenge anti-MSP1 antibody titers to characteristics of *P. falciparum* infection of Aotus immunized with BVp42 in various adjuvant formulations.

| Experiment No. | Animal No. | Immunogen | Prechallenge Antibody Titers ELISA | Prechallenge Antibody Titers IFA | Prepatent Period (days) | Pretreatment Period (days) |
|---|---|---|---|---|---|---|
| 1 | 81570 | — | — | — | 3 | 8 |
|   | 80469 |   | — | — | 4 | 12 |
|   | 80140 | BVp42/ | 1,600,000 | 1,600 | 3 | 10 |
|   | 80351 | MF59 | 700,000 | 1,600 | 5 | 10 |
| 2 | 82016 | — | — | — | 3 | 11 |
|   | 84028 |   |   |   | 7 | 13 |
|   | 84029 |   |   |   | 7 | 13 |
|   | 84017 | BVp42/ | 850,000 | 800 | 7 | 13 |
|   | 84033 | MTP-PE + | 4,000,000 | 3,200 | 7 | 13 |
|   | 84034 | MF59 | 3,000,000 | 3,200 | 7 | 13 |
|   | 84038 |   | 2,000,000 | 3,200 | 7 | 13 |
| 3 | 416 | — | — | — | 5 | 7 |
|   | 419 |   |   |   | 5 | 7 |
|   | 81262 |   |   |   | 4 | 7 |
|   | 414 | BVp42/ | 700,000 | 3,200 | 7 | 14 |
|   | 3006 | QS21 | 700,000 | 1,600 | 5 | 14 |
|   | 81591 |   | 550,000 | 3,200 | 4 | —* |
|   | 82055 |   | 1,000,000 | 3,200 | 5 | 8 |
|   | 3005 | BVp42/ | 2,900,000 | 3,200 | 8 | 20 |
|   | 81194 | ISA51 | >10,000,000 | 6,400 | 23 | —* |
|   | 82115 |   | 3,100,000 | 3,200 | 5 | 8 |

*No treatment administered during experiment; animals self-cured.

Experimental animals immunized with the various adjuvant formulations along with normal controls (expt. 1 & 3) or adjuvant controls (expt. 2) were administered a lethal, intravenous dose of *Plasmodium falciparum* (Uganda-Palo Alto isolate) after the final immunization. The course of *P. falciparum* for these animals is presented in FIGS. 11A-D.

No significant differences in the course and final outcome of infection were seen between control and experimental *Aotus* immunized with the BVp42/MF59 (FIG. 11A) or the BVp42/MTP-PE+MF59 (FIG. 11C) formulations. The time intervals between parasite injection and detection of peripheral blood parasitemia (prepatent period) and between challenge and drug-treatment (pretreatment period) were indistinguishable for control and experimental animals receiving these two formulations (Table 10).

In contrast, the course of *P. falciparum* infection was distinctly different for *Aotus* immunized with both BVp42/QS21 and BVp42/ISA51 formulations. For *Aotus* immunized with BVp42/QS21 (FIG. 11B), the prepatent period was similar to the normal controls but the course of infection and, in one instance, the outcome of infection were quite different. While parasitemias of control animals rapidly rose to treatment levels (≧10%) within seven days after parasite challenge, the course of infection in three of the four animals in the experimental group was much slower than the control group. These animals experienced a prolonged period of controlled parasite multiplication, resulting in a significantly extended pretreatment period. For one animal in this group (81591), this phase of controlled parasitemia was followed by the gradual clearance of parasites from peripheral blood and self-cure of the infection.

Figure 11A:
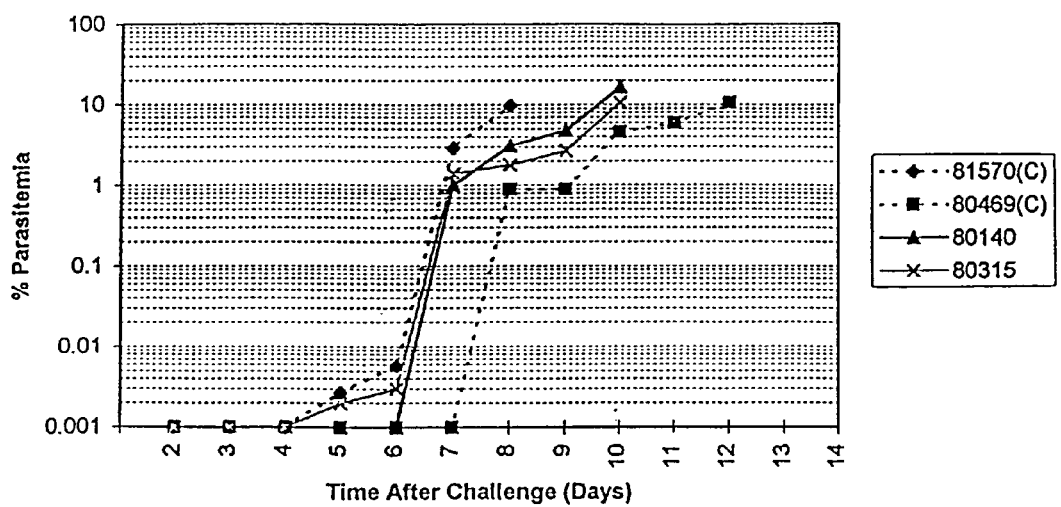
FIGS. 11A-D show the parasitemia of *Aotus* monkeys immunized with BVp42 adjuvant preparations and administered with a lethal *P. falciparum* challenge.
Figure 11B:
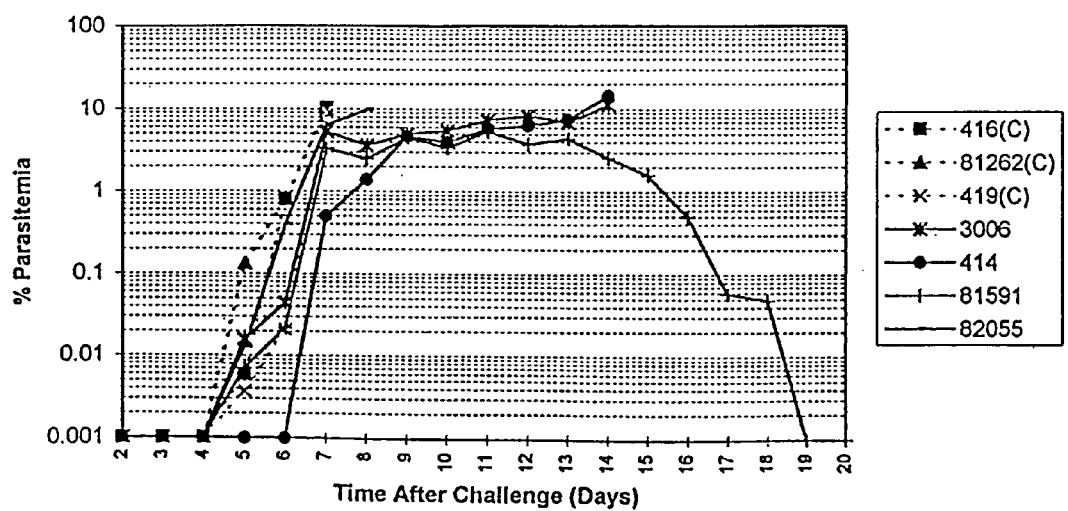
Figure 11C:
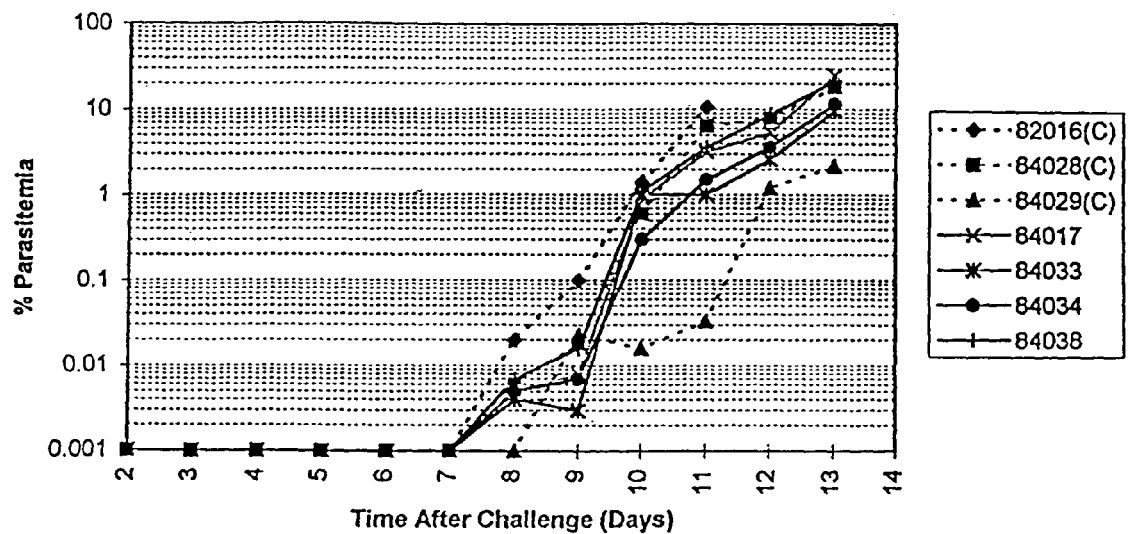
Figure 11D:
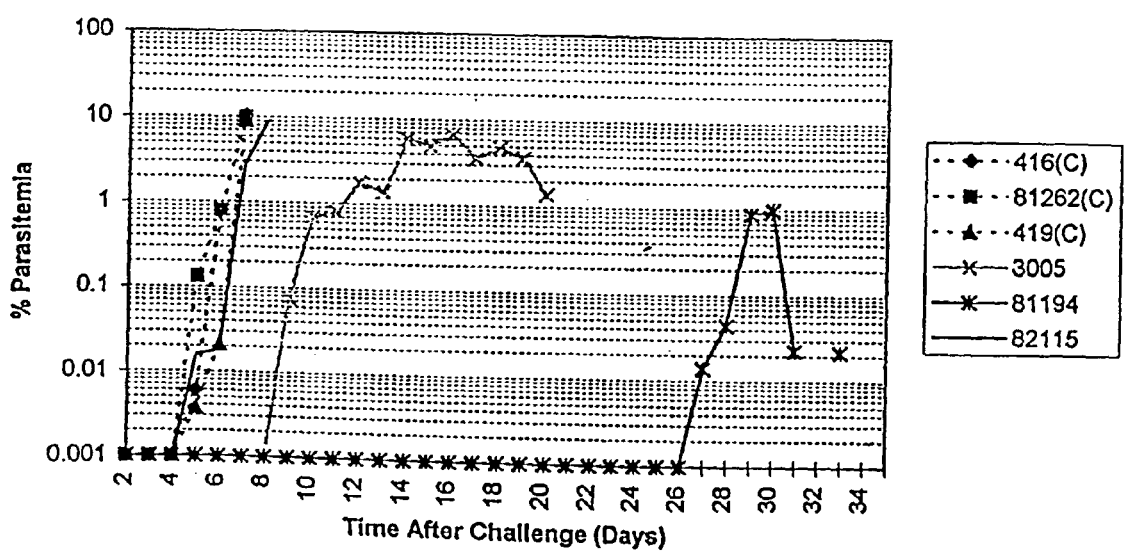

The most striking results and strongest protection were obtained with Aotus immunized with BVp42/ISA51 (FIG. 11D). The course of infection of two of the three animals in this group (3005 and 81194) was markedly different from the controls. Aotus 3005 experienced a lengthened prepatent period as compared to that of the control animals, after which time its parasitemia increased to moderate levels but was controlled for an extended period of time, similar to the QS21 group. While the trend of declining parasitemia suggested that this animal was in the process of clearing the parasite infection, it was drug-treated on day 20 because of its impaired health status. The animal displaying the highest level of protective immunity was Aotus 81194 which had no detectable parasitemia until day 23 after challenge. Thereafter, its parasitemia slowly increased, reaching a maximum of 1% on days 9-10 post-challenge. Following this peak in parasitemia, the parasite numbers abruptly dropped to low levels (<0.05%) for a week before disappearing from peripheral circulation. Most notably, Aotus 81194 remained healthy and vigorous throughout the infection period, experiencing no reduction in its erythrocyte count (data not shown).

Table 11 presents the ELISA titers of animals immunized with BVp42/QS21 and BVp42/ISA and challenged with *P. falciparum* with three different solid-phase antigens: recombinant FUP BVp42 (BVp42-M) representing the homologous MAD20 MSP1 allele, recombinant FVO BVp42 (BVp42-K) representing the heterologous K1 MSP1 allele, and parasite-derived FUP MSP 1. In the case of *Aotus* immunized with BVp42/QS21, similar titers were obtained using the homologous and heterologous BVp42 antigens and there was a high level of cross reactivity of antibodies produced against the recombinant p42 MSP1 and the homologous MSP1 purified from parasite extracts. The animal showing the highest level of immunity within this group (81591), as reflected by self-cure of the parasite infection, did not show a significant difference in specificity from others within the group. It is also interesting to note that the only animal showing no evidence of protective immunity to parasite infection in this group (82055), displayed a high ELISA titer for all three antigens. *Aotus* 81194 immunized with BVp42/ISA51 developed the highest titers against all three antigens and displayed the highest level of protective immunity. While ELISA titers were similar for another animal in the group displaying protective immunity (3005) and an unprotected animal (82115), there appeared to be a difference in specificity between these two animals. Although the reactivity of *Aotus* 3005 was similar for the homologous and heterologous BVp42 antigens (BVp42-M:BVp2-K ratio=1.3), the reactivity of *Aotus* 82115 was much lower for the heterologous than the homologous BVp42 antigen (BVp42-M:BVp42-K ratio=2.1). These results suggest that while the majority of antibodies of *Aotus* 3005 (and *Aotus* 81194) may have been directed against conserved p42 epitopes, antibodies produced by *Aotus* 82115 may not be focused to the same extent on these protective, conserved epitopes.

The results of the present study show for the first time that a MSP p42 malaria antigen formulated with the adjuvants the STIMULON™ QS21 and MONTANIDE™ ISA51 adjuvants are capable of inducing a protective immune response to *P. falciparum* infection.

TABLE 11

Comparison of ELISA titers of Aotus immunized with BVp42/QS21 and BVp42/ISA51 for homologous, recombinant BVp42-M, heterologous, recombinant BVp42-K, and homologous, parasite-purified MSP1.

| Animal No. | Immunogen | ELISA Titer | | | M:K Ratio |
| --- | --- | --- | --- | --- | --- |
| | | MSP1 | BVp42[a] | BVp42-K[b] | |
| 414 | BVp42/QS21 | 1,600,000 | 700,000 | 600,000 | 1.2 |
| 3006 | | 700,000 | 700,000 | 460,000 | 1.5 |
| 81591 | | 900,000 | 550,000 | 360,000 | 1.5 |
| 82055 | | 1,000,000 | 1,000,000 | 1,700,000 | 0.6 |
| 3005 | BVp42/ISA51 | 1,800,000 | 2,900,000 | 2,300,000 | 1.3 |
| 82115 | | 1,700,000 | 3,100,000 | 1,5000,000 | 2.1 |
| 81194 | | >10,000,000 | >10,000,000 | >10,000,000 | ~1 |

[a] BVp42 represents MSP-1 "M" allele

[b] BVp42-K represents MSP-1 "K" allele

SEQUENCE LISTING

<160> NUMBER OF SEQ ID NOS: 79

<210> SEQ ID NO 1
<211> LENGTH: 1219
<212> TYPE: DNA
<213> ORGANISM: Plasmodium falciparum

<400> SEQUENCE: 1

```
ggatccactg ggatgtggag ctggaagtgc ctcctcttct gggctgtcct ggtcacagcc      60
acactctgca ccgcggcgat atctgtcaca atggataata tcctctcagg atttgaaaat     120
gaatatgatg ttatatattt aaaaccttta gctggagtat atagaagctt aaaaaaacaa     180
attgaaaaaa acattttac atttaattta aatttgaacg atatcttaaa ttcacgtctt     240
aagaaacgaa atatttctt agatgtatta gaatctgatt taatgcaatt taaacatata     300
tcctcaaatg aatacattat tgaagattca tttaaattat tgaattcaga acaaaaaaac     360
acacttttaa aaagttacaa atatataaaa gaatcagtag aaaatgatat taaatttgca     420
caggaaggta taagttatta tgaaaaggtt ttagcgaaat ataaggatga tttagaatca     480
attaaaaaag ttatcaaaga agaaaaggag aagttcccat catcaccacc aacaacacct     540
ccgtcaccag caaaaacaga cgaacaaaag aaggaaagta agttccttcc atttttaaca     600
aacattgaga ccttatacaa taacttagtt aataaaattg acgattactt aattaactta     660
aaggcaaaga ttaacgattg taatgttgaa aaagatgaag cacatgttaa ataactaaa     720
cttagtgatt taaaagcaat tgatgacaaa atagatcttt ttaaaaacca taacgacttc     780
gaagcaatta aaaaattgat aaatgatgat acgaaaaaag atatgcttgg caaattactt     840
agtacaggat tagttcaaaa ttttcctaat acaataatat caaaattaat tgaaggaaaa     900
ttccaagata tgttaaacat ttcacaacac caatgcgtaa aaaacaatg tccagaaaat     960
tctggatgtt tcagacattt agatgaaaga gaagaatgta aatgtttatt aaattacaaa    1020
caagaaggtg ataaatgtgt tgaaaatcca atcctacttt gtaacgaaaa taatggtgga    1080
tgtgatgcag atgccaaatg taccgaagaa gattcaggta gcaacggaaa gaaaatcaca    1140
tgtgaatgta ctaaacctga ttcttatcca cttttcgatg gtattttctg cagttagtag    1200
tcgacccttg gaaggatcc                                                 1219
```

<210> SEQ ID NO 2
<211> LENGTH: 394
<212> TYPE: PRT
<213> ORGANISM: plasmodium falciparum

<400> SEQUENCE: 2

```
Ala Ile Ser Val Thr Met Asp Asn Ile Leu Ser Gly Phe Glu Asn Glu
1               5                   10                  15

Tyr Asp Val Ile Tyr Leu Lys Pro Leu Ala Gly Val Tyr Arg Ser Leu
            20                  25                  30

Lys Lys Gln Ile Glu Lys Asn Ile Phe Thr Phe Asn Leu Asn Leu Asn
        35                  40                  45

Asp Ile Leu Asn Ser Arg Leu Lys Lys Arg Lys Tyr Phe Leu Asp Val
    50                  55                  60

Leu Glu Ser Asp Leu Met Gln Phe Lys His Ile Ser Ser Asn Glu Tyr
65                  70                  75                  80

Ile Ile Glu Asp Ser Phe Lys Leu Leu Asn Ser Glu Gln Lys Asn Thr
                85                  90                  95
```

Leu Leu Lys Ser Tyr Lys Tyr Ile Lys Glu Ser Val Glu Asn Asp Ile
            100                 105                 110

Lys Phe Ala Gln Glu Gly Ile Ser Tyr Tyr Glu Lys Val Leu Ala Lys
        115                 120                 125

Tyr Lys Asp Asp Leu Glu Ser Ile Lys Lys Val Ile Lys Glu Glu Lys
    130                 135                 140

Glu Lys Phe Pro Ser Ser Pro Thr Pro Pro Ser Pro Ala Lys
145                 150                 155                 160

Thr Asp Glu Gln Lys Lys Glu Ser Lys Phe Leu Pro Phe Leu Thr Asn
                165                 170                 175

Ile Glu Thr Leu Tyr Asn Asn Leu Val Asn Lys Ile Asp Asp Tyr Leu
            180                 185                 190

Ile Asn Leu Lys Ala Lys Ile Asn Asp Cys Asn Val Glu Lys Asp Glu
        195                 200                 205

Ala His Val Lys Ile Thr Lys Leu Ser Asp Leu Lys Ala Ile Asp Asp
    210                 215                 220

Lys Ile Asp Leu Phe Lys Asn His Asn Asp Phe Glu Ala Ile Lys Lys
225                 230                 235                 240

Leu Ile Asn Asp Asp Thr Lys Lys Asp Met Leu Gly Lys Leu Leu Ser
                245                 250                 255

Thr Gly Leu Val Gln Asn Phe Pro Asn Thr Ile Ile Ser Lys Leu Ile
            260                 265                 270

Glu Gly Lys Phe Gln Asp Met Leu Asn Ile Ser Gln His Gln Cys Val
        275                 280                 285

Lys Lys Gln Cys Pro Glu Asn Ser Gly Cys Phe Arg His Leu Asp Glu
    290                 295                 300

Arg Glu Glu Cys Lys Cys Leu Leu Asn Tyr Lys Gln Glu Gly Asp Lys
305                 310                 315                 320

Cys Val Glu Asn Pro Asn Pro Thr Cys Asn Glu Asn Asn Gly Gly Cys
                325                 330                 335

Asp Ala Asp Ala Lys Cys Thr Glu Glu Asp Ser Gly Ser Asn Gly Lys
            340                 345                 350

Lys Ile Thr Cys Glu Cys Thr Lys Pro Asp Ser Tyr Pro Leu Phe Asp
        355                 360                 365

Gly Ile Phe Cys Ser Ser Ser Asn Phe Leu Gly Ile Ser Phe Leu Leu
    370                 375                 380

Ile Leu Met Leu Ile Leu Tyr Ser Phe Ile
385                 390

<210> SEQ ID NO 3
<211> LENGTH: 394
<212> TYPE: PRT
<213> ORGANISM: plasmodium falciparum

<400> SEQUENCE: 3

Ala Ile Ser Val Thr Met Asp Asn Ile Leu Ser Gly Phe Glu Asn Glu
1               5                   10                  15

Tyr Asp Val Ile Tyr Leu Lys Pro Leu Ala Gly Val Tyr Arg Ser Leu
            20                  25                  30

Lys Lys Gln Ile Glu Lys Asn Ile Ile Thr Phe Asn Leu Asn Leu Asn
        35                  40                  45

Asp Ile Leu Asn Ser Arg Leu Lys Lys Arg Lys Tyr Phe Leu Asp Val
    50                  55                  60

Leu Glu Ser Asp Leu Met Gln Phe Lys His Ile Ser Ser Asn Glu Tyr

```
                65                  70                  75                  80

Ile Ile Glu Asp Ser Phe Lys Leu Leu Asn Ser Glu Gln Lys Asn Ile
                85                  90                  95

Leu Leu Lys Ser Tyr Lys Tyr Ile Lys Glu Ser Val Glu Asn Asp Ile
            100                 105                 110

Lys Phe Ala Gln Glu Gly Ile Ser Tyr Tyr Glu Lys Val Leu Ala Lys
            115                 120                 125

Tyr Lys Asp Asp Leu Glu Ser Ile Lys Lys Val Ile Lys Glu Lys
        130                 135                 140

Glu Lys Phe Pro Ser Ser Pro Thr Thr Pro Pro Ser Pro Ala Lys
145                 150                 155                 160

Thr Asp Glu Gln Lys Lys Glu Ser Lys Phe Leu Pro Phe Leu Thr Asn
                165                 170                 175

Ile Glu Thr Leu Tyr Asn Asn Leu Val Asn Lys Ile Asp Asp Tyr Leu
            180                 185                 190

Ile Asn Leu Lys Ala Lys Ile Asn Asp Cys Asn Val Glu Lys Asp Glu
            195                 200                 205

Ala His Val Lys Ile Thr Lys Leu Ser Asp Leu Lys Ala Ile Asp Asp
        210                 215                 220

Lys Ile Asp Leu Phe Lys Asn Thr Asn Asp Phe Glu Ala Ile Lys Lys
225                 230                 235                 240

Leu Ile Asn Asp Asp Thr Lys Lys Asp Met Leu Gly Lys Leu Leu Ser
                245                 250                 255

Thr Gly Leu Val Gln Ile Phe Pro Asn Thr Ile Ile Ser Lys Leu Ile
            260                 265                 270

Glu Gly Lys Phe Gln Asp Met Leu Asn Ile Ser Gln His Gln Cys Val
            275                 280                 285

Lys Lys Gln Cys Pro Glu Asn Ser Gly Cys Phe Arg His Leu Asp Glu
290                 295                 300

Arg Glu Glu Cys Lys Cys Leu Leu Asn Tyr Lys Gln Glu Gly Asp Lys
305                 310                 315                 320

Cys Glu Glu Asn Pro Asn Pro Thr Cys Asn Glu Asn Asn Gly Gly Cys
                325                 330                 335

Asp Ala Asp Ala Thr Cys Thr Glu Glu Asp Ser Gly Ser Ser Arg Lys
            340                 345                 350

Lys Ile Thr Cys Glu Cys Thr Lys Pro Asp Ser Tyr Pro Leu Phe Asp
        355                 360                 365

Gly Ile Phe Cys Ser Ser Ser Asn Phe Leu Gly Ile Ser Phe Leu Leu
        370                 375                 380

Ile Leu Met Leu Ile Leu Tyr Ser Phe Ile
385                 390

<210> SEQ ID NO 4
<211> LENGTH: 375
<212> TYPE: PRT
<213> ORGANISM: plasmodium falciparum

<400> SEQUENCE: 4

Ala Val Thr Pro Ser Val Ile His Asn Ile Leu Ser Lys Ile Glu Asn
1               5                   10                  15

Glu Tyr Glu Val Leu Tyr Leu Lys Pro Leu Ala Gly Val Tyr Arg Ser
            20                  25                  30

Leu Lys Lys Gln Leu Glu Asn Asn Val Met Thr Phe Asn Val Asn Val
        35                  40                  45
```

```
Lys Asp Ile Leu Asn Ser Pro Phe Asn Lys Arg Glu Asn Phe Lys Asn
 50                  55                  60

Val Leu Glu Ser Asp Leu Ile Pro Tyr Lys Asp Leu Thr Ser Ser Asn
 65                  70                  75                  80

Tyr Val Val Lys Asp Pro Tyr Lys Phe Leu Asn Lys Glu Lys Arg Asp
                 85                  90                  95

Lys Phe Leu Ser Ser Tyr Asn Tyr Ile Lys Asp Ser Ile Asp Thr Asp
                100                 105                 110

Ile Asn Phe Ala Asn Asp Val Leu Gly Tyr Tyr Lys Ile Leu Ser Glu
            115                 120                 125

Lys Tyr Lys Ser Asp Leu Asp Ser Ile Lys Lys Tyr Ile Asn Asp Lys
        130                 135                 140

Gln Gly Glu Asn Glu Lys Tyr Leu Pro Phe Leu Asn Asn Ile Glu Thr
145                 150                 155                 160

Leu Tyr Lys Thr Val Asn Asp Lys Ile Asp Leu Phe Val Ile His Leu
                165                 170                 175

Glu Ala Lys Val Leu Asn Tyr Thr Tyr Glu Lys Ser Asn Val Glu Ile
                180                 185                 190

Lys Glu Leu Ile Tyr Leu Lys Thr Ile Gln Asp Lys Leu Ala Asp Phe
            195                 200                 205

Lys Lys Asn Asn Asn Phe Val Gly Ile Ala Asp Leu Ser Thr Asp Tyr
        210                 215                 220

Asn His Asn Asn Leu Leu Thr Lys Phe Leu Ser Thr Gly Met Val Phe
225                 230                 235                 240

Glu Asn Leu Leu Lys Ser Ile Leu Ser Asn Leu Leu Asp Trp Lys Leu
                245                 250                 255

Ala Arg Tyr Val Lys His Phe Thr Thr Pro Met Arg Lys Lys Thr Met
                260                 265                 270

Ile Gln Gln Asn Ser Gly Cys Phe Arg His Leu Asp Glu Arg Glu Glu
            275                 280                 285

Cys Lys Cys Leu Leu Asn Tyr Lys Gln Glu Gly Ser Lys Cys Val Glu
        290                 295                 300

Asn Pro Asn Pro Thr Cys Asn Glu Asn Gly Gly Cys Asp Ala Asp
305                 310                 315                 320

Ala Lys Cys Thr Glu Glu Asp Ser Gly Ser Asn Gly Lys Lys Ile Thr
                325                 330                 335

Cys Gln Cys Thr Lys Pro Asp Ser Tyr Pro Leu Ser Met Val Ile Phe
            340                 345                 350

Cys Ser Ser Ser Asn Phe Leu Gly Ile Ser Phe Leu Leu Ile Leu Met
        355                 360                 365

Leu Ile Leu Tyr Ser Phe Ile
        370                 375

<210> SEQ ID NO 5
<211> LENGTH: 377
<212> TYPE: PRT
<213> ORGANISM: plasmodium falciparum

<400> SEQUENCE: 5

Ala Val Thr Thr Ser Val Ile Asp Asn Ile Leu Ser Lys Ile Glu Asn
1               5                  10                  15

Glu Tyr Glu Val Leu Tyr Leu Lys Pro Leu Ala Gly Val Tyr Arg Ser
                20                  25                  30

Leu Lys Lys Gln Leu Glu Asn Asn Val Met Thr Phe Asn Val Asn Val
            35                  40                  45
```

| | | | | | | | | | | | |
|---|---|---|---|---|---|---|---|---|---|---|---|
| Lys | Asp | Ile | Leu | Asn | Ser | Arg | Phe | Asn | Lys | Arg | Glu | Asn | Phe | Lys | Asn |
| | | | 50 | | | | | 55 | | | | | 60 | | |
| Val | Leu | Glu | Ser | Asp | Leu | Ile | Pro | Tyr | Lys | Asp | Leu | Thr | Ser | Ser | Asn |
| 65 | | | | | 70 | | | | | 75 | | | | | 80 |
| Tyr | Val | Val | Lys | Asp | Pro | Tyr | Lys | Phe | Leu | Asn | Lys | Glu | Lys | Arg | Asp |
| | | | | 85 | | | | | 90 | | | | | 95 | |
| Lys | Phe | Leu | Ser | Ser | Tyr | Asn | Tyr | Ile | Lys | Asp | Ser | Ile | Asp | Thr | Asp |
| | | | 100 | | | | | 105 | | | | | 110 | | |
| Ile | Asn | Phe | Ala | Asn | Asp | Val | Leu | Gly | Tyr | Tyr | Lys | Ile | Leu | Ser | Glu |
| | | | 115 | | | | | 120 | | | | | 125 | | |
| Lys | Tyr | Lys | Ser | Asp | Leu | Asp | Ser | Ile | Lys | Lys | Tyr | Ile | Asn | Asp | Lys |
| | | | 130 | | | | | 135 | | | | | 140 | | |
| Gln | Gly | Glu | Asn | Glu | Lys | Tyr | Leu | Pro | Phe | Leu | Asn | Asn | Ile | Glu | Thr |
| 145 | | | | | 150 | | | | | 155 | | | | | 160 |
| Leu | Tyr | Lys | Thr | Val | Asn | Asp | Lys | Ile | Asp | Leu | Phe | Val | Ile | His | Leu |
| | | | | 165 | | | | | 170 | | | | | 175 | |
| Glu | Ala | Lys | Val | Leu | Asn | Tyr | Thr | Tyr | Glu | Lys | Ser | Asn | Val | Glu | Val |
| | | | | 180 | | | | | 185 | | | | | 190 | |
| Lys | Ile | Lys | Glu | Leu | Asn | Tyr | Leu | Lys | Thr | Ile | Gln | Asp | Lys | Leu | Ala |
| | | | 195 | | | | | 200 | | | | | 205 | | |
| Asp | Phe | Lys | Lys | Asn | Asn | Asn | Phe | Val | Gly | Ile | Ala | Asp | Leu | Ser | Thr |
| | 210 | | | | | 215 | | | | | 220 | | | | |
| Asp | Tyr | Asn | His | Asn | Asn | Leu | Leu | Thr | Lys | Phe | Leu | Ser | Thr | Gly | Met |
| 225 | | | | | 230 | | | | | 235 | | | | | 240 |
| Val | Phe | Glu | Asn | Leu | Leu | Lys | Ser | Val | Leu | Ser | Asn | Leu | Leu | Asp | Trp |
| | | | | 245 | | | | | 250 | | | | | 255 | |
| Lys | Leu | Ala | Arg | Tyr | Val | Lys | His | Phe | Thr | Thr | Pro | Met | Arg | Lys | Lys |
| | | | 260 | | | | | 265 | | | | | 270 | | |
| Thr | Met | Ile | Gln | Gln | Ser | Ser | Gly | Cys | Phe | Arg | His | Leu | Asp | Glu | Arg |
| | 275 | | | | | 280 | | | | | 285 | | | | |
| Glu | Glu | Cys | Lys | Cys | Leu | Leu | Asn | Tyr | Lys | Gln | Glu | Gly | Asp | Lys | Cys |
| | 290 | | | | | 295 | | | | | 300 | | | | |
| Val | Glu | Asn | Pro | Asn | Pro | Thr | Cys | Asn | Glu | Asn | Asn | Gly | Gly | Cys | Asp |
| 305 | | | | | 310 | | | | | 315 | | | | | 320 |
| Ala | Asp | Ala | Lys | Cys | Thr | Glu | Glu | Asp | Ser | Gly | Ser | Asn | Gly | Lys | Lys |
| | | | | 325 | | | | | 330 | | | | | 335 | |
| Ile | Thr | Cys | Glu | Cys | Thr | Lys | Pro | Asp | Cys | Tyr | Pro | Leu | Phe | Asp | Gly |
| | | | 340 | | | | | 345 | | | | | 350 | | |
| Ile | Phe | Cys | Ser | Ser | Ser | Asn | Phe | Leu | Gly | Ile | Ser | Phe | Leu | Leu | Ile |
| | | | 355 | | | | | 360 | | | | | 365 | | |
| Leu | Met | Leu | Ile | Leu | Tyr | Ser | Phe | Ile | | | | | | | |
| | 370 | | | | | 375 | | | | | | | | | |

<210> SEQ ID NO 6
<211> LENGTH: 1235
<212> TYPE: DNA
<213> ORGANISM: Artificial sequence
<220> FEATURE:
<223> OTHER INFORMATION: synthetic

<400> SEQUENCE: 6

| | |
|---|---|
| attggatcca ctaaaatgtg gtcttggaag tgtcttttat tctgggctgt cttggtgacc | 60 |
| gccactcttt gcacagcagc gatctctgtt actatggaca acatcctcag tggcttcgag | 120 |
| aacgagtacg acgtaatcta cctaaagccc cttgccggtg tctaccgttc attgaagaaa | 180 |

-continued

```
cagatagaaa agaatatttt cacgttcaac ctcaacctaa atgacatcct caactcgcgc      240
ctcaagaagc gaaatactt cctcgacgtg ttggaatccg accttatgca atttaagcac       300
attagctcta acgagtacat catagaggac agcttcaagc tcttgaattc agaacagaag      360
aacaccctcc taaagtccta caaatacatt aaggagtctg ttgagaacga catcaagttc      420
gcccaggaag gaattagcta ctatgagaaa gtcctggcta atacaagga cgacttggaa       480 agcattaaga aggtaatcaa agaagagaag gaaaagtttc cgagctctcc acccacaact      540
cccccatcgc ctgcaaagac cgacgagcag aaaaaagaaa gtaagttcct tccattcctc      600
accaacatcg aaactctata taacaacctg gtgaacaaga ttgatgacta cttaatcaac      660
ttgaaggcga aaattaatga ctgtaacgtc gaaaaggatg aagcccacgt taagatcacc      720
aagctttccg atctcaaagc catcgacgat aagattgacc tgtttaagaa ccacaacgat      780
ttcgacgcaa tcaaaaagtt gatcaacgac gatactaaga aagacatgct tggaaaactg      840
ctgtcgacag gcttggtcca aaacttcccg aacaccatta aagcaagct gatcgaagga      900 aagtttcagg atatgctgaa catctctcag catcaatgcg tgaagaagca atgtcccgag      960
aattcaggtt gcttccgcca cttagacgaa agggaggaat gtaaatgcct gctgaattat      1020
aaacaggaag agacaagtg cgtagagaat cctaacccaa cctgtaacga aaataacggt      1080
ggctgcgatg ctgacgctaa gtgtaccgag gaggacagcg gttccaatgg caagaaaata      1140
acttgcgaat gcacgaagcc cgatagttac cctctcttcg acggtatctt ctgctcccca      1200
cctcatcatc atcatcatca ttaataaggt accta                                1235
```

<210> SEQ ID NO 7
<211> LENGTH: 1175
<212> TYPE: DNA
<213> ORGANISM: Plasmodium falciparum
<220> FEATURE:
<221> NAME/KEY: CDS
<222> LOCATION: (12)..(1163)
<223> OTHER INFORMATION:

<400> SEQUENCE: 7

```
ggatccctaa a atg tgg agc tgg aag tgc ctc ctc ttc tgg gct gtc ctg      50
            Met Trp Ser Trp Lys Cys Leu Leu Phe Trp Ala Val Leu
            1               5                   10 gtc aca gcc aca ctc tgc acc gcg ggc gcc gca gta act cct tcc gta       98
Val Thr Ala Thr Leu Cys Thr Ala Gly Ala Ala Val Thr Pro Ser Val
 15                  20                  25 att gat aac ata ctt tct aaa att gaa aat gaa tat gag gtt tta tat      146
Ile Asp Asn Ile Leu Ser Lys Ile Glu Asn Glu Tyr Glu Val Leu Tyr
 30              35                  40                  45 tta aaa cct tta gca ggt gtt tat aga agt tta aaa aaa caa tta gaa      194
Leu Lys Pro Leu Ala Gly Val Tyr Arg Ser Leu Lys Lys Gln Leu Glu
                 50                  55                  60 aat aac gtt atg aca ttt aat gtt aat gtt aag gat att tta aat tca      242
Asn Asn Val Met Thr Phe Asn Val Asn Val Lys Asp Ile Leu Asn Ser
             65                  70                  75 cga ttt aat aaa cgt gaa aat ttc aaa aat gtt tta gaa tca gat tta      290
Arg Phe Asn Lys Arg Glu Asn Phe Lys Asn Val Leu Glu Ser Asp Leu
         80                  85                  90 att cca tat aaa gat tta aca tca agt aat tat gtt gtc aaa gat cca      338
Ile Pro Tyr Lys Asp Leu Thr Ser Ser Asn Tyr Val Val Lys Asp Pro
     95                 100                 105 tat aaa ttt ctt aat aaa gaa aaa aga gat aaa ttc tta agc agt tat      386
Tyr Lys Phe Leu Asn Lys Glu Lys Arg Asp Lys Phe Leu Ser Ser Tyr
```

```
                110                 115                 120                 125
aat tat att aag gat tca ata gat acg gat ata aat ttt gca aat gat         434
Asn Tyr Ile Lys Asp Ser Ile Asp Thr Asp Ile Asn Phe Ala Asn Asp
                130                 135                 140 gtt ctt gga tat tat aaa ata tta tcc gaa aaa tat aaa tca gat tta         482
Val Leu Gly Tyr Tyr Lys Ile Leu Ser Glu Lys Tyr Lys Ser Asp Leu
            145                 150                 155 gat tca att aaa aaa tat atc aac gac aaa caa ggt gaa aat gag aaa         530
Asp Ser Ile Lys Lys Tyr Ile Asn Asp Lys Gln Gly Glu Asn Glu Lys
        160                 165                 170 tac ctt ccc ttt tta aac aat att gag acc tta tat aaa aca gtt aat         578
Tyr Leu Pro Phe Leu Asn Asn Ile Glu Thr Leu Tyr Lys Thr Val Asn
    175                 180                 185 cat aaa att gat tta ttt gta att cat tta gaa gca aaa gtt cta aat         626
His Lys Ile Asp Leu Phe Val Ile His Leu Glu Ala Lys Val Leu Asn
190                 195                 200                 205 tat aca tat gag aaa tca aac gta gaa gtt aaa ata aaa gaa ctt aat         674
Tyr Thr Tyr Glu Lys Ser Asn Val Glu Val Lys Ile Lys Glu Leu Asn
                210                 215                 220 tac tta aaa aca att caa gac aaa ttg gca gat ttt aaa aaa aat aac         722
Tyr Leu Lys Thr Ile Gln Asp Lys Leu Ala Asp Phe Lys Lys Asn Asn
            225                 230                 235 aat ttc gtt gga att gct gat tta tca aca gat tat aac cat aat aac         770
Asn Phe Val Gly Ile Ala Asp Leu Ser Thr Asp Tyr Asn His Asn Asn
        240                 245                 250 tta ttg aca aag ttc ctt agt aca ggt atg gtt ttt gaa aat ctt gct         818
Leu Leu Thr Lys Phe Leu Ser Thr Gly Met Val Phe Glu Asn Leu Ala
    255                 260                 265 aaa acc gtt tta tct aat tta ctt gat gga aac ttg caa ggt atg tta         866
Lys Thr Val Leu Ser Asn Leu Leu Asp Gly Asn Leu Gln Gly Met Leu
270                 275                 280                 285 aac att tca caa cac caa tgc gta aaa aaa caa tgt cca caa aat tct         914
Asn Ile Ser Gln His Gln Cys Val Lys Lys Gln Cys Pro Gln Asn Ser
                290                 295                 300 gga tgt ttc aga cat tta gat gaa aga gaa gaa tgt aaa tgt tta tta         962
Gly Cys Phe Arg His Leu Asp Glu Arg Glu Glu Cys Lys Cys Leu Leu
            305                 310                 315 aat tac aaa caa gaa ggt gat aaa tgt gtt gaa aat cca aat cct act        1010
Asn Tyr Lys Gln Glu Gly Asp Lys Cys Val Glu Asn Pro Asn Pro Thr
        320                 325                 330 tgt aac gaa aat aat ggt gga tgt gat gca gat gcc aaa tgt acc gaa        1058
Cys Asn Glu Asn Asn Gly Gly Cys Asp Ala Asp Ala Lys Cys Thr Glu
    335                 340                 345 gaa gat tca ggt agc aac gga aag aaa atc aca tgt gaa tgt act aaa        1106
Glu Asp Ser Gly Ser Asn Gly Lys Lys Ile Thr Cys Glu Cys Thr Lys
350                 355                 360                 365 cct gat tct tat cca ctt ttc gat ggt att ttc tgc agt cat cat cat        1154
Pro Asp Ser Tyr Pro Leu Phe Asp Gly Ile Phe Cys Ser His His His
                370                 375                 380 cat cat cat taataaggta cc                                               1175
His His His <210> SEQ ID NO 8
<211> LENGTH: 384
<212> TYPE: PRT
<213> ORGANISM: Plasmodium falciparum

<400> SEQUENCE: 8

Met Trp Ser Trp Lys Cys Leu Leu Phe Trp Ala Val Leu Val Thr Ala
1               5                   10                  15
```

```
Thr Leu Cys Thr Ala Gly Ala Ala Val Thr Pro Ser Val Ile Asp Asn
         20                  25                  30

Ile Leu Ser Lys Ile Glu Asn Glu Tyr Glu Val Leu Tyr Leu Lys Pro
         35                  40                  45

Leu Ala Gly Val Tyr Arg Ser Leu Lys Lys Gln Leu Glu Asn Asn Val
     50                  55                  60

Met Thr Phe Asn Val Asn Val Lys Asp Ile Leu Asn Ser Arg Phe Asn
 65                  70                  75                  80

Lys Arg Glu Asn Phe Lys Asn Val Leu Glu Ser Asp Leu Ile Pro Tyr
                 85                  90                  95

Lys Asp Leu Thr Ser Ser Asn Tyr Val Val Lys Asp Pro Tyr Lys Phe
            100                 105                 110

Leu Asn Lys Glu Lys Arg Asp Lys Phe Leu Ser Ser Tyr Asn Tyr Ile
            115                 120                 125

Lys Asp Ser Ile Asp Thr Asp Ile Asn Phe Ala Asn Asp Val Leu Gly
130                 135                 140

Tyr Tyr Lys Ile Leu Ser Glu Lys Tyr Lys Ser Asp Leu Asp Ser Ile
145                 150                 155                 160

Lys Lys Tyr Ile Asn Asp Lys Gln Gly Glu Asn Glu Lys Tyr Leu Pro
                165                 170                 175

Phe Leu Asn Asn Ile Glu Thr Leu Tyr Lys Thr Val Asn His Lys Ile
            180                 185                 190

Asp Leu Phe Val Ile His Leu Glu Ala Lys Val Leu Asn Tyr Thr Tyr
        195                 200                 205

Glu Lys Ser Asn Val Glu Val Lys Ile Lys Glu Leu Asn Tyr Leu Lys
    210                 215                 220

Thr Ile Gln Asp Lys Leu Ala Asp Phe Lys Lys Asn Asn Asn Phe Val
225                 230                 235                 240

Gly Ile Ala Asp Leu Ser Thr Asp Tyr Asn His Asn Asn Leu Leu Thr
                245                 250                 255

Lys Phe Leu Ser Thr Gly Met Val Phe Glu Asn Leu Ala Lys Thr Val
            260                 265                 270

Leu Ser Asn Leu Leu Asp Gly Asn Leu Gln Gly Met Leu Asn Ile Ser
        275                 280                 285

Gln His Gln Cys Val Lys Lys Gln Cys Pro Gln Asn Ser Gly Cys Phe
    290                 295                 300

Arg His Leu Asp Glu Arg Glu Glu Cys Lys Cys Leu Leu Asn Tyr Lys
305                 310                 315                 320

Gln Glu Gly Asp Lys Cys Val Glu Asn Pro Asn Pro Thr Cys Asn Glu
                325                 330                 335

Asn Asn Gly Gly Cys Asp Ala Asp Ala Lys Cys Thr Glu Glu Asp Ser
            340                 345                 350

Gly Ser Asn Gly Lys Lys Ile Thr Cys Glu Cys Thr Lys Pro Asp Ser
        355                 360                 365

Tyr Pro Leu Phe Asp Gly Ile Phe Cys Ser His His His His His
    370                 375                 380

<210> SEQ ID NO 9
<211> LENGTH: 10
<212> TYPE: PRT
<213> ORGANISM: Artificial sequence
<220> FEATURE:
<223> OTHER INFORMATION: synthetic

<400> SEQUENCE: 9
```

Ile Ser Val Thr Met Asp Asn Ile Leu Ser
1               5                   10

<210> SEQ ID NO 10
<211> LENGTH: 30
<212> TYPE: DNA
<213> ORGANISM: Artificial sequence
<220> FEATURE:
<223> OTHER INFORMATION: synthetic

<400> SEQUENCE: 10
attggatcca ctaaaatgtg gagctggaag                              30

<210> SEQ ID NO 11
<211> LENGTH: 30
<212> TYPE: DNA
<213> ORGANISM: Artificial sequence
<220> FEATURE:
<223> OTHER INFORMATION: synthetic

<400> SEQUENCE: 11
tatggcgccc gcggtgcaga gtgtggctgt                              30

<210> SEQ ID NO 12
<211> LENGTH: 30
<212> TYPE: DNA
<213> ORGANISM: Artificial sequence
<220> FEATURE:
<223> OTHER INFORMATION: synthetic

<400> SEQUENCE: 12
ttaggcgccg cagtaactcc ttccgtaatt                              30

<210> SEQ ID NO 13
<211> LENGTH: 27
<212> TYPE: DNA
<213> ORGANISM: Artificial sequence
<220> FEATURE:
<223> OTHER INFORMATION: synthetic

<400> SEQUENCE: 13
taactgcaga aaataccatc gaaaagt                                 27

<210> SEQ ID NO 14
<211> LENGTH: 43
<212> TYPE: DNA
<213> ORGANISM: Artificial sequence
<220> FEATURE:
<223> OTHER INFORMATION: synthetic

<400> SEQUENCE: 14
taactgcagt catcatcatc atcatcatta ataaggtacc gag               43

<210> SEQ ID NO 15
<211> LENGTH: 43
<212> TYPE: DNA
<213> ORGANISM: Artificial sequence
<220> FEATURE:
<223> OTHER INFORMATION: synthetic

<400> SEQUENCE: 15
ataggtacct tattaatgat gatgatgatg atgactgcag tta               43

<210> SEQ ID NO 16
<211> LENGTH: 402

<212> TYPE: PRT
<213> ORGANISM: Artificial sequence
<220> FEATURE:
<223> OTHER INFORMATION: synthetic

<400> SEQUENCE: 16

```
Met Trp Ser Trp Lys Cys Leu Leu Phe Trp Ala Val Leu Val Thr Ala
1               5                   10                  15

Thr Leu Cys Thr Ala Ala Ile Ser Val Thr Met Asp Asn Ile Leu Ser
            20                  25                  30

Gly Phe Glu Asn Glu Tyr Asp Val Ile Tyr Leu Lys Pro Leu Ala Gly
        35                  40                  45

Val Tyr Arg Ser Leu Lys Lys Gln Ile Glu Lys Asn Ile Phe Thr Phe
    50                  55                  60

Asn Leu Asn Leu Asn Asp Ile Leu Asn Ser Arg Leu Lys Lys Arg Lys
65                  70                  75                  80

Tyr Phe Leu Asp Val Leu Glu Ser Asp Leu Met Gln Phe Lys His Ile
                85                  90                  95

Ser Ser Asn Glu Tyr Ile Ile Glu Asp Ser Phe Lys Leu Leu Asn Ser
            100                 105                 110

Glu Gln Lys Asn Thr Leu Leu Lys Ser Tyr Lys Tyr Ile Lys Glu Ser
        115                 120                 125

Val Glu Asn Asp Ile Lys Phe Ala Gln Glu Gly Ile Ser Tyr Tyr Glu
    130                 135                 140

Lys Val Leu Ala Lys Tyr Lys Asp Asp Leu Glu Ser Ile Lys Lys Val
145                 150                 155                 160

Ile Lys Glu Glu Lys Glu Lys Phe Pro Ser Ser Pro Thr Thr Pro
                165                 170                 175

Pro Ser Pro Ala Lys Thr Asp Glu Gln Lys Lys Glu Ser Lys Phe Leu
            180                 185                 190

Pro Phe Leu Thr Asn Ile Glu Thr Leu Tyr Asn Asn Leu Val Asn Lys
        195                 200                 205

Ile Asp Asp Tyr Leu Ile Asn Leu Lys Ala Lys Ile Asn Asp Cys Asn
    210                 215                 220

Val Glu Lys Asp Glu Ala His Val Lys Ile Thr Lys Leu Ser Asp Leu
225                 230                 235                 240

Lys Ala Ile Asp Asp Lys Ile Asp Leu Phe Lys Asn His Asn Asp Phe
                245                 250                 255

Asp Ala Ile Lys Lys Leu Ile Asn Asp Asp Thr Lys Lys Asp Met Leu
            260                 265                 270

Gly Lys Leu Leu Ser Thr Gly Leu Val Gln Asn Phe Pro Asn Thr Ile
        275                 280                 285

Ile Ser Lys Leu Ile Glu Gly Lys Phe Gln Asp Met Leu Asn Ile Ser
    290                 295                 300

Gln His Gln Cys Val Lys Lys Gln Cys Pro Glu Asn Ser Gly Cys Phe
305                 310                 315                 320

Arg His Leu Asp Glu Arg Glu Glu Cys Lys Cys Leu Leu Asn Tyr Lys
                325                 330                 335

Gln Glu Gly Asp Lys Cys Val Glu Asn Pro Asn Pro Thr Cys Asn Glu
            340                 345                 350

Asn Asn Gly Gly Cys Asp Ala Asp Ala Lys Cys Thr Glu Glu Asp Ser
        355                 360                 365

Gly Ser Asn Gly Lys Lys Ile Thr Cys Glu Cys Thr Lys Pro Asp Ser
    370                 375                 380
```

Tyr Pro Leu Phe Asp Gly Ile Phe Cys Ser Pro Pro His His His His
385                 390                 395                 400

His His

<210> SEQ ID NO 17
<211> LENGTH: 1203
<212> TYPE: DNA
<213> ORGANISM: Artificial sequence
<220> FEATURE:
<223> OTHER INFORMATION: synthetic

<400> SEQUENCE: 17

```
attggatcca ctaaaatgtg gtcttggaag tgtcttttat tctgggctgt cttggtgacc      60
gccactcttt gcacagcagc gatctctgtt actatggaca catcctcag tggcttcgag     120
aacgagtacg acgtaatcta cctaaagccc cttgccggtg tctaccgttc attgaagaaa    180
cagatagaaa agaatatttt cacgttcaac ctcaacctaa atgacatcct caactcgcgc    240
ctcaagaagc gaaaatactt cctcgacgtg ttggaatccg accttatgca atttaagcac    300
attagctcta acgagtacat catagaggac agcttcaagc tcttgaattc agaacagaag    360
aacaccctcc taaagtccta caaatacatt aaggagtctg ttgagaacga catcaagttc    420
gcccaggaag gaattagcta ctatgagaaa gtcctggcta aatacaagga cgacttggaa    480
agcattaaga aggtaatcaa agaagagaag gaaaagtttc cgagctctcc acccacaact    540
ccccccatcgc ctgcaaagac cgacgagcag aaaaaagaaa gtaagttcct tccattcctc    600
accaacatcg aaactctata taacaacctg gtgaacaaga ttgatgacta cttaatcaac    660
ttgaaggcga aaattaatga ctgtaacgtc gaaaaggatg aagcccacgt taagatcacc    720
aagctttccg atctcaaagc catcgacgat aagattgacc tgtttaagaa ccacaacgat    780
ttcgacgcaa tcaaaaagtt gatcaacgac gatactaaga agacatgct tggaaaactg    840
ctgtcgacag gcttggtcca aaacttcccg aacaccatta taagcaagct gatcgaagga    900
aagtttcagg atatgctgaa catctctcag catcaatgcg tgaagaagca atgtcccgag    960
aattcaggtt gcttccgcca cttagacgaa agggaggaat gtaaatgcct gctgaattat   1020
aaacaggaag gagacaagtg cgtagagaat cctaacccaa cctgtaacga aaataacggt   1080
ggctgcgatg ctgacgctaa gtgtaccgag gaggacagcg gttccaatgg caagaaaata   1140
acttgcgaat gcacgaagcc cgatagttac cctctcttcg acggtatctt ctgctcccca   1200
cct                                                                 1203
```

<210> SEQ ID NO 18
<211> LENGTH: 396
<212> TYPE: PRT
<213> ORGANISM: Artificial sequence
<220> FEATURE:
<223> OTHER INFORMATION: synthetic

<400> SEQUENCE: 18

Met Trp Ser Trp Lys Cys Leu Leu Phe Trp Ala Val Leu Val Thr Ala
1               5                   10                  15

Thr Leu Cys Thr Ala Ala Ile Ser Val Thr Met Asp Asn Ile Leu Ser
                20                  25                  30

Gly Phe Glu Asn Glu Tyr Asp Val Ile Tyr Leu Lys Pro Leu Ala Gly
            35                  40                  45

Val Tyr Arg Ser Leu Lys Lys Gln Ile Glu Lys Asn Ile Phe Thr Phe
        50                  55                  60

```
Asn Leu Asn Leu Asn Asp Ile Leu Asn Ser Arg Leu Lys Lys Arg Lys
 65                  70                  75                  80

Tyr Phe Leu Asp Val Leu Glu Ser Asp Leu Met Gln Phe Lys His Ile
                 85                  90                  95

Ser Ser Asn Glu Tyr Ile Ile Glu Asp Ser Phe Lys Leu Leu Asn Ser
            100                 105                 110

Glu Gln Lys Asn Thr Leu Leu Lys Ser Tyr Lys Tyr Ile Lys Glu Ser
        115                 120                 125

Val Glu Asn Asp Ile Lys Phe Ala Gln Glu Gly Ile Ser Tyr Tyr Glu
130                 135                 140

Lys Val Leu Ala Lys Tyr Lys Asp Asp Leu Glu Ser Ile Lys Lys Val
145                 150                 155                 160

Ile Lys Glu Glu Lys Glu Lys Phe Pro Ser Ser Pro Thr Thr Pro
                165                 170                 175

Pro Ser Pro Ala Lys Thr Asp Glu Gln Lys Lys Glu Ser Lys Phe Leu
            180                 185                 190

Pro Phe Leu Thr Asn Ile Glu Thr Leu Tyr Asn Asn Leu Val Asn Lys
        195                 200                 205

Ile Asp Asp Tyr Leu Ile Asn Leu Lys Ala Lys Ile Asn Asp Cys Asn
210                 215                 220

Val Glu Lys Asp Glu Ala His Val Lys Ile Thr Lys Leu Ser Asp Leu
225                 230                 235                 240

Lys Ala Ile Asp Asp Lys Ile Asp Leu Phe Lys Asn His Asn Asp Phe
                245                 250                 255

Asp Ala Ile Lys Lys Leu Ile Asn Asp Asp Thr Lys Lys Asp Met Leu
            260                 265                 270

Gly Lys Leu Leu Ser Thr Gly Leu Val Gln Asn Phe Pro Asn Thr Ile
        275                 280                 285

Ile Ser Lys Leu Ile Glu Gly Lys Phe Gln Asp Met Leu Asn Ile Ser
290                 295                 300

Gln His Gln Cys Val Lys Lys Gln Cys Pro Glu Asn Ser Gly Cys Phe
305                 310                 315                 320

Arg His Leu Asp Glu Arg Glu Glu Cys Lys Cys Leu Leu Asn Tyr Lys
                325                 330                 335

Gln Glu Gly Asp Lys Cys Val Glu Asn Pro Asn Pro Thr Cys Asn Glu
            340                 345                 350

Asn Asn Gly Gly Cys Asp Ala Asp Ala Lys Cys Thr Glu Glu Asp Ser
        355                 360                 365

Gly Ser Asn Gly Lys Lys Ile Thr Cys Glu Cys Thr Lys Pro Asp Ser
370                 375                 380

Tyr Pro Leu Phe Asp Gly Ile Phe Cys Ser Pro Pro
385                 390                 395

<210> SEQ ID NO 19
<211> LENGTH: 50
<212> TYPE: DNA
<213> ORGANISM: Artificial sequence
<220> FEATURE:
<223> OTHER INFORMATION: synthetic

<400> SEQUENCE: 19
attggatcca ctaaaatgtg gtcttggaag tgtctttat tctgggctgt           50

<210> SEQ ID NO 20
<211> LENGTH: 51
<212> TYPE: DNA
```

<213> ORGANISM: Artificial sequence
<220> FEATURE:
<223> OTHER INFORMATION: synthetic

<400> SEQUENCE: 20
ccactctttg cacagcagcg atctctgtta ctatggacaa catcctcagt g    51

<210> SEQ ID NO 21
<211> LENGTH: 50
<212> TYPE: DNA
<213> ORGANISM: Artificial sequence
<220> FEATURE:
<223> OTHER INFORMATION: synthetic

<400> SEQUENCE: 21
cgagtacgac gtaatctacc taaagcccct tgccggtgtc taccgttcat    50

<210> SEQ ID NO 22
<211> LENGTH: 53
<212> TYPE: DNA
<213> ORGANISM: Artificial sequence
<220> FEATURE:
<223> OTHER INFORMATION: synthetic

<400> SEQUENCE: 22
gaaaagaata ttttcacgtt caacctcaac ctaaatgaca tcctcaactc gcg    53

<210> SEQ ID NO 23
<211> LENGTH: 51
<212> TYPE: DNA
<213> ORGANISM: Artificial sequence
<220> FEATURE:
<223> OTHER INFORMATION: synthetic

<400> SEQUENCE: 23
cgaaaatact tcctcgacgt gttggaatcc gaccttatgc aatttaagca c    51

<210> SEQ ID NO 24
<211> LENGTH: 54
<212> TYPE: DNA
<213> ORGANISM: Artificial sequence
<220> FEATURE:
<223> OTHER INFORMATION: synthetic

<400> SEQUENCE: 24
acgagtacat catagaggac agcttcaagc tcttgaattc agaacagaag aaca    54

<210> SEQ ID NO 25
<211> LENGTH: 54
<212> TYPE: DNA
<213> ORGANISM: Artificial sequence
<220> FEATURE:
<223> OTHER INFORMATION: synthetic

<400> SEQUENCE: 25
gtcctacaaa tacattaagg agtctgttga gaacgacatc aagttcgccc agga    54

<210> SEQ ID NO 26
<211> LENGTH: 50
<212> TYPE: DNA
<213> ORGANISM: Artificial sequence
<220> FEATURE:
<223> OTHER INFORMATION: synthetic

<400> SEQUENCE: 26
tactatgaga aagtcctggc taaatacaag gacgacttgg aaagcattaa    50

<210> SEQ ID NO 27
<211> LENGTH: 47
<212> TYPE: DNA
<213> ORGANISM: Artificial sequence
<220> FEATURE:
<223> OTHER INFORMATION: synthetic

<400> SEQUENCE: 27
aaagaagaga aggaaaagtt tccgagctct ccacccacaa ctccccc        47

<210> SEQ ID NO 28
<211> LENGTH: 47
<212> TYPE: DNA
<213> ORGANISM: Artificial sequence
<220> FEATURE:
<223> OTHER INFORMATION: synthetic

<400> SEQUENCE: 28
aagaccgacg agcagaaaaa agaaagtaag ttccttccat tcctcac        47

<210> SEQ ID NO 29
<211> LENGTH: 57
<212> TYPE: DNA
<213> ORGANISM: Artificial sequence
<220> FEATURE:
<223> OTHER INFORMATION: synthetic

<400> SEQUENCE: 29
actctatata acaacctggt gaacaagatt gatgactact taatcaactt gaaggcg        57

<210> SEQ ID NO 30
<211> LENGTH: 51
<212> TYPE: DNA
<213> ORGANISM: Artificial sequence
<220> FEATURE:
<223> OTHER INFORMATION: synthetic

<400> SEQUENCE: 30
gactgtaacg tcgaaaagga tgaagcccac gttaagatca ccaagctttc c        51

<210> SEQ ID NO 31
<211> LENGTH: 50
<212> TYPE: DNA
<213> ORGANISM: Artificial sequence
<220> FEATURE:
<223> OTHER INFORMATION: synthetic

<400> SEQUENCE: 31
ccatcgacga taagattgac ctgtttaaga accacaacga tttcgacgca        50

<210> SEQ ID NO 32
<211> LENGTH: 51
<212> TYPE: DNA
<213> ORGANISM: Artificial sequence
<220> FEATURE:
<223> OTHER INFORMATION: synthetic

<400> SEQUENCE: 32
tgatcaacga cgatactaag aaagacatgc ttggaaaact gctgtcgaca g        51

<210> SEQ ID NO 33
<211> LENGTH: 48
<212> TYPE: DNA
<213> ORGANISM: Artificial sequence
<220> FEATURE:

<223> OTHER INFORMATION: synthetic

<400> SEQUENCE: 33
aaacttcccg aacaccatta taagcaagct gatcgaagga aagtttca            48

<210> SEQ ID NO 34
<211> LENGTH: 49
<212> TYPE: DNA
<213> ORGANISM: Artificial sequence
<220> FEATURE:
<223> OTHER INFORMATION: synthetic

<400> SEQUENCE: 34
aacatctctc agcatcaatg cgtgaagaag caatgtcccg agaattcag            49

<210> SEQ ID NO 35
<211> LENGTH: 50
<212> TYPE: DNA
<213> ORGANISM: Artificial sequence
<220> FEATURE:
<223> OTHER INFORMATION: synthetic

<400> SEQUENCE: 35
ccacttagac gaaagggagg aatgtaaatg cctgctgaat tataaacagg           50

<210> SEQ ID NO 36
<211> LENGTH: 47
<212> TYPE: DNA
<213> ORGANISM: Artificial sequence
<220> FEATURE:
<223> OTHER INFORMATION: synthetic

<400> SEQUENCE: 36
gtgcgtagag aatcctaacc caacctgtaa cgaaaataac ggtggct              47

<210> SEQ ID NO 37
<211> LENGTH: 49
<212> TYPE: DNA
<213> ORGANISM: Artificial sequence
<220> FEATURE:
<223> OTHER INFORMATION: synthetic

<400> SEQUENCE: 37
cgctaagtgt accgaggagg acagcggttc caatggcaag aaaataact            49

<210> SEQ ID NO 38
<211> LENGTH: 48
<212> TYPE: DNA
<213> ORGANISM: Artificial sequence
<220> FEATURE:
<223> OTHER INFORMATION: synthetic

<400> SEQUENCE: 38
gaagcccgat agttaccctc tcttcgacgg tatcttctgc tccccacc             48

<210> SEQ ID NO 39
<211> LENGTH: 39
<212> TYPE: DNA
<213> ORGANISM: Artificial sequence
<220> FEATURE:
<223> OTHER INFORMATION: synthetic

<400> SEQUENCE: 39
ttcgacgcaa tcaaaaagtt gatcaacgac gatactaag                      39

```
<210> SEQ ID NO 40
<211> LENGTH: 41
<212> TYPE: DNA
<213> ORGANISM: Artificial sequence
<220> FEATURE:
<223> OTHER INFORMATION: synthetic

<400> SEQUENCE: 40
aaagacatgc ttggaaaact gctgtcgaca ggcttggtcc a                41

<210> SEQ ID NO 41
<211> LENGTH: 41
<212> TYPE: DNA
<213> ORGANISM: Artificial sequence
<220> FEATURE:
<223> OTHER INFORMATION: synthetic

<400> SEQUENCE: 41
gaggacagct tcaagctctt gaattcagaa cagaagaaca c                41

<210> SEQ ID NO 42
<211> LENGTH: 40
<212> TYPE: DNA
<213> ORGANISM: Artificial sequence
<220> FEATURE:
<223> OTHER INFORMATION: synthetic

<400> SEQUENCE: 42
cctcctaaag tcctacaaat acattaagga gtctgttgag                  40

<210> SEQ ID NO 43
<211> LENGTH: 40
<212> TYPE: DNA
<213> ORGANISM: Artificial sequence
<220> FEATURE:
<223> OTHER INFORMATION: synthetic

<400> SEQUENCE: 43
aacgacatca agttcgccca ggaaggaatt agctactatg                  40

<210> SEQ ID NO 44
<211> LENGTH: 40
<212> TYPE: DNA
<213> ORGANISM: Artificial sequence
<220> FEATURE:
<223> OTHER INFORMATION: synthetic

<400> SEQUENCE: 44
agaaagtcct ggctaaatac aaggacgact tggaaagcat                  40

<210> SEQ ID NO 45
<211> LENGTH: 39
<212> TYPE: DNA
<213> ORGANISM: Artificial sequence
<220> FEATURE:
<223> OTHER INFORMATION: synthetic

<400> SEQUENCE: 45
taagaaggta atcaaagaag agaaggaaaa gtttccgag                   39

<210> SEQ ID NO 46
<211> LENGTH: 16
<212> TYPE: DNA
<213> ORGANISM: Artificial sequence
<220> FEATURE:
<223> OTHER INFORMATION: synthetic
```

<400> SEQUENCE: 46
ctctccaccc acaact                                                        16

<210> SEQ ID NO 47
<211> LENGTH: 40
<212> TYPE: DNA
<213> ORGANISM: Artificial sequence
<220> FEATURE:
<223> OTHER INFORMATION: synthetic

<400> SEQUENCE: 47
ggaattagct actatgagaa agtcctggct aaatacaagg                              40

<210> SEQ ID NO 48
<211> LENGTH: 49
<212> TYPE: DNA
<213> ORGANISM: Artificial sequence
<220> FEATURE:
<223> OTHER INFORMATION: synthetic

<400> SEQUENCE: 48
ctgctgtgca aagagtggcg gtcaccaaga cagcccagaa taaaagaca                    49

<210> SEQ ID NO 49
<211> LENGTH: 51
<212> TYPE: DNA
<213> ORGANISM: Artificial sequence
<220> FEATURE:
<223> OTHER INFORMATION: synthetic

<400> SEQUENCE: 49
aggtagatta cgtcgtactc gttctcgaag ccactgagga tgttgtccat a                 51

<210> SEQ ID NO 50
<211> LENGTH: 51
<212> TYPE: DNA
<213> ORGANISM: Artificial sequence
<220> FEATURE:
<223> OTHER INFORMATION: synthetic

<400> SEQUENCE: 50
ttgaacgtga aaatattctt ttctatctgt ttcttcaatg aacggtagac a                 51

<210> SEQ ID NO 51
<211> LENGTH: 47
<212> TYPE: DNA
<213> ORGANISM: Artificial sequence
<220> FEATURE:
<223> OTHER INFORMATION: synthetic

<400> SEQUENCE: 51
acgtcgagga agtattttcg cttcttgagg cgcgagttga ggatgtc                      47

<210> SEQ ID NO 52
<211> LENGTH: 53
<212> TYPE: DNA
<213> ORGANISM: Artificial sequence
<220> FEATURE:
<223> OTHER INFORMATION: synthetic

<400> SEQUENCE: 52
ctgtcctcta tgatgtactc gttagagcta atgtgcttaa attgcataag gtc               53

<210> SEQ ID NO 53
<211> LENGTH: 57

```
<212> TYPE: DNA
<213> ORGANISM: Artificial sequence
<220> FEATURE:
<223> OTHER INFORMATION: synthetic

<400> SEQUENCE: 53
agactcctta atgtatttgt aggactttag gagggtgttc ttctgttctg aattcaa        57

<210> SEQ ID NO 54
<211> LENGTH: 46
<212> TYPE: DNA
<213> ORGANISM: Artificial sequence
<220> FEATURE:
<223> OTHER INFORMATION: synthetic

<400> SEQUENCE: 54
gccaggactt tctcatagta gctaattcct tcctgggcga acttga                    46

<210> SEQ ID NO 55
<211> LENGTH: 51
<212> TYPE: DNA
<213> ORGANISM: Artificial sequence
<220> FEATURE:
<223> OTHER INFORMATION: synthetic

<400> SEQUENCE: 55 aaactttcc ttctcttctt tgattacctt cttaatgctt tccaagtcgt c               51

<210> SEQ ID NO 56
<211> LENGTH: 44
<212> TYPE: DNA
<213> ORGANISM: Artificial sequence
<220> FEATURE:
<223> OTHER INFORMATION: synthetic

<400> SEQUENCE: 56
tttctgctcg tcggtctttg caggcgatgg gggagttgtg ggtg                      44

<210> SEQ ID NO 57
<211> LENGTH: 53
<212> TYPE: DNA
<213> ORGANISM: Artificial sequence
<220> FEATURE:
<223> OTHER INFORMATION: synthetic

<400> SEQUENCE: 57
gttcaccagg ttgttatata gagtttcgat gttggtgagg aatggaagga act            53

<210> SEQ ID NO 58
<211> LENGTH: 52
<212> TYPE: DNA
<213> ORGANISM: Artificial sequence
<220> FEATURE:
<223> OTHER INFORMATION: synthetic

<400> SEQUENCE: 58 tcctttcga cgttacagtc attaattttc gccttcaagt tgattaagta gt              52

<210> SEQ ID NO 59
<211> LENGTH: 51
<212> TYPE: DNA
<213> ORGANISM: Artificial sequence
<220> FEATURE:
<223> OTHER INFORMATION: synthetic

<400> SEQUENCE: 59
```
gtcaatctta tcgtcgatgg ctttgagatc ggaaagcttg gtgatcctaa c    51

<210> SEQ ID NO 60
<211> LENGTH: 52
<212> TYPE: DNA
<213> ORGANISM: Artificial sequence
<220> FEATURE:
<223> OTHER INFORMATION: synthetic

<400> SEQUENCE: 60
ttcttagtat cgtcgttgat caactttttg attgcgtcga aatcgttgtg gt    52

<210> SEQ ID NO 61
<211> LENGTH: 47
<212> TYPE: DNA
<213> ORGANISM: Artificial sequence
<220> FEATURE:
<223> OTHER INFORMATION: synthetic

<400> SEQUENCE: 61
atggtgttcg ggaagttttg gaccaagcct gtcgacagca gttttcc    47

<210> SEQ ID NO 62
<211> LENGTH: 50
<212> TYPE: DNA
<213> ORGANISM: Artificial sequence
<220> FEATURE:
<223> OTHER INFORMATION: synthetic

<400> SEQUENCE: 62
cattgatgct gagagatgtt cagcatatcc tgaaactttc cttcgatcag    50

<210> SEQ ID NO 63
<211> LENGTH: 48
<212> TYPE: DNA
<213> ORGANISM: Artificial sequence
<220> FEATURE:
<223> OTHER INFORMATION: synthetic

<400> SEQUENCE: 63 ctcccttcg tctaagtggc ggaagcaacc tgaattctcg ggacattg    48

<210> SEQ ID NO 64
<211> LENGTH: 51
<212> TYPE: DNA
<213> ORGANISM: Artificial sequence
<220> FEATURE:
<223> OTHER INFORMATION: synthetic

<400> SEQUENCE: 64
ggttaggatt ctctacgcac ttgtctcctt cctgtttata attcagcagg c    51

<210> SEQ ID NO 65
<211> LENGTH: 46
<212> TYPE: DNA
<213> ORGANISM: Artificial sequence
<220> FEATURE:
<223> OTHER INFORMATION: synthetic

<400> SEQUENCE: 65
ctcctcggta cacttagcgt cagcatcgca gccaccgtta ttttcg    46

<210> SEQ ID NO 66
<211> LENGTH: 50
<212> TYPE: DNA
<213> ORGANISM: Artificial sequence

```
<220> FEATURE:
<223> OTHER INFORMATION: synthetic

<400> SEQUENCE: 66
agggtaacta tcgggcttcg tgcattcgca agttattttc ttgccattgg      50

<210> SEQ ID NO 67
<211> LENGTH: 56
<212> TYPE: DNA
<213> ORGANISM: Artificial sequence
<220> FEATURE:
<223> OTHER INFORMATION: synthetic

<400> SEQUENCE: 67
ggcgtaggta ccttattaat gatgatgatg atgatgaggt ggggagcaga agatac      56

<210> SEQ ID NO 68
<211> LENGTH: 27
<212> TYPE: DNA
<213> ORGANISM: Artificial sequence
<220> FEATURE:
<223> OTHER INFORMATION: synthetic

<400> SEQUENCE: 68
tttttgattg cgtcgaaatc gttgtgg      27

<210> SEQ ID NO 69
<211> LENGTH: 43
<212> TYPE: DNA
<213> ORGANISM: Artificial sequence
<220> FEATURE:
<223> OTHER INFORMATION: synthetic

<400> SEQUENCE: 69
cagttttcca agcatgtctt tcttagtatc gtcgttgatc aac      43

<210> SEQ ID NO 70
<211> LENGTH: 35
<212> TYPE: DNA
<213> ORGANISM: Artificial sequence
<220> FEATURE:
<223> OTHER INFORMATION: synthetic

<400> SEQUENCE: 70
agttgtgggt ggagagctcg gaaactttc cttct      35

<210> SEQ ID NO 71
<211> LENGTH: 40
<212> TYPE: DNA
<213> ORGANISM: Artificial sequence
<220> FEATURE:
<223> OTHER INFORMATION: synthetic

<400> SEQUENCE: 71
cttctttgat taccttctta atgctttcca agtcgtcctt      40

<210> SEQ ID NO 72
<211> LENGTH: 41
<212> TYPE: DNA
<213> ORGANISM: Artificial sequence
<220> FEATURE:
<223> OTHER INFORMATION: synthetic

<400> SEQUENCE: 72
gtatttagcc aggactttct catagtagct aattccttcc t      41
```

<210> SEQ ID NO 73
<211> LENGTH: 40
<212> TYPE: DNA
<213> ORGANISM: Artificial sequence
<220> FEATURE:
<223> OTHER INFORMATION: synthetic

<400> SEQUENCE: 73
gggcgaactt gatgtcgttc tcaacagact ccttaatgta                40

<210> SEQ ID NO 74
<211> LENGTH: 40
<212> TYPE: DNA
<213> ORGANISM: Artificial sequence
<220> FEATURE:
<223> OTHER INFORMATION: synthetic

<400> SEQUENCE: 74
tttgtaggac tttaggaggg tgttcttctg ttctgaattc                40

<210> SEQ ID NO 75
<211> LENGTH: 20
<212> TYPE: DNA
<213> ORGANISM: Artificial sequence
<220> FEATURE:
<223> OTHER INFORMATION: synthetic

<400> SEQUENCE: 75
aagagcttga agctgtcctc                                      20

<210> SEQ ID NO 76
<211> LENGTH: 40
<212> TYPE: DNA
<213> ORGANISM: Artificial sequence
<220> FEATURE:
<223> OTHER INFORMATION: synthetic

<400> SEQUENCE: 76
ccttgtattt agccaggact ttctcatagt agctaattcc                40

<210> SEQ ID NO 77
<211> LENGTH: 5
<212> TYPE: PRT
<213> ORGANISM: Artificial sequence
<220> FEATURE:
<223> OTHER INFORMATION: glycine-serine polymer linker

<400> SEQUENCE: 77

Gly Ser Gly Gly Ser
1               5

<210> SEQ ID NO 78
<211> LENGTH: 4
<212> TYPE: PRT
<213> ORGANISM: Artificial sequence
<220> FEATURE:
<223> OTHER INFORMATION: glycine-serine polymer linker

<400> SEQUENCE: 78

Gly Gly Gly Ser
1

<210> SEQ ID NO 79
<211> LENGTH: 20
<212> TYPE: DNA
<213> ORGANISM: Artificial sequence -continued

```
<220> FEATURE:
<223> OTHER INFORMATION: consensus translation initiation sequence
<220> FEATURE:
<221> NAME/KEY: misc_feature
<222> LOCATION: (3)..(3)
<223> OTHER INFORMATION: "n" at position 3 can be g or t
<220> FEATURE:
<221> NAME/KEY: misc_feature
<222> LOCATION: (4)..(4)
<223> OTHER INFORMATION: "n" at position 4 can be a or t
<220> FEATURE:
<221> NAME/KEY: misc_feature
<222> LOCATION: (6)..(6)
<223> OTHER INFORMATION: "n" at position 6 can be t or a
<220> FEATURE:
<221> NAME/KEY: misc_feature
<222> LOCATION: (7)..(7)
<223> OTHER INFORMATION: "n" at position 7 can be a or c
<220> FEATURE:
<221> NAME/KEY: misc_feature
<222> LOCATION: (15)..(15)
<223> OTHER INFORMATION: "n" at position 15 can be a or c
<220> FEATURE:
<221> NAME/KEY: misc_feature
<222> LOCATION: (16)..(16)
<223> OTHER INFORMATION: "n" at position 16 can be t or a
<220> FEATURE:
<221> NAME/KEY: misc_feature
<222> LOCATION: (17)..(17)
<223> OTHER INFORMATION: "n" at position 17 can be g or a
<220> FEATURE:
<221> NAME/KEY: misc_feature
<222> LOCATION: (20)..(20)
<223> OTHER INFORMATION: "n" at position 20 can be any base

<400> SEQUENCE: 79
aannannaaa atgannnaan                                                   20
```

What we claimed is:

1. An isolated p42 nucleic acid encoding a p42 polypeptide from the C-terminal processing fragment of *Plasmodium falciparum* major merozoite surface protein gp 195, wherein said p42 nucleic acid comprises a nucleic acid which hybridizes under high stringency conditions to the complement of the nucleic acid of SEQ ID NO: 17;

wherein said high stringency conditions comprise a salt concentration less than about 1.0 M at about a pH of 7.0 to 8.3 and a temperature of at least about 30° C.; and wherein said encoded p42 polypeptide can induce an anti-plasmodium immune response in a primate.

2. The isolated p42 nucleic acid of claim 1, wherein said nucleic acid comprises the nucleotide sequence of SEQ ID NO: 6.

3. An isolated p42 nucleic acid encoding a p42 polypeptide from the C-terminal processing fragment of *Plasmodium falciparum* major merozoite surface protein gp 195, wherein said nucleic acid comprises the nucleotide sequence of SEQ ID NO: 17.

4. An insect cell expression vector comprising the p42 nucleic acid of claim 1 or 3.

5. The insect cell expression vector of claim 4, wherein said expression vector is a baculovirus vector.

6. The insect cell expression vector of claim 4, wherein said expression vector further comprises an optimized promoter operably linked to said nucleic acid.

7. The insect cell expression vector of claim 6, wherein said expression vector is a baculovirus vector.

8. An insect cell comprising the insect cell expression vector of claim 4.

9. The insect cell of claim 8, wherein said insect cell is a *Trichoplusia ni* cell.

10. An isolated p42 nucleic acid encoding a p42 polypeptide from the C-terminal processing fragment of *Plasmodium falciparum* major merozoite surface protein gp 195, wherein said nucleic acid comprises the nucleotides 1-1200 of the nucleotide sequence of SEQ ID NO: 17.

* * * * *